US008435763B2

(12) United States Patent
Koizumi et al.

(10) Patent No.: US 8,435,763 B2
(45) Date of Patent: May 7, 2013

(54) PROCESSES FOR PRODUCING SUGAR NUCLEOTIDES AND COMPLEX CARBOHYDRATES

(75) Inventors: Satoshi Koizumi, Machida (JP); Katsutoshi Sasaki, Machida (JP); Tetsuo Endo, Machida (JP); Kazuhiko Tabata, Machida (JP); Akio Ozaki, Machida (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 1479 days.

(21) Appl. No.: 10/940,026

(22) Filed: Sep. 14, 2004

(65) Prior Publication Data

US 2005/0019874 A1  Jan. 27, 2005

Related U.S. Application Data

(62) Division of application No. 09/068,528, filed as application No. PCT/JP97/03226 on Sep. 12, 1997, now Pat. No. 6,821,756.

(30) Foreign Application Priority Data

Sep. 17, 1996 (JP) .................................. 1996-244451
Oct. 28, 1996 (JP) .................................. 1996-285066

(51) Int. Cl.
*C12P 19/30* (2006.01)
*C12P 19/00* (2006.01)
*C12P 1/00* (2006.01)
*C12P 39/00* (2006.01)
*C12N 1/00* (2006.01)
*C12N 1/20* (2006.01)

(52) U.S. Cl.
USPC ................... 435/89; 435/72; 435/41; 435/42; 435/243; 435/252.3; 435/252.33

(58) Field of Classification Search .................... 435/89, 435/72, 41, 42, 243, 252.3, 252.33
See application file for complete search history.

(56) References Cited

FOREIGN PATENT DOCUMENTS

| EP | 0553821 | 8/1993 |
| EP | 0861902 | 9/1998 |
| JP | 46-40756 | 12/1971 |
| JP | 47-1837 | 1/1972 |
| JP | 47-46351 | 11/1972 |
| JP | 57-18893 | 1/1982 |
| JP | 62-134096 | 6/1987 |
| JP | 1-500560 | 3/1989 |
| JP | 02177891 | 7/1990 |
| JP | 7-233187 | 9/1995 |
| WO | WO 95/02683 | * 7/1995 |
| WO | WO 96/32491 | * 10/1996 |

OTHER PUBLICATIONS

Nyholm et al., A method for production of C13/N15 double labelled RNA in *E.coli*, and subsequent in vitro synthesis of ribonucleotide 5' triphosphates. J. Biochem. Biophys. methods, 1995, vol. 30: 59-68.*
Mengin-Lecreulx et al., Copurification of glucosamine-1-phosphate acetyltransferase . . . synthesis. J. Bacteriol., 1994, vol. 176 (18): 5788-5795.*
Snetkova et al., Enzymatic synthesis of multiple tritium-labeled nucleosides and nucleotides from nitrogen bases and ribose. Translated from Khimiya Prirodnykh Soedinenii, No. 2, pp. 258-264, Mar.-Apr. 1988. pp. 221-226.*
Aoki et al., cloning of a Streptococcus mutans glucosyltransferase gene coding for insoluble glucan synthesis. Infn. Immun., 1986, vol. 53 (3): 587-594.*
*Enzyme Catalysts in Organic Synthesis*, "Hydrolysis and formation of glycosidic bonds", Drautz, K. and Waldmann, H., vol. 1 (1995), pp. 279-317.
Liebigs Ann. Chem., Thiem et al., vol. II (1990), pp. 1101-1105.
Pattabiraman, et al., "Interconversion of N-Acetyl Glucosamine . . . ", J. Sci. Industr. Res., vol. 21C (1962), pp. 352-354.
Heidlas, et al., "Gram-Scale Synthesis of Uridine 5'-Diphospho-$N$-acetylglucosamine", J. Org. Chem., vol. 57 (1992), pp. 146-151.
Rao, et al., "Synthesis of UDP-$N$-[1-$^{14}$C]Acetyl . . . ", Analytic Biochemistry, vol. 91 (1978), pp. 490-495.
Weissborn, et al. "UTP:α-D-Glucose-1-Phosphate Uridylyltransferase . . . ", Journal of Bacteriology, vol. 176, No. 9 (1994), pp. 2611-2618.
Zapata, et al., "Sequence of the Cloned *Escherichia coli* K1 CMP-N-acetylneuraminic Acid Synthetase Gene", *Jour. of Bio. Chem.*, vol. 264,, No. 25 (1989), pp. 14769-14774.
Stryer, Biochemistry, 3$^{rd}$ Edition (1988), p. 553.
Kuehn, et al., "Uridine Diphosphoglucose Pyrophosphorylase Activity and Differentiation in the Acellular Slime Mold *Physarum*", *Journal of Bact.*, vol. 120, No. 3 (1974), pp. 1151-1157.

* cited by examiner

*Primary Examiner* — Ganapathirama Raghu
(74) *Attorney, Agent, or Firm* — Fitzpatrick, Cella, Harper & Scinto

(57) ABSTRACT

This invention relates to a process for producing a sugar nucleotide, in which a) a culture broth of a microorganism capable of producing NTP from a nucleotide precursor, or a treated product of the culture broth, and b) a culture broth of a microorganism capable of producing a sugar nucleotide from a sugar and NTP, or a treated product of the culture broth, are used as enzyme sources; a process for producing a complex carbohydrate, in which the above-described a) and b) and c) a culture broth of a microorganism, an animal cell or an insect cell capable of producing a complex carbohydrate from a sugar nucleotide and a complex carbohydrate precursor, or a treated product of the culture broth, are used as enzyme sources; a process for producing a complex carbohydrate, in which a culture broth of a microorganism, an animal cell or an insect cell capable of producing a complex carbohydrate from a sugar nucleotide and a complex carbohydrate precursor, or a treated product of the culture broth, is as an enzyme source; and a process for producing N-acetylglucosamine-1-phosphate, in which a culture broth of a microorganism having strong galactokinase activity, or a treated product of the culture broth, is used as the enzyme source.

21 Claims, 16 Drawing Sheets

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: synthetic DNA (xi) SEQUENCE DESCRIPTION: SEQ ID NO: 1:

GGAGAAAGCT TATGGCTGCC ATTAATACGA A                              31

(2) INFORMATION FOR SEQ ID NO: 2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: synthetic DNA (xi) SEQUENCE DESCRIPTION: SEQ ID NO: 2:

AACACGGATC CGGATGTTAC TTCTTAATGC                                30

(2) INFORMATION FOR SEQ ID NO: 3:

(i) SEQUENCE CHARACTERISTICS:
      (A) LENGTH: 28 base pairs
      (B) TYPE: nucleic acid

```
        (C) STRANDEDNESS: single
        (D) TOPOLOGY: linear (ii) MOLECULE TYPE: synthetic DNA (xi) SEQUENCE DESCRIPTION: SEQ ID NO: 3:

ATGGAGGATC CTGCTCTGTA TACCGTCT                                    28

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 4:

TGCTGGTCGA CCTGCGCTTG                                             20

(2) INFORMATION FOR SEQ ID NO: 5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 5:

AAGGAAAGCT TATGACGCAA TTTAATCCCG T                                31

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 6:

GCAAAGTTAA CAGTCGGTAC                                             20

(2) INFORMATION FOR SEQ ID NO: 7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 7:

TCAGGAAGCT TATGTTGAAT AATGCTATGA G                                31

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA
```

(xi) SEQUENCE DESCRIPTION: SEQ ID NO: 8:

TCTCCGGATC CCATGTGACC GGGTTAG                                                      27

(2) INFORMATION FOR SEQ ID NO: 9:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO: 9:

TCTAAATCGA TGCAGACAAA GGACAAAG                                                     28

(2) INFORMATION FOR SEQ ID NO: 10:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO: 10:

TTGCAGGATC CTCGTAGGCC TGATAAG                                                      27

(2) INFORMATION FOR SEQ ID NO: 11:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO: 11:

TGATATCCGC TCCCTTTCCG                                                              20

(2) INFORMATION FOR SEQ ID NO: 12:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO: 12:

ACAGCGGATC CGATGTGTTC GCTGAG                                                       26

(2) INFORMATION FOR SEQ ID NO: 13:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: synthetic DNA (xi) SEQUENCE DESCRIPTION: SEQ ID NO: 13:

ACAGCAAGCT TTTGACTTTA GCGGAGCAG                                                    29

(2) INFORMATION FOR SEQ ID NO: 14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 14:

GAGTTGGATC CCGATATAAA AGGAAGGAT                    29

(2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 15:

TTTTTAAGCT TCATTTATCA AGAGT                         25

(2) INFORMATION FOR SEQ ID NO: 16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 16:

TTTTTGATAT CCCCAATGCT GGGGGTTTTT G                31

(2) INFORMATION FOR SEQ ID NO: 17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 17:

CGTCAAAGCT TAAATGATAT TCGGGGATAA T                31

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 18:

AGGGAGGATC CGACATTACT CGTTC                         25

(2) INFORMATION FOR SEQ ID NO: 19:

(i) SEQUENCE CHARACTERISTICS:
        (A) LENGTH: 33 base pairs
        (B) TYPE: nucleic acid

```
        (C) STRANDEDNESS: single
        (D) TOPOLOGY: linear (ii) MOLECULE TYPE: synthetic DNA (xi) SEQUENCE DESCRIPTION: SEQ ID NO: 19:

CCGCAAGATC TCGTAAAAAG GGTATCGATA AGC                             33

(2) INFORMATION FOR SEQ ID NO: 20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 20:

TTGGGAAGCT TCCGGCAAAT GTGGTTT                                    27

(2) INFORMATION FOR SEQ ID NO: 21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 21:

ATAAACTCGA GAGAGACAAG CGGAG                                      25

(2) INFORMATION FOR SEQ ID NO: 22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 22:

TATTATCGAT GAATTAATAA TTCATAG                                    27

(2) INFORMATION FOR SEQ ID NO: 23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 23:

CTCTGGATCC AGTTACGTAT AATAT                                      25

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA
```

-continued (xi) SEQUENCE DESCRIPTION: SEQ ID NO: 24:

CGGCAAGCTT ATTGTGCCTT TCCAATAAAA                                          30

(2) INFORMATION FOR SEQ ID NO: 25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 25:

ACTTGGATCC CCGTCAATAA ATCTTGCG                                            28

(2) INFORMATION FOR SEQ ID NO: 26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 26:

GGTAAAGCTT ATGCAAAACC ACGTTATCAG                                          30

(2) INFORMATION FOR SEQ ID NO: 27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 27:

AAACGGATCC TTATTGGAAA GGCACAATA                                           29

PROCESSES FOR PRODUCING SUGAR NUCLEOTIDES AND COMPLEX CARBOHYDRATES

This application is a divisional of application Ser. No. 09/068,528 filed on May 13, 1998, now U.S. Pat. No. 6,821,756, which is 371 of PCT/JP97/03226 filed on Sep. 12, 1997.

TECHNICAL FIELD

This invention relates to a process for producing a complex carbohydrate which is useful for protection against infection of bacteria, viruses and the like, application to cardiovascular disorders and immunotherapy and to a process for producing a sugar nucleotide which is important as a substrate for the synthesis of the complex carbohydrate.

BACKGROUND ART

Examples of the known process for producing sugar nucleotides include: 1) chemical syntnetic processes (*Adv. carbohydr. Chem. Biochem.,* 28, 307 (1973), *Bull. Chem. Soc. Japan,* 46, 3275 (1973), *J. Org. Chem.,* 57, 146 (1992), *Carbohydr. Res.,* 242, 69 (1993)); 2) production processes using enzymes (*J. Org. Chem.,* 55, 1834 (1990), *J. Org. Chem.,* 57, 152 (1992), *J. Am. Chem. Soc.,* 110, 7159 (1988), Japanese Published Unexamined National Publication No. 508413/95, Japanese Published National Publication No. 500248/95, WO 96/27670); 3) processes using microbial cells such as yeast and the like (Japanese Published Examined Patent Application No. 2073/70, Japanese Published Examined Patent Application No. 40756/71, Japanese Published Examined Patent Application No. 1837/72, Japanese Published Examined Patent Application No. 26703/72, Japanese Published Examined Patent Application No. 8278/74, Japanese Published Unexamined Patent Application No. 268692/90); and 4) an extraction process from microbial cells of halotolerant yeast (Japanese Published Unexamined Patent Application No. 23993/96).

However, the process 1) requires expensive materials (for example, morpholidate derivative of nucleoside-5'-monophosphate (referred to as "NMP" hereinafter), sugar phosphate, etc.); the process 2) requires expensive materials (for example, nucleoside-5'-diphosphate (referred to as "NDP" hereinafter), nucleoside-5'-triphosphate (referred to as "NTP" hereinafter), phosphoenolpyruvate, etc.), and various enzymes (e.g., pyruvate kinase, etc.); and the process 3) requires drying treatment of microbial cells. Including the process 4), all of the above-mentioned processes use expensive nucleotides, sugar phosphates, and the like or have a difficulty in effecting large scale production from the operational point, of view, so that an industrial scale production process of sugar nucleotides has not so far been established.

Examples of the known process for producing complex carbohydrates include 1) chemical synthetic processes (*Method in Enzymol.,* 247, 193 (1994), *Angew. Chem. Int. Ed. Engl.,* 21, 155 (1982), *Carbohydr. Res.,* 211, cl (1991)), 2) processes in which a hydrolase is used (*Anal. Biochem.,* 202, 215 (1992), *Trends Biotechnol.,* 6, 256 (1988)) and 3) processes in which a glycosyltransferase is used (Japanese Published Unexamined Patent Application No. 79792/95, Japanese Published National Publication No. 500248/95, Japanese Published Examined Patent Application No. 82200/93, WO 94/25614, Japanese Published National Publication No. 503905/97, U.S. Pat. No. 5,583,042).

The introduction of protecting groups is essential for stereo-selective synthesis in the process 1). The yield and selectivity are not sufficient in the process 2). Expensive materials (for example, NDP, NTP, phosphoenolpyruvic acid, sugar phosphate, sugar nucleotide, etc.) and various enzymes (for example, pyruvate kinase, etc.) are necessary in the process 3). Therefore, these processes have not been established as inexpensive industrial production processes of complex carbohydrates. In addition, there has been nothing known about a process for the direct industrial production of complex carbohydrates, which uses only inexpensive nucleotide precursors, sugars and complex carbohydrate precursors as the starting materials.

It has been reported that UMP is produced in a microorganism belonging to the genus *Corynebacterium* when orotic acid is added (*Amino Acid, Nucleic Acid,* 23, 107 (1971)). In addition, a process in which cytidine diphosphate choline is formed from orotic acid as the material is also known (Japanese Published Unexamined Patent Application No. 276974/93).

DISCLOSURE OF THE INVENTION

An object of the present invention is to provide a process for producing a complex carbohydrate which is useful for protection against infection of bacteria, viruses, and the like, application to cardiovascular disorders and immunotherapy, and a process for producing a sugar nucleotide which is important as a substrate for synthesizing the complex carbohydrate at a low cost and efficiently.

The inventors of the present invention have conducted intensive studies on the microbial production of a complex carbohydrate and a sugar nucleotide using a nucleotide precursor as the starting material, and have found as the results that a sugar nucleotide can be produced by using only a nucleotide precursor and a sugar as the materials, that productivity of the sugar nucleotide can be improved by strengthening expression of genes involved in its biosynthesis and that a complex carbohydrate can be produced efficiently, using a microorganism capable of producing the sugar nucleotide and a microorganism, an animal cell or an insect cell capable of producing the complex carbohydrate from a sugar nucleotide and a complex carbohydrate precursor and using a nucleotide precursor, a sugar and a complex carbohydrate precursor as the only starting materials, thereby resulting in the accomplishment of the present invention.

The present invention provides a process for producing a complex carbohydrate, which comprises: selecting, as enzyme sources, a) a culture broth of a microorganism capable of producing NTP from a nucleotide precursor, or a treated product of the culture broth, b) a culture broth of a microorganism capable of producing a sugar nucleotide from a sugar and NTP, or a treated product of the culture broth, and c) a culture broth of a microorganism, an animal cell or an insect cell capable of producing a complex carbohydrate from a sugar nucleotide and a complex carbohydrate precursor, or a treated product of the culture broth; allowing the enzyme sources, the nucleotide precursor, the sugar and the complex carbohydrate precursor to be present in an aqueous medium to form and accumulate the complex carbohydrate in the aqueous medium; and recovering the complex carbohydrate from the aqueous medium, a process for producing a sugar nucleotide, which comprises: selecting, as enzyme sources, a) a culture broth of a microorganism capable of producing NTP from a nucleotide precursor, or a treated product of the culture broth, and b) a culture broth of a microorganism capable of producing a sugar nucleotide from a sugar and NTP, or a treated product of the culture broth; allowing the enzyme sources, the nucleotide precursor and the sugar to be present in an aqueous medium to form and accumulate the sugar nucleotide in the aqueous medium; and recovering the sugar nucleotide from the aqueous medium, and a process for producing a complex carbohydrate, which comprises: selecting, as an enzyme source, a culture bloth of a microorganism, an animal cell or an insect cell capable of producing a complex carbohydrate from a sugar nucleotide and a complex carbohydrate precursor, or a treated product of the culture broth; allowing the enzyme source, the sugar nucleotide obtained by the above-described process for producing a sugar nucleotide and the complex carbohydrate precursor to be present in an aqueous medium to form and accumulate the complex carbohydrate in the aqueous medium; and recovering the complex carbohydrate from the aqueous medium. It also provides a process for producing N-acetylglucosamine-1-phosphate, which comprises selecting, as an enzyme source, a culture broth of a microorganism having strong galactokinase activity, or a treated product of the culture broth; allowing the enzyme source and N-acetylglucosamine to be present in an aqueous medium to form and accumulate N-acetylglucosamine-1-phosphate in the aqueous medium; and recovering the N-acetylglucosamine 1-phosphate from the aqueous medium.

Figure 1:
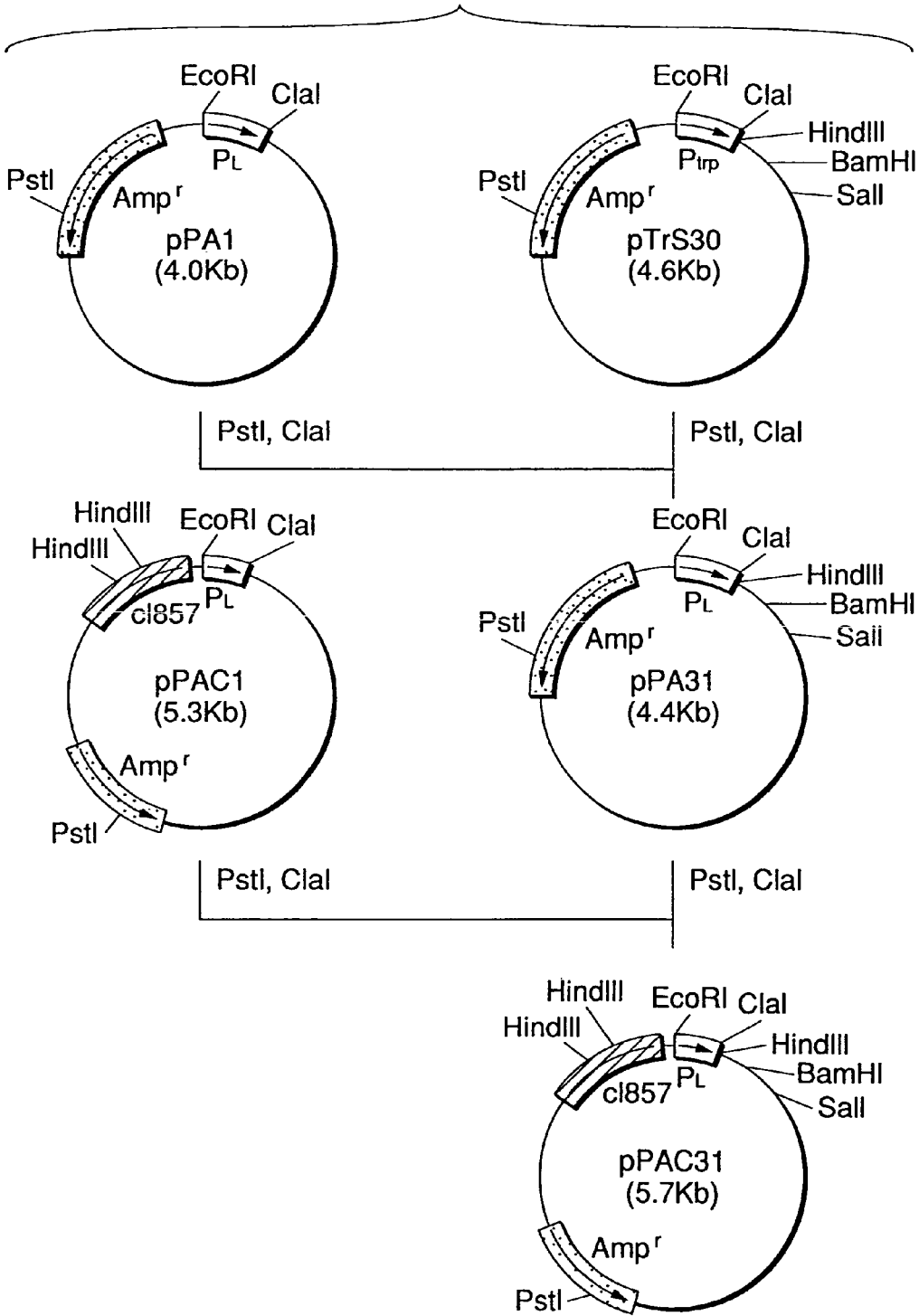
FIG. 1 shows construction steps of expression plasmids pPA31 and pPAC31.

Abbreviations to be used herein and description of the abbreviations are shown in Table 1-(1) and Table 1-(2).

TABLE 1-(1)

| Glc | glucose |
| G-6-P | glucose-6-phosphate |

TABLE 1-(1)-continued

| G-1-P | glucose-1-phosphate |
| Glc-1,6-P2 | glucose-1,6-diphosphate |
| Gal | galactose |
| Gal-1-P | galactose-1-phosphate |
| GlcN-6-P | glucosamine-6-phosphate |
| GlcN-1-P | glucosamine-1-phosphate |
| GlcUA | glucuronic acid |
| GlcN | glucosamine |
| GlcNAc | N-acetylglucosamine |
| GlcNAc-1-P | N-acetylglucosamine-1-phosphate |
| F-6-P | fructose-6-phosphate |
| F-1,6-P2 | fructose-1,6-diphosphate |
| Man | mannose |
| Man-6-P | mannose-6-phosphate |
| Man-1-P | mannose-1-phosphate |
| GDP-4-keto-6-deoxyMan | guanosine-5'-diphospho-4-keto-6-deoxymannose |
| ManNAc | N-acetylmannosamine |
| NeuAc | N-acetylneuraminic acid |
| acetyl CoA | acetyl coenzyme A |
| NTP | nucleoside-5'-triphosphate |
| NDP | nucleoside-5'-diphosphate |
| NMP | nucleoside-5'-monophosphate |
| ATP | adenosine-5'-triphosphate |
| UTP | uridine-5'-triphosphate |
| GTP | guanosine-5'-triphosphate |
| CTP | cytidine-5'-triphosphate |
| GMP | guanosine-5'-monophosphate |

TABLE 1-(2)

| UDP-Glc | uridine-5'-diphosphoglucose |
| UDP-Gal | uridine-5'-diphosphogalactose |
| UDP-GlcNAc | uridine-5'-diphospho-N-acetylglucosamine |
| UDP-GalNAc | uridine-5'-diphospho-N-acetylgalactosamine |
| UDP-GlcUA | uridine-5'-diphosphoglucuronic acid |
| GDP-Man | guanosine-5'-diphosphomannose |
| GDP-Fuc | guanosine-5'-diphosphofucose |
| CMP-NeuAc | cytidine-5'-monophospho-N-acetylneuraminic acid |
| galU | glucose-1-phosphate uridyltransferase |
| ppa | (inorganic) pyrophosphatase |
| galK | galactokinase |
| galT | galactose-1-phosphate uridyltransferase |
| glmU | N-acetylglucosamine-1-phosphate uridyltransferase glucosamine-1-phosphate acetyltransferase |
| pgm | phosphoglucomutase |
| pfkB | phosphofructokinase |
| glmM | phosphoglucosamine mutase |
| glk | glucokinase |
| manB | phosphomannomutase |
| manC | mannose-1-phosphate guanyltransferase |
| gmd | GDP-mannose-4,6-dehydratase |
| wcaG | GDP-4-keto-6-deoxymannose epimerase/reductase |
| neuA | CMP-N-acetylneuraminic acid synthetase |
| neuB | N-acetylneuraminic acid synthase |
| nanA | N-acetylneuraminic acid aldolase |
| pyrG | cytidine-5'-triphosphate synthetase |
| lgtB | β1,4-galactosyltransferase |
| lgtC | α1,4-galactosyltransferase |
| ugd | UDP-glucose dehydrogenase |

According to the present invention, a novel production process of a sugar nucleotide and a novel production process of a complex carbohydrate using the sugar nucleotide production process can be provided, which are characterized in that 1) expensive materials (for example, NTP, sugar phosphates, etc.) are not required, and inexpensive nucleotide precursor and a sugar can be used as the sole starting materials, 2) addition of expensive phosphoenolpyruvic acid and pyruvate kinase is not necessary in converting NMP or NDP into NTP, and 3) a process for the isolation of enzymes is not necessary.

With regard to the sugar nucleotide to be produced by the production process of the present invention, compounds having a general structure in which the terminal phosphate group of a nucleoside-5'-diphosphate residue and the reducing group of a sugar residue are linked together by ester bonding can be exemplified, and those compounds in which the nucleotide residue is cytidine-5'-monophosphate and the sugar residue is a polyol are also included in the sugar nucleotide to be produced by the present invention.

Examples of the complex carbohydrate to be produced by the production process of the present invention include compounds in which carbohydrates are bound to monosaccharides, oligosaccharides, monosaccharides or oligosaccharides linked to a carrier or the like, proteins, peptides, lipids, glycoproteins, glycolipids, glycopeptides, steroid compounds or the like.

The present invention will be described in detail below.

1) With regard to the microorganism for use in the present invention capable of producing NTP from a nucleotide precursor, any microorganism capable of producing NTP from a nucleotide precursor can be used. Examples include microorganisms belonging to the genus *Escherichia* and the genus *Corynebacterium*.

The microorganisms belonging to the genus *Escherichia* include *Escherichia coli* and the like.

The microorganisms belonging to the genus *Corynebacterium* include *Corynebacterium ammoniagenes* and the like.

2) As the microorganism for use in the present invention capable of producing a sugar nucleotide from a sugar and NTP, any microorganism having the activity to form the sugar nucleotide of interest can be used as follows.

2)-(i) With regard to the production of UDP-Glc, it is preferred to use a microorganism having strong enzyme activities of (1) to (4) shown in the following formula 1.

Specifically, microorganisms belonging to the genus *Escherichia* and the genus *Corynebacterium* can be exemplified. Specific examples include *Escherichia coli* and *Corynebacterium ammoniagenes*.

In addition, a transformant in which at least one of the enzyme activities selected from (1), (2), (3) and (4) are increased by recombinant DNA techniques can also be used. Specific examples of the transformant include *Escherichia coli* KY8415 (FERM BP-408) having recombinant DNA (pNT12) which contains galU and ppa genes derived from *Escherichia coli*, and the like.

(Formula 1)

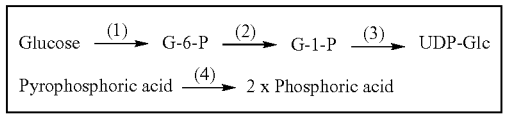

(1): Hexokinase (EC 2.7.1.1) or glucokinase (EC 2.7.1.2)

(2): Phosphoglucomutase (EC 2.7.5.1)

(3): Glucose-1-phosphate uridyltransferase (EC 2.7.7.9)

(4): (Inorganic) pyrophosphatase (EC 3.6.1.1)

2)-(ii) With regard to the production of UDP-Gal, it is preferred to use a microorganism having strong enzyme activities of (5) and (6) shown in the following formula 2, preferably further having strong enzyme activities of (1) to (4) shown in the above-mentioned formula 1.

Specifically, microorganisms belonging to the genus *Escherichia* and the genus *Corynebacterium* can be exemplified. Specific examples include *Escherichia coli* and *Corynebacterium ammoniagenes*.

In addition, a transformant in which at least one of the enzyme activities selected from (5) and (6), or at least one of the enzyme activities selected from (5) and (6) and at least one of the enzyme activities selected from (1) to (4), are increased by recombinant DNA techniques can also be used. Specific examples of the transformant include *Escherichia coli* NM522 having recombinant DNA (pNT25) which contains galT and gaLK genes derived from *Escherichia coli* and *Corynebacterium ammoniagenes* ATCC 21170 having recombinant DNA (pTK7) which contains galT and galK genes derived from *Escherichia coli*.

(Formula 2)

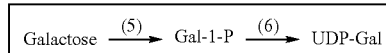

(5): Galactokinase (EC 2.7.1.6)

(6): Galactose-1-phosphate uridyltransferase (EC 2.7.7.12)

2)-(iii) With regard to the production of UDP-GlcNAc, it is preferred to use a microorganism having strong enzyme activities of (7) to (12) shown in the following formula 3 and having a strong enzyme activity of (4) shown in formula 1, or a microorganism having strong enzyme activities of (13) and (10) shown in formula 3.

Specifically, microorganisms belonging to the genus *Escherichia* and the genus *Corynebacterium* can be exemplified. Specific examples include *Escherichia coli* and *Corynebacterium anmoniagenes*.

In addition, a transformant in which at least one of the enzyme activities selected from (4), (7), (8), (9), (10) and (13) are increased by recombinant DNA techniques can also be used. Specific examples of the transformant include *Escherichia coli* NM522 having recombinant DNA (pNT44) which contains galmM gene derived from *Escherichia coli*, *Escherichia coli* KY8415 having recombinant DNA (pNT14) which contains glmU and ppa genes derived from *Escherichia coli*, *Escherichia coli* NM522 having recombinant DNA (pNT46) which contains glk gene derived from *Escherichia coli*, *Escherichia coli* NM522 having recombinant DNA (pNT54) which contains galK gene derived from *Escherichia coli*, and the like.

Although it is necessary to add Glc-1,6-P2 for the expression and increment of the phosphoglucosamine mutase activity of (8) (*J. Biol. Chem.*, 271, 32 (1996)), it is possible to provide Glc-1,6-P2 from G-6-P and F-6-P without adding Glc-1,6-P2 by using a transformant in which the enzyme activities of (11) and (12) are increased by recombinant DNA techniques.

Specific examples of such a transformant include *Escherichia coli* NM522 having recombinant DNA (pNT24) which contains pgm gene derived from *Escherichia coli*, *Escherichia coli* NM522 having recombinant DNA (pNT47) which contains pfkB gene derived from *Escherichia coli*, *Escherichia coli* NM522 having recombinant DNA (pNT55) which contains pgm and pfkB gene derived from *Escherichia coli*, and the like.

The process in which expression of the phosphoglucosamine mutase activity of (8) is increased by providing Glc-1,6-P2 from G-6-P and F-6-P using the enzyme activities of (11) and (12) is a process disclosed for the first time by the present invention.

The process in which GlcNAc-1-P is produced from GlcNAc using the galactokinase (EC 2.7.1.6) of (13) is a process disclosed for the first time by the present invention. It is possible to produce GlcNAc-1-P by using the process. That is, GlcNAc-1-P can be produced by using a culture broth or a treated product of the culture broth of a microorganism having strong galactokinase activity, such as a microorganism which contains recombinant DNA consisting of a DNA fragment containing a galK-encoding gene and a vector, as an enzyme source, allowing the enzyme source and GlcNAc to be present in an aqueous medium to form and accumulate GlcNAc-1-P in the aqueous medium, and recovering the thus-obtained GlcNAc-1-P from the aqueous medium.

Recovery of GlcNAc-1-P from the aqueous medium can be carried out in the usual way in which activated carbon, an ion exchange resin, and the like are used.

(Formula 3)

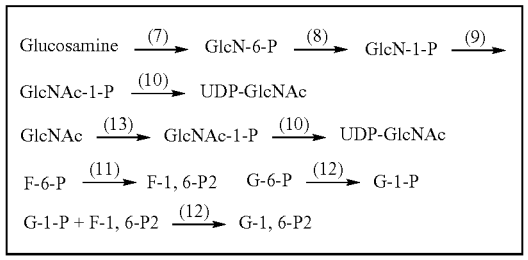

(7): Hexokinase (EC 2.7.1.1) or glucokinase (EC 2.7.1.2)

(8): Phosphoglucosamine mutase (9): Glucosamine-1-phosphate acetyltransferase (10): N-Acetylglucosamine-1-phosphate uridyltransferase (EC 2.7.7.23)

(11): Phosphofructokinase (EC 2.7.1.11)

(12): Phosphoglucomutase (EC 2.7.5.1)

(13): Galactokinase (EC 2.7.1.6)

2)-(iv) With regard to the production of UDP-GalNAc, it is preferred to use a microorganism having strong enzyme activities of (7) to (12) shown in formula 3, of (14) shown in formula 4 and of (4) shown in formula 1, or a microorganism having strong enzyme activities of (10) and (13) shown in formula 4 and of (14) shown in formula 4.

Specifically, microorganisms belonging to the genus *Escherichia* and the genus *Corynebacterium* can be exemplified. Specific examples include *Escherichia coli* and *Corynebacterium ammoniagenes*.

In addition, a transformant in which at least one of the enzyme activities selected from (7) to (14) and (4) are increased by recombinant DNA techniques can also be used.

(Formula 4)

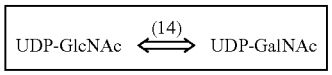

(14): UDP-GlcNAc 4-epimerase (EC 5.1.3.7)

2)-(v) With regard to the production of UDP-GlcUA, it is preferred to use a microorganism having strong enzyme activities of (1) to (4) shown in formula 1 and of (15) shown in formula 5.

Specifically, microorganisms belonging to the genus *Escherichia* and the genus *Corynebacterium* can be exemplified. Specific examples include *Escherichia coli* and *Corynebacterium ammoniagenes*.

In addition, a transformant in which at least one of the enzyme activities selected from (1), (2), (3), (4) and (15) are increased by recombinant DNA techniques can also be used.

(Formula 5)

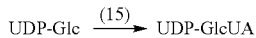

(15): UDP-Glc dehydrogenase (EC 1.1.1.22)

2)-(vi) With regard to the production of GDP-Man, it is preferred to use a microorganism having strong enzyme activities of (16) to (18) shown in the following formula 6 and of (11) and (12) shown in formula 3.

Specifically, microorganisms belonging to the genus *Escherichia* and the genus *Corynebacterium* can be exemplified. Specific examples include *Escherichia coli* and *Corynebacterium ammoniagenes*.

In addition, a transformant in which at least one of the enzyme activities selected from (16), (17) and (18) are increased by recombinant DNA techniques can also be used. Specific examples of the transformant include *Escherichia coli* NM522 having recombinant DNA (pNK7) which contains manB and manC genes derived from *Escherichia coli*, *Escherichia coli* NM522 having recombinant DNA (pNT46) which contains glk gene derived from *Escherichia coli*, and the like.

Although it is necessary to add Glc-1,6-P2 for the expression and increment of the phosphomannomutase activity of (17) by recombinant DNA techniques, it is possible to provide Glc-1,6-P2 from G-6-P and F-6-P without adding Glc-1,6-P2 by using a transformant in which the enzyme activities of (11) and (12) are increased by recombinant DNA techniques. Specific examples of such a transformant include *Escherichia coli* NM522 having recombinant DNA (pNT24) which contains pgm gene derived from *Escherichia coli*, *Escherichia coli* NM522 having recombinant DNA (pNT47) which contains pfkB gene derived from *Escherichia coli*, *Escherichia coli* NM522 having recombinant DNA (pNT55) which contains pgm and pfkB genes derived from *Escherichia coli*, and the like.

The process in which expression of the phosphomannomutase activity of (17) is increased by providing Glc-1,6-P2 from G-6-P and F-6-P using the enzyme activities of (11) and (12) is a process disclosed for the first time by the present invention.

(Formula 6)

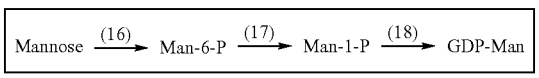

(16): Hexokinase (EC 2.7.1.1) or glucokinase (EC 2.7.1.2)

(17): Phosphomannomutase (EC 2.7.5.7)

(18): Mannose-1-phosphate guanyltransferase (EC 2.7.7.13)

2)-(vii) With regard to the production of GDP-Fuc, it is preferred to use a microorganism having strong enzyme activities of (19) and (20) shown in the following formula 7, of (16) to (18) shown in formula 6 and of (11) and (12) shown in formula 3.

Specifically, microorganisms belonging to the genus *Escherichia* and the genus *Corynebacterium* can be exemplified. Specific examples include *Escherichia coli* and *Corynebacterium ammoniagenes*.

In addition, a transformant in which at least one of the enzyme activities selected from (16), (17), (18), (19) and (20) are increased by recombinant DNA techniques can also be used. Specific examples of the transformant include *Escherichia coli* NM522 having recombinant DNA (pNK7) which contains manB and manC genes derived from *Escherichia coli*, *Escherichia coli* NM522 having recombinant DNA (pNKB) which contains gmd and wcaG genes derived from *Escherichia coli*, *Escherichia coli* NM522 having recombinant DNA (pNT46) which contains glk gene derived from *Escherichia coli*, and the like.

Although it is necessary to add Glc-1,6-P2 for the expression and increment of the phosphomannomutase activity of (17) by recombinant DNA techniques, it is possible to provide Glc-1,6-P2 from G-6-P and F-6-P without adding Glc-1,6-P2 by using a transformant in which the enzyme activities of (11) and (12) are increased by recombinant DNA techniques.

Specific examples of such a transformant include *Escherichia coli* NM522 having recombinant DNA (pNT24) which contains pgm gene derived from *Escherichia coli*, *Escherichia coli* NM522 having recombinant DNA (pNT47) which contains pfkB gene derived from *Escherichia coli*, *Escherichia coli* NM522 having recombinant DNA (pNT55) which contains pgm and pfkB genes derived from *Escherichia coli*, and the like.

(Formula 7)

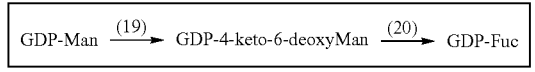

(19): GDP-Man-4, 6-dehydratase (EC 4.2.1.47)

(20): GDP-4-keto-6-deoxymannose epimerase/reductase

2)-(viii) With regard to the production of CMP-NeuAc, it is preferred to use a microorganism having strong enzyme activities of (21), (22) or (23), (24) and (25) shown in the following formula 8.

Specifically, microorganisms belonging to the genus *Escherichia* and the genus *Corynebacterium* can be exemplified. Specific examples include *Escherichia coli* and *Corynebacterium ammoniagenes*.

In addition, a transformant in which at least one of the enzyme activities selected from (21), (22), (23), (24) and (25) are increased by recombinant D techniques can also be used. Specific examples of the transformant include *Escherichia coli* C600 having recombinant DNA (pNAL1) which contains nanA gene derived from *Escherichia coli* (Appl. Environ. Macrobiol., 51, 562 (1986)), *Escherichia coli* NM522 having recombinant DNA (pTA14) which contains neuA gene derived from *Escherichia coli*, and the like.

(Formula 8)

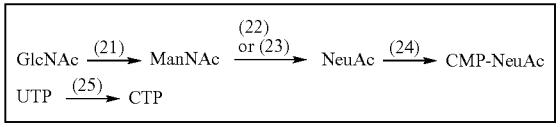

(21): GlcNAc 2-epimerase (EC 5.1.3.8)

(22): NeuAc aldolase (EC 4.1.3.3)

(23): NeuAc synthetase (EC 4.1.3.19)

(24): CMP-NeuAc synthetase (EC 2.7.7.43)

(25): CTP synthetase (EC 6.3.4.2)

When a microorganism has both of the properties of microorganisms described in 1) and the properties of microorganisms described in 2), it is possible to produce a sugar nucleotide from a nucleotide precursor and a sugar using the microorganism.

It is possible to produce UDP-Glc from a UTP precursor such as orotic acid or the like and glucose using a microorganism which has both of the properties of microorganisms described in 1) and the properties of microorganisms described in 2)-(i); UDP-Gal from a UTP precursor such as orotic acid or the like and galactose using a microorganism which has both of the properties of microorganisms described in 1) and the properties of microorganisms described in 2)-(ii); UDP-GlcNAc from a UTP precursor such as orotic acid or the like and glucosamine or N-acetylglucosamine using a microorganism which has both of the properties of microorganisms described in 1) and the properties of microorganisms described in 2)-(iii); UDP-GalNAc from a UTP precursor such as orotic acid or the like and glucosamine or N-acetylglucosamine using a microorganism which has both of the properties of microorganisms described in 1) and the properties of microorganisms described in 2)-(iv); UDP-GlcUA from a UTP precursor such as orotic acid or the like and glucose using a microorganism which has both of the properties of microorganisms described in 1) and the properties of microorganisms described in 2)-(v); GDP-Man from a GTP precursor such as GMP or the like and mannose using a microorganism which has both of the properties of microorganisms described in 1) and the properties of microorganisms described in 2)-(vi); GDP-Fuc from a GTP precursor such as GMP or the like and mannose using a microorganism which has both of the properties of microorganisms described in 1) and the properties of microorganisms described in 2)-(vii); and CMP-NeuAc from a CTP precursor such as orotic acid or the like and N-acetylglucosamine or N-acetylmannosamine using a microorganism which has both of the properties of microorganisms described in 1) and the properties of microorganisms described in 2)-(viii).

Specific examples of such microorganism include *Corynebacterium ammoniagenes* capable of expressing galT and galK genes derived from *Escherichia coli*.

Unlike the case of the above-mentioned strain, when a single strain has only a part of activities required for producing a sugar nucleotide, the sugar nucleotide can be produced by optionally combining microorganisms having respective activities.

The properties described in 1) are not necessarily owned by a single microorganism, and two or more microorganisms in which the properties described in 1) are independently located can also be used as the microorganism having the properties described in 1). Specifically, a combination of *Escherichia coli* capable of expressing *Escherichia coli*-derived pyrG gene with *Corynebacterium ammoniagenes* (Japanese Published Unexamined Patent Application No. 276974/93) is exemplified.

In the same manner, the microorganism having the properties described in 2) is not necessarily a single microorganism and the properties can independently be owned by two or more microorganisms. By optionally combining the microorganisms, each sugar nucleotide of interest can be produced.

For example, it is possible to produce UDP-Glc from a UTP precursor such as orotic acid or the like and glucose using a microorganism which has the properties of microorganism described in 1) and at least one microorganism having the properties described in 2)-(i); UDP-Gal from a UTP precursor such as orotic acid or the like and galactose using a microorganism which has the properties of microorganisms described in 1) and at least one microorganism having the properties described in 2)-(ii); UDP-GlcNAc from a UTP precursor such as orotic acid or the like and glucosamine or N-acetylglucosamine using a microorganism which has the properties of microorganisms described in 1) and at least one microorganism having the properties described in 2)-(iii); UDP-GalNAc from a UTP precursor such as orotic acid or the like and glucosamine or N-acetylglucosamine using a microorganism which has the properties of microorganisms described in 1) and at least one microorganism having the properties described in 2)-(iv); UDP-GlcUA from a UTP precursor such as orotic acid or the like and glucose using a microorganism which has the properties of microorganisms described in 1) and at least one microorganism having the properties described in 2)-(v); GDP-Man from a GTP precursor such as GMP or the like and mannose using a microorganism which has the properties described in 1) and at least one microorganism having the properties described in 2)-(vi); GDP-Fuc from a GTP precursor such as GMP or the like and mannose using a microorganism which has the properties described in 1) and at least one microorganism having the properties described in 2)-(vii); and CMP-NeuAc from a CTP precursor such as orotic acid or the like and N-acetylglucosamine or N-acetylmannosamine using a microorganism which has the properties described in 1) and at least one microorganism having the properties described in 2)-(viii).

As described in the foregoing, recombinant microorganisms can be used in the production of sugar nucleotides, and the genes shown in Table 2 related to the production of sugar nucleotides have been cloned from the chromosome of *Escherichia coli* and their complete nucleotide sequences have been determined.

TABLE 2

| Genes | References |
| --- | --- |
| galU gene | J. Biochem., 115, 965 (1994) |
| ppa gene | J. Bacteriol., 170, 5901 (1988) |
| galK gene | Nucleic Acids Res., 13, 1841 (1985) |
| galT gene | Nucleic Acids Res., 14, 7705 (1986) |
| glmU gene | J. Bacteriol., 175, 6150 (1993) |
| pgm gene | J. Bacteriol., 176, 5847 (1994) |
| pfkB gene | Gene, 28, 337 (1984) |
| glmM gene | J. Biol. Chem., 271, 32 (1996) |
| glk gene | J. Bacteriol., 179, 1298 (1997) |
| manB gene | J. Bacteriol., 178, 4885 (1996) |
| manC gene | J. Bacteriol., 178, 4885 (1996) |
| gmd gene | J. Bacteriol., 178, 4885 (1996) |
| wcaG gene | J. Bacteriol., 178, 4885 (1996) |
| neuA gene | J. Biol. Chem., 264, 14769 (1989) |
| neuB gene | J. Bacteriol., 177, 312 (1995) |
| nanA gene | Nucleic Acids Res., 13, 8843 (1985) |
| pyrG gene | J. Biol. Chem., 261, 5568 (1986) |
| ugd gene | J. Bacteriol., 177, 4562 (1995) |

Various procedures related to recombinant DNA techniques, such as isolation and purification of plasmid DNA from *Escherichia coli* having a plasmid which contains the genes, cleavage of the plasmid DNA with restriction enzymes, isolation and purification of the cleaved DNA fragments, enzymatic linking of the DNA fragments and transformation of *Escherichia coli* using recombinant DNA, can be carried out in accordance with known processes (for example, J. Sambrook et al., Molecular Cloning, A Laboratory Manual, second edition, Cold Spring Harbor Laboratory (1989)). In addition, the polymerase chain reaction (referred to as "PCR" hereinafter) can be carried out, for example, using Thermal Cycler manufactured by Perkin-Elmer-Cetus.

Expression of a gene related to the production of a sugar nucleotide in a host can be effected by a procedure in which a DNA fragment containing the gene is obtained as an appropriate length of DNA fragment containing the gene using restriction enzymes or PCR and then the thus formed DNA fragment is inserted into downstream of the promoter of an expression vector, and the DNA-inserted expression vector is introduced into a host cell which is suited for the expression vector.

Every microorganism can be used as the host, so long as it can express the gene of interest. Examples include microorganisms belonging to the genus *Escherichia, Serratia, Corynebacterium, Brevibacterium, Pseudomonas, Bacillus* and the like, as well as yeasts belonging to the genus *Saccharomyces, Candida* and the like.

With regard to the expression vector to be used, those having an ability to replicate autonomously in the above-described host or to be integrated into chromosome, and containing a promoter at the position at which transcription of the gene related to the production of a sugar nucleotide can be effected, may be used.

When the above-mentioned microorganism is used as the host, it is preferred that the expression vector of a gene related to the production of a sugar nucleotide can be replicated autonomously in the microorganism and that, at the same time, the expression vector comprises a promoter, a ribosome-binding sequence, the gene related to the production of sugar nucleotide and a transcription terminator sequence. It may also contain a regulatory gene of the promoter.

Examples of the expression vector include pBTrp2, pBTac1, pBTac2 (all manufactured by Boehringer Mannheim Co.), pKYP10 (Japanese Published Unexamined Patent Application No. 110600/83), pKYP200 (*Agric. Biol. Chum.*, 48, 669 (1984)), pLSA1 (*Agric. Biol. Chem.*, 53, 277 (1989)), pGEL1 (*Proc. Natl. Acad. Sci. USA.*, 82, 4306 (1985)), pBluescript II SK+ (manufactured by STRATAGENE), pTrS30 (prepared from *Escherichia coli* JM109/pTrS30 (FERM BP-5407)), pTrS32 (prepared from *Escherichia coli* JM109/pTrS32 (FERM BP-5408)), pUC19 (*Gene*, 33, 103 (1985)), pSTV28 (manufactured by Takara Shuzo Co., Ltd.), pPA1 (Japanese Published Unexamined Patent Application No. 233798/88), pCG11 (Japanese Examined Patent Application No. 91827/94), and the like.

Any promoter can be used, so long as it can be expressed in the above-mentioned host. Examples include promoters derived from *Escherichia coli*, phage and the like, such as trp promoter, lac promoter, $P_L$ promoter, $P_R$ promoter, and the like. Also usable are artificially designed and modified promoters such as trp tandem promoter in which two trp promoters are connected in series, tac promoter, and the like.

With regard to the ribosome-binding sequence, any sequence capable of being expressed in the above-mentioned host can be used, but it is preferred to use a plasmid in which the region between a ribosome-binding sequence and an initiation codon is adjusted to a suitable distance (for example, 6 to 18 bases).

Although the transcription terminator sequence is not always necessary for the expression of genes related to the production of sugar nucleotide, it is preferred to arrange the transcription termination sequence preferably at a downstream position of the structural gene.

Any microorganism can be used as the host, so long as it can express the recombinant DNA and can apply to the sugar nucleotide formation reaction. Examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* KY8415, *Escherichia coli* NM522, *Bacillus subtilis, Bacillus brevis,*

Bacillus amyloliquefaciens, Brevibacterium immariophilum ATCC 14068, Brevibacterium saccharolyticum ATCC 14066, Brevibacterium flavum ATCC 14067, Brevibacterium lactofermentum ATCC 13869, Corynebacterium ammoniagenes ATCC 21170, Corynebacterium glutamicus ATCC 13032, Corynebacterium acetoacidophilum ATCC 13870, Microbacterium ammoniaphilum ATCC 15354, Pseudomonas putida, Serratia marcescens, and the like.

When a yeast strain is used as the host, the expression vector may be YEp13 (ATCC 37115), YEp24 (ATCC 37051), YCp50 (ATCC 37419) or the like.

With regard to the promoter, any promoter capable of being expressed in the yeast strain host can be used. Examples include promoters in genes of the glycolytic pathway, such as hexokinase as well as other promoters such as gal 1 promoter, gal 10 promoter, heat shock protein promoter, MFα1 promoter and CUP 1 promoter.

With regard to the host, any yeast capable of expressing recombinant DNA and applying to the sugar nucleotide formation reaction can be used. Examples include Saccharomyces cerevisiae, Candida utilis, Candida parapsilosis, Candida krusei, Candida versatilis, Candida lipolytica, Candida zeylanoides, Candida guillermondii, Candida albicans, Candida humicola, Pichia farinosa, Pichia ohmeri, Torulopsis candida, Torulopsis sphaerica, Torulopsis xylinus, Torulapsis famata, Torulopsis versatilis, Debaryomyces subglobosus, Debaryomyces cantarellii, Debaryomyces globosus, Debaryomyces hansenii, Debaryomyces japonicus, Zygosaccharomyces rouxii, Zygosaccharcmyces bailii, Kluyveromyces lactis, Kluyveromyces marxianus, Hansenula anomala, Hansenula jadinii, Brettanomyces lambicus, Brettanomyces anomalus, Schizosaccharomyces pombe, Trichosporon pullulans, Schwanniomyces alluvius, and the like.

Culturing of the microorganism for use in the present invention can be carried out in accordance with the usual culturing process. The medium for use in the culturing of the microorganism may be either a nutrient medium or a synthetic medium, so long as it contains carbon sources, nitrogen sources, inorganic salts and the like which can be assimilated by the microorganism and it can perform culturing of the microorganism efficiently.

Examples of the carbon sources include those which can be assimilated by each microorganism, such as carbohydrates (for example, glucose, fructose, sucrose, lactose, maltose, mannitol, sorbitol, molasses, starch, starch hydrolysate, etc.), organic acids (for example, pyruvic acid, lactic acid, citric acid, fumaric acid, etc.), various amino acids (for example, glutamic acid, methionine, lysine, etc.), and alcohols (for example, ethanol, propanol, glycerol, etc.). Also useful are natural organic nutrient sources, such as rice bran, cassava, bagasse, corn steep liquor, and the like.

Examples of the nitrogen sources include various inorganic and organic ammonium salts (for example, ammonia, ammonium chloride, ammonium sulfate, ammonium carbonate, ammonium acetate, ammonium phosphate, etc.), amino acids (for example, glutamic acid, glutamine, methionine, etc.), peptone, NZ amine, corn steep liquor, meat extract, yeast extract, malt extract, casein hydrolysate, soybean meal, fish meal or a hydrolysate thereof and the like.

Examples of the inorganic substances include potassium dihydrogen phosphate, dipotassium hydrogen phosphate, sodium dihydrogen phosphate, disodium hydrogen phosphate, magnesium phosphate, magnesium sulfate, magnesium chloride, sodium chloride, calcium chloride, ferrous sulfate, manganese sulfate, copper sulfate, zinc sulfate, calcium carbonate, and the like. Vitamins, amino acids, nucleic acids and the like may be added as occasion demands.

The culturing is carried out under aerobic conditions by shaking culture, aeration stirring culture or the like means. The culturing temperature is preferably from 15 to 45° C., and the culturing time is generally from 5 to 96 hours. The pH of the medium is maintained at 3.0 to 9.0 during the culturing. Adjustment of the medium pH is carried out using an inorganic or organic acid, an alkali solution, urea, calcium carbonate, ammonia and the like. Also, antibiotics (for example, ampicillin, tetracycline, etc.) may be added to the medium during the culturing as occasion demands.

When a microorganism transformed with an expression vector in which an inducible promoter is used as the promoter is cultured, an inducer may be added to the medium as occasion demands. For example, isopropyl-β-D-thiogalactopyranoside (IPTG) or the like may be added to the medium when a microorganism transformed with an expression vector containing lac promoter is cultured, or indoleacrylic acid (IAA) or the like may by added thereto when a microorganism transformed with an expression vector containing trp promoter is cultured.

When two or more microorganisms are used in the sugar nucleotide production of the present invention, the microorganisms may be separately cultured to use the resulting culture broths in the sugar nucleotide production or inoculated simultaneously into a single culture vessel to carry out mixed culturing and to use the resulting culture broth in the sugar nucleotide production. In an alternative way, one of the microorganisms is firstly cultured, the remaining microorganism is inoculated during or after the culturing and cultured, and then the resulting culture broth is used in the sugar nucleotide production. In another alternative way, a microorganism having the properties described in 1) and a microorganism having the properties described in 2) may be separately cultured and used in the sugar nucleotide production using the resulting culture broths.

The microbial culture broth obtained by the culturing or a treated product of the culture broth obtained by treating the culture broth in various ways can be used as an enzyme source for the formation of a sugar nucleotide in an aqueous medium.

Examples of the treated product of the culture broth include a concentrated product of the culture broth, a dried product of the culture broth, a culture supernatant obtained by centrifuging the culture broth, a concentrated product of the culture supernatant, an enzyme preparation obtained from the culture supernatant, cells (including microbial cells) obtained by centrifuging the culture broth, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extraction from the cells.

The amount of the enzyme source used in the formation of the sugar nucleotide is within the range of from 1 to 500 g/l, preferably from 5 to 300 g/l, as wet cells. When the reaction is carried out in an aqueous medium using two or more microorganisms simultaneously, amount of the total wet cells of the microorganisms in the aqueous medium is within the range of from 2 to 500 g/l, preferably from 5 to 400 g/l.

Examples of the aqueous medium used in the formation of the sugar nucleotide include water, buffer solutions (for example, those of phosphate, carbonate, acetate, borate, citrate, Tris, etc.), alcohols (for example, methanol, ethanol, etc.), esters (for example, ethyl acetate, etc.), ketones (for example, acetone, etc.), amides (for example, acetamide, etc.), and the like. The microbial culture broth used as the enzyme source may also be used as the aqueous medium.

Examples of the nucleotide precursor used in the formation of the sugar nucleotide include orotic acid, uracil, orotidine, uridine, cytosine, cytidine, adenine, adenosine, guanine, guanosine, hypoxanthine, inosine, xanthine, xanthosine, inosine-5'-monophosphate, xanthosine-5'-monophosphate, guanosine-5'-monophosphate, uridine-5'-monophosphate, cytidine-5'-monophosphate, and the like. Preferred are orotic acid and guanosine-5'-monophosphate. The nucleotide precursor may be in the form of a purified product or in the form of a salt of the precursor, and a culture broth containing the precursor produced by the fermentation of a microorganism or the precursor roughly purified from the culture broth may also be used as the nucleotide precursor, so long as its impurities do not inhibit the reaction. The nucleotide precursor is used at a concentration of from 0.1 mM to 1.0 M, preferably from 0.01 to 0.3 M.

Examples of the sugar used in the formation of the sugar nucleotide include glucose, fructose, galactose, glucosamine, N-acetylglucosamine, N-acetylgalactosamine, mannose, fucose, N-acetylmannosamine, N-acetylneuraminic acid and the like, and derivatives thereof. The sugar may be either in the form of a purified product or in the form of a material containing the same, so long as impurities in the material do not inhibit the reaction. The sugar is used at a concentration of from 0.1 mM to 2.0 M, by adding it in one portion when the reaction is started or in portions or continuously during the reaction.

In the formation of the sugar nucleotide, an energy source necessary for the regeneration of ATP, a coenzyme, a phosphate ion, a magnesium ion, a chelating agent (for example, phytic acid, etc.), a surfactant and an organic solvent may be added as occasion demands.

Examples of the energy source include carbohydrate (for example, glucose, fructose, sucrose, lactose, maltose, mannitol, sorbitol, molasses, starch hydrolysate, etc.), organic acids (for example, pyruvic, lactic acid, acetic acid, etc.), amino acids (for example, glycine, alanine, aspartic acid, glutamic acid, etc.), and the like, which may be used at a concentration of from 1.0 mM to 2.0 M.

Examples of the phosphate ion include orthophosphoric acid, polyphosphoric acids (for example, pyrophosphoric acid, tripolyphosphoric acid, tetrapolyphosphoric acid, tetrapolymetaphosphoric acid, etc.), polymetaphosphoric acids, inorganic phosphates (for example, potassium dihydrogen phosphate, dipotassium hydrogen phosphate, sodium dihydrogen phosphate, disodium hydrogen phosphate, etc.), and the like, which may be used at a concentration of from 1.0 mM to 1.0 M.

Examples of the magnesium ion include inorganic magnesium salts (for example, magnesium sulfate, magnesium nitrate, magnesium chloride, etc.), organic magnesium salts (for example, magnesium citrate, etc.), and the like, which may be used at a concentration of generally from 1 to 100 mM.

Examples of the surfactant include those which can enhance the production of various sugar nucleotides, such as nonionic surfactants (for example, polyoxyethylene octadecylamine (e.g., seen S-215, manufactured by Nippon Oils and Fats Co.), etc.), cationic surfactants (for example, cetyl trimethylaimonium bromide, alkyldirmethyl benzylamonium chloride (e.g., Cation F2-40E, manufactured by Nippon Oils and Fats Co.) etc.), anionic surfactants (for example, lauroyl sarcosinate, etc.) and tertiary amines (for example, alkyldimethylamine (e.g., Tertiary Amine FB, manufactured by Nippon Oils and Fats Co.), etc.), which may be used alone or as a mixture of two or more. The surfactant may be used at a concentration of generally from 0.1 to 50 g/l.

Examples of the organic solvent include xylene, toluene, aliphatic alcohol, acetone, ethyl acetate, and the like, which may be used at a concentration of generally from 0.1 to 50 ml/l.

The reaction for forming a sugar nucleotide can be carried out in an aqueous medium at pH of from 5 to 10, preferably from 6 to 9, at a temperature of from 20 to 50° C. and for a period of from 2 to 96 hours.

The sugar nucleotide can be formed by the process. Examples include a uridine diphosphate compound, a guanosine diphosphate compound, a cytidine monophosphate compound and the like. Specific examples include sugar nucleotides selected from UDP-Glc, UDP-Gal, UDP-GlcNAc, UDP-GalNAc, UDP-GlcUA, GDP-Man, GDP-Fuc, CMP-NeuAc, and the like, and derivatives thereof.

Determination of the sugar nucleotide formed in the aqueous medium can be carried out in accordance with a known method, for example, isolation and determination of UDP-Glc and UDP-Gal can be carried out by high performance liquid chromatography (referred to as "HPLC" hereinafter) method described in *Anal. Biochem.*, 216, 188 (1994). In addition, isolation and determination of UDP-GlcNAc, GDP-Man, GDP-Fuc and CMP-NeuAc can be carried out by HPLC under the following conditions:

Elution solution:
  0.1 M $KH_2PO_4$ (adjust to pH 3.2 with $H_3PO_4$)
Flow rate:
  1 ml/min
Column:
  Partisil-10 SAX (manufactured by Whatman)
Detection:
  UV 262 nm
Determination:
  Calculated by comparing standard absorbance values Recovery of the sugar nucleotide formed in the reaction solution can be carried out in the usual way using activated carbon, an ion exchange resin and the like, for example, UDP-Gal and UDP-Glc can be recovered in accordance with the process described in *J. Org. Chem.*, 57, 152 (1992), and UDP-GlcNAc with the process described in *J. Org. Chem.*, 57, 146 (1992).

With regard to the microorganisms, animal cells or insect cells eligible for in the production of the complex carbohydrate of the present invention, all microorganisms, animal cells or insect cells capable of producing the complex carbohydrate from a sugar nucleotide and a complex carbohydrate precursor can be used. Examples of such microorganisms, animal cells or insect cells include those which have the activities of glucosyltransferase, galactosyltransferase, N-acetylglucosaminyltransferase, N-acetylgalactosaminyltransferase, glucuronosyltransferase, mannosyltransferase, sialyltransferase, fucosyltransferase, and the like.

In addition, microorganisms, animal cells or insect cells modified by recombinant DNA techniques can also be used in a similar way to the case of the above-mentioned sugar nucleotide production. Examples of such microorganisms, animal cells or insect cells include *Escherichia coli* which expresses the ceramide glucosyltransferase gene derived from human melanoma cell line SK-Mel-28 (*Proc. Natl. Acad. Sci. USA*, 93, 4638 (1996)), human melanoma cell line WM266-4 which produces β1,3-galactosyltransferase (ATCC CRL 1676), recombinant cell line such as namalwa cell line KJM-1 or the like which contains the β1,3-galactosyltransferase gene derived from the human melanoma cell line WM266-4 (Japanese Published Unexamined Patent Application No. 181759/

94), *Escherichia coli* (*EMBO J.*, 9, 3171 (1990)) or *Saccharomyces cerevisiae* (*Biochem, Biophys. Res. Commun.*, 201, 160 (1994)) which expresses the β1,4-galactosyltransferase gene derived from human HeLa cells, COS-7 cell line (ATCC CRL 1651) which expresses the rat β1,6-N-acetylglucosaminyltransferase gene (*J. Biol. Chem.*, 268, 15381 (1993)), Sf9 cell line which expresses human N-acetylglucosaminyltransferase gene (*J. Biochem.*, 118, 568 (1995)), *Escherichia coli* which expresses human glucuronosyltransferase (*Biochem. Biophys. Res. Commun.*, 196, 473 (1993)), namalwa cell line which expresses human α1,3-fucosyltransferase (*J. Biol. Chem.*, 269, 14730 (1994)), COS-1 cell line which expresses human α1,3/1,4-fucosyltransferase (Genes Dev., 4, 1288 (1990)), COS-1 cell line which expresses human α1,2-fucosyltransferase (*Proc. Natl. Acad. Sci. USA.*, 87, 6674 (1990)), COS-7 cell line which expresses chicken α2,6-sialyltransferase (*Eur. J. Biochem.*, 219, 375 (1994)), COS cell line which expresses human α2,8-sialyltransferase (*Proc. Nati. Acad. Sci. USA.*, 91, 7952 (1994)), *Escherichia coli* which expresses β1,3-N-acetylglucosaminyltransferase, β1,4-galactosyltransferase, β1,3-N-acetylgalactosaminyltransferase or α1,4-galactosyltransferase derived from *Neisseria* (WO 96/10086), *Escherichia coli* which expresses *Neisseria*-derived α2,3-sialyltransferase (*J. Biol. Chem.*, 271, 28271 (1996)), *Escherichia coli* which expresses *Helicobacter pylori*-derived α1,3-fucosyltransferase (*J. Biol. Chem* 272, 21349 and 21357 (1997)), *Escherichia coli* which expresses yeast-derived α1,2-mannosyltransferase (*J. Org. Chem.*, 58, 3985 (1993)), and the like.

When a microorganism is used for producing the complex carbohydrate of the present invention, the microorganism can be cultured using the same medium under the same culture conditions as in the case of the above-mentioned microorganism capable of producing a sugar nucleotide from a nucleotide precursor and a sugar.

When animal cells are used for producing the complex carbohydrate of the present invention, the preferred culture medium is generally RPMI 1640 medium, Eagle's MEM medium or a medium thereof modified by further adding fetal calf serum, and the like. The culturing is carried out under certain conditions, for example, in the presence of 5% $CO_2$. The culturing is carried out at a temperature of preferably from 20 to 40° C. for a period of generally from 3 to 14 days. As occasion demands, antibiotics may be added to the medium.

When insect cells are used for producing the complex carbohydrate of the present invention, culturing of the insect cells can be carried out in accordance with the known process (*J. Biol. Chem.*, 268, 12609 (1993)).

The culture broth of a microorganism, an animal cell line or an insect cell line obtained by the culturing and a treated product of the culture broth obtained by treating the culture broth in various ways can be used as an enzyme source for forming the complex carbohydrate in an aqueous medium.

Examples of the treated product of the culture broth include a concentrated product of the culture broth, a dried product of the culture broth, a culture supernatant obtained by centrifuging the culture broth, a concentrated product of the culture supernatant, an enzyme preparation obtained from the culture supernatant, cells (including microbial cells) obtained by centrifuging the culture broth, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extraction from the cells.

The enzyme source used in the formation of the complex carbohydrate is typically within the range of from 0.1 mU/l to 10,000 U/l, preferably from 1 mU/l to 1,000 U/l (where 1 unit (U) is the amount of the enzyme activity which can form 1 µmole of the complex carbohydrate within 1 minute at 37° C.).

Examples of the aqueous medium used in the formation of the complex carbohydrate include water, buffer solutions (for example, those of phosphate, carbonate, acetate, borate, citrate, Tris, etc.), alcohols (for example, methanol, ethanol, etc.), esters (for example, ethyl acetate, etc.), ketones (for example, acetone, etc.), amides (for example, acetamide, etc.), and the like. Each of the culture broths of microorganisms, animal cells or insect cells used as the enzyme sources may also be used as the aqueous medium.

As occasion demands, chelating agents (for example, phytic acid, etc.), inorganic salts (for example, $MnCl_2$, etc.), β-mercaptoethanol and the like may be added.

As the sugar nucleotide used in the formation of the complex carbohydrate, the above-mentioned reaction solution obtained by the sugar nucleotide formation or the sugar nucleotide purified from the reaction solution can be used at a concentration of from 0.01 mM to 2.0 M.

In addition, a sugar nucleotide can be supplied in the complex carbohydrate formation reaction solution by forming the sugar nucleotide by the above-mentioned process.

With regard to the complex carbohydrate precursor used in the formation of the complex carbohydrate, any material can be used, so long as it can be used as the substrate of glycosyltransferase. Examples include monosaccharides, oligosaccharides, monosaccharides or oligosaccharides linked to a carrier or the like, proteins, peptides, lipids, glycoproteins, glycolipids, glycopeptides, steroid compounds, and the like.

Specific examples include glucose, galactose, mannose, sialic acid, N-acetylglucosamine, N-acetylgalactosamine, lactose, N-acetyllactosamine, lacto-N-biose, GlcNAcβ1-3Galβ1-4Glc, GlcNAcβ1-4Galβ1-4-glc, globotriose, Galα1-4Galβ1-4GlcNAc,2'-fucosyllactose, 3-fucosyllactose, 3'-sialyllactose, 6'-sialyllactose, 3'-sialyl-N-acetyllactosamine, 6'-sialyl-N-acetyllactosamine, sialyllacto-N-biose, Lewis X, Lewis a, lacto-N-tetraose, lacto-N-neotetraose, lactodifucotetraose, 3'-sialyl-3-fucosyllactose, sialyl-Lewis X, sialyl-Lewis a, lacto-N-fucopentaose I, lacto-N-fucopentaose II, lacto-N-fucopentaose III, lacto-N-fucopentaose V, LS-tetrasaccharide a, LS-tetrasaccharide b, LS-tetrasaccharide c, 3' sialyllacto-N-neotetraose and derivatives thereof, serine, threonine, asparagine and peptides containing these amino acids and derivatives thereof, ceramide and derivatives thereof, and the like. The complex carbohydrate precursor can be used at a concentration of from 0.01 mM to 2.0 M.

Examples of the complex carbohydrate of the present invention include complex carbohydrates containing at least one sugar selected from glucose, galactose, N-acetylglucosamine, N-acetylgalactosamine, glucuronic acid, mannose, N-acetylmannosamine, fucose, sialic acid, lactose, N-acetyllactosamine, lacto-N-biose, GlcNAcβ1-3Galβ1-4Glc, GlcNAcβ1-4Galβ1-4Glc, globotriose, Galα1-4Galβ1-4GlcNAc, 2'-fucosyllactose, 3-fucosyllactose, 3'-sialyllactose, 6'-sialyllactose, 3'-sialyl-N-acetyllactosamine, 6'-sialyl-N-acetyllactosamine, sialyllacto-N-biose, Lewis X, Lewis a, lacto-N-tetraose, lacto-N-neotetraose, lactodifucotetraose, 3'-sialyl-3-fucosyllactose, sialyl-Lewis X, sialyl-Lewis a, lacto-N-fucopentaose I, lacto-N-fucopentaose II, lacto-N-fucopentaose III, lacto-N-fucopentaose V, LS-tetrasaccharide a, LS-tetrasaccharide b, LS-tetrasaccharide C, (α2,3)sialyllacto-N-neotetraose, lacto-N-difucohexaose I, lacto-N-difucohexaose II, lacto-N-hexaose, lacto-N-neohexaose, disialyllacto-N-tetraose and derivatives thereof; and complex carbohydrates which contain the just described complex carbohydrates. Specifically, they include complex carbohydrates which contain a sugar having a bond selected from Galβ1-3Glc, Galβ1-4Glc, Galβ1-3GlcNAc, Galβ1-4GlcNAc, Galβ1-3Gal, Galβ1-4Gal, Galβ1-3GalNAc, Galβ1-4GalNAc, Galβ1-3Glc, Galα1-4Glc, Galα1-3GlcNAc, Galα1-4GlcNAc, Galα1-3Gal, Galα1-4Gal, Galα1-3GalNAc, Galα1-4GalNAc, GlcNAcβ1-3Gal, GlcNAcβ1-4Gal, GlcNAcβ1-6Gal, GlcNAcβ1-3Glc, GlcNAcβ1-4Glc, GlcNAcβ4-1-3GlcNAc, GlcNAcβ1-4GlcNAc, GlcNAcβ1-6GalNAc, GlcNAcβ1-2Man, GlcNAcβ1-4Man, GlcNAc1-6Man, GalNAcβ1-3Gal, GalNAcβ1-4Gal, GalNAcβ1-4GlcNAc, GalNAcα1-3GalNAc, Manβ1-4GlcNAc, Manα1-6Man, Manα1-3Man, Manα1-2Man, GlcUAβ1-4GlcN, GlcUAβ1-3Gal, GlcUAβ1-3GlcNAc, GlcUAβ1-3GalNAc, NeuAcα2-3Gal, NeuAcα2-6Gal, NeuAcα2-3GlcNAc, NeuAcα2-6GlcNAc, NeuAcα2-3GalNAc, NeuAcα2-6GalNAc, NeuAcα2-8Neuc, Fucα1-3Glc, Fucα1-4Glc, Fucα1-3GlcNAc, Fucα1-4GlcNAc, Fucα1-2Gal and Fucα1-6GlcNAc; and complex carbohydrates which contain the just described complex carbohydrates. In this case, the number of sugars contained in the complex carbohydrate having the sugars may be 10 or below, or 6 or below.

As specific processes for producing the complex carbohydrates, (1) lactose can be formed from orotic acid, galactose and glucose by carrying out an enzyme reaction using culture broths of a microorganism having the ability to express *Neisseria*-derived β1,4-galactosyltransferase (WO 96/10086), a microorganism having the ability to produce UTP from a precursor of UTP and a microorganism having the ability to produce UDP-Gal from a sugar and UTP, or treated products of these culture broths, as enzyme sources, (2) N-acetyllactosamine can be formed from orotic acid, galactose and N-acetylglucosamine by carrying out an enzyme reaction using culture broths of a microorganism having the ability to express *Neisseria*-derived β1,4-galactosyltransferase (WO 96/10086), a microorganism having the ability to produce UTP from a precursor of UTP and a microorganism having the ability to produce UDP-Gal from a sugar and UTP, or treated products of these culture broths, as enzyme sources, (3) 3'-sialyllactose can be formed from orotic acid, N-acetylmannosaiine, pyruvic acid and lactose by carrying out an enzyme reaction using culture broths of a microorganism having the ability to express *Neisseria*-derived α2,3-sialyltransferase (*J. Biol. Chem.*, 271, 28271 (1996)), a microorganism having the ability to produce CTP from a precursor of CTP and a microorganism having the ability to produce CMP-NeuAc from a sugar and CTP, or treated products of these culture broths, as enzyme sources, (4) 3'-sialyl-N-acetyllactosamine can be formed from orotic acid, N-acetylmannosamine, pyruvic acid and N-acetyllactosamine by carrying out an enzyme reaction using culture broths of a microorganism having the ability to express *Neisseria*-derived (α2,3-sialyltransferase (*J. Biol. Chem.*, 271, 28271 (1996)), a microorganism having the ability to produce CTP from a precursor of CTP and a microorganism having the ability to produce CMP-NeuAc from a sugar and CTP, or treated products of these culture broths, as enzyme sources, (5) 6'-sialyl-N-acetyllactosamine can be formed from orotic acid, N-acetylmannosamine, pyruvic acid and N-acetyllactosamine by carrying out an enzyme reaction using culture broths of COS-7 cell line having the ability to express chicken-derived α2,6-sialyltransferase (*Eur. J. Biochem.*, 219, 375 (1994)), a microorganism having the ability to produce CTP from a precursor of CTP and a microorganism having the ability to produce CMP-NeuAc from a sugar and CTP, or treated products of these culture broths, as enzyme sources, (6) GlcNAcβ1-3Galβ1-4Glc can be formed from orotic acid, N-acetylglucosamine and lactose by carrying out an enzyme reaction using culture broths of a microorganism having the ability to express *Neisseria*-derived β1,3-N-acetylglucosaminyltransferase (WO 96/10086), a microorganism having the ability to produce UTP from a precursor of UTP and a microorganism having the ability to produce UDP-GlcNAc from a sugar and UTP, or treated products of these culture broths, as enzyme sources, (7) lacto-N-tetraose can be formed from orotic acid, galactose and GlcNAcβ1-3Galβ1-4Glc by carrying out an enzyme reaction using culture broths of human melanoma cell line WM266-4 having the ability to produce β1,3-galactosyltransferase (ATCC CRL 1676) or a transformant such as of namalwa cell line KJM-1 having the ability to express β1,3-galactosyltransferase gene derived from human melanoma cell line WM266-4 (Japanese Published Unexamined Patent Application No. 181759/94), a microorganism having the ability to produce UTP from a precursor of UTP and a microorganism having the ability to produce UDP-Gal from a sugar and UTP, or treated products of these culture broths, as enzyme sources, (8) lacto-N-neotetraose can be formed from orotic acid, galactose and GlcNAβ1-3Galβ1-4Glc by carrying out an enzyme reaction using culture broths of *Escherichia coli* (*EMBO J.*, 9, 3171 (1990)) or *Saccharzcyces cerevisiae* (*Biochem. Bicphys. Res. Commun.*, 201, 160 (1994)) having the ability to express β1,4-galactosyltransferase gene derived from human HeLa cell line, a microorganism having the ability to produce UTP from a precursor of UTP and a microorganism having the ability to produce UDP-Gal from a sugar and UTP, or treated products of these culture broths, as enzyme sources, (9) lacto-N-neotetraose can be formed from orotic acid, galactose and GlcNAcβ1-3Galβ1-4Glc by carrying out an enzyme reaction using culture broths of a microorganism having the ability to express *Neisseria*-derived β1,4-galactosyltransferase (WO 96/10086), a microorganism having the ability to produce UTP from a precursor of UTP and a microorganism having the ability to produce UDP-Gal from a sugar and UTP, or treated products of these culture broths, as enzyme sources,

(10) lacto-N-neotetraose can be formed from orotic acid, N-acetylglucosamine, galactose and lactose by carrying out an enzyme reaction using culture broths of a microorganism which can express *Neisseria*-derived β1,3-N-acetylglucosaminyltransferase (WO 96/10086), a microorganism having the ability to express *Neisseria*-derived β1,4-galactosyltransferase (WO 96/10086), a microorganism having the ability to produce UTP from a precursor of UTP, a microorganism having the ability to produce UDP-GlcNc from a sugar and UTP and a microorganism having the ability to produce UDP-Gal from a sugar and UTP, or treated products of these culture broths, as enzyme sources,

(11) 3' sialyllacto-N-neotetraose can be formed from orotic acid, N-acetylmannosamine, pyruvic acid and lacto-N-neotetraose by carrying out an enzyme reaction using culture broths of a microorganism having the ability to express *Neisseria*-derived α2,3-sialyltransferase (*J. Biol. Chem.*, 271, 28271 (1996)), a microorganism having the ability to produce CTP from a precursot of CTP and a microorganism having the ability to product CMP-NeuAc from a sugar and CTP, or treated products of these culture broths, as enzyme sources,

(12) lacto-N-fucopentaose III can be formed from GMP, mannose and lacto-N-neotetraose by carrying out an enzyme reaction using culture broths of namalwa cell line having the ability to express human-derived α1,3-fucosyltransferase (*J. Biol. Chem.*, 269, 14730 (1994)), a microorganism having the ability to produce GTP from a precursor of GTP and a microorganism having the ability to produce GDP-Fuc from a sugar and GTP, or treated products of these culture broths, as enzyme sources,

(13) lacto-N-fucopentaose III can be formed from GMP, mannose and lacto-N-neotetraose by carrying out an enzyme reaction using culture broths of a microorganism having the ability to express *Helicobacter pylori*-derived α1,3-fucosyltransferase (*J. Biol. Chem.*, 272, 21349 and 21357 (1997)), a microorganism having the ability to produce GTP from a precursor of GTP and a microorganism having the ability to produce GDP-Fuc from a sugar and GTP, or treated products of these culture broths, as enzyme sources;

(14) globotriose can be formed from orotic acid, galactose and lactose by carrying out an enzyme reaction using culture broths of a microorganism having the ability to express *Neisseria*-derived α1,4-galactosyltransferase (WO 96/10086), a microorganism having the ability to produce UTP from a precursor of UTP and a microorganism having the ability to produce UDP-Gal from a sugar and UTP, or treated products of these culture broths, as enzyme sources,

(15) globotriose can be formed from orotic acid, galactose and glucose by carrying out an enzyme reaction using culture broths of a microorganism having the ability to express *Neisseria*-derived β1,4-galactosyltransferase (WO 96/10086), a microorganism having the ability to express *Neisseria*-derived α1,4-galactosyltransferase (WO 96/10086), a microorganism having the ability to produce UTP from a precursor of UTP and a microorganism having the ability to produce UDP-Gal from a sugar and UTP, or treated products of these culture broths, as enzyme sources,

(16) Galα1-4Galβ1-4GlcNAc can be formed from orotic acid, galactose and N-acetyllactosamine by carrying out an enzyme reaction using culture broths of a microorganism having the ability to express *Neisseria*-derived α1,4-galactosyltransferase (WO 96/10086), a microorganism having the ability to produce UTP from a precursor of UTP and a microorganism having the ability to produce UDP-Gal from a sugar and UTP, or treated products of these culture broths, as enzyme sources,

(17) lacto-N-biose can be formed from orotic acid, galactose and N-acetylglucosamine by carrying out an enzyme reaction using culture broths of an animal cell line having the ability to express human-derived β1,3-galactosyltransferase (Japanese Published Unexamined Patent Application No. 181759/94), a microorganism having the ability to produce UTP from a precursor of UTP and a microorganism having the ability to produce UDP-Gal from a sugar and UTP, or treated products of these culture broths, as enzyme sources,

(18) sialyllacto-N-biose can be formed from orotic acid, N-acetylmannosamine, pyruvic acid and lacto-N-biose by carrying out an enzyme reaction using culture broths of a microorganism having the ability to express *Neisseria*-derived α2,3-sialyltransferase (*J. Biol. Chem.*, 271, 28271 (1996)), a microorganism having the ability to produce CTP from a precursor of CTP and a microorganism having the ability to produce CMP-NeuAc from a sugar and CTP, or treated products of these culture broths, as enzyme sources,

(19) sialyl-Lewis X can be formed from GMP, mannose and 3'-sialyl-N-acetyllactosamine by carrying out an enzyme reaction using culture broths of an animal cell line having the ability to express human-derived α1,3-fucosyltransferase. (*J. Biol. Chem.*, 269, 14730 (1994)), a microorganism having the ability to produce GTP from a precursor of GTP and a microorganism having the ability to produce GDP-Fuc from a sugar and GTP, or treated products of these culture broths, as enzyme sources,

(20) sialyl-Lewis a can be formed from GMP, mannose and sialyllacto-N-biose by carrying out an enzyme reaction using human (α1,3/1,4-fucosyltransferase (*Carbohydrate Research*, 190, 1 (1989)) and culture broths of a microorganism having the ability to produce GTP from a precursor of GTP and a microorganism having the ability to produce GDP-Fuc from a sugar and GTP, or treated products of these culture broths, as enzyme sources, and

(21) Manα1-2Man can be formed from GMP and mannose by carrying out an enzyme reaction using culture broths of *Escherichia coli* having the ability to express yeast-derived α1,2-mannosyltransferase (*J. Org. Chem.*, 58, 3985 (1993)), a microorganism having the ability to produce GTP from a precursor of GTP and a microorganism having the ability to produce GDP-Man from a sugar and GTP, or treated products of these culture broths, as enzyme sources.

Processes for producing complex carbohydrates are not limited to the above-mentioned examples, and any other sugar chain can be produced industrially using a nucleotide precursor, a sugar and a complex carbohydrate precursor as the sole starting materials, within the range of glycosyltransferases which can be combined with the sugar nucleotide production process described herein and of the substrate specificity acceptable by the enzymes.

Examples of the complex carbohydrate to be produced by the production process of the present invention include (1) complex carbohydrates involved in the infection with pathogenic microorganisms and viruses, such as complex carbohydrates which are recognized as receptors of pathogenic microorganisms and viruses, (2) complex carbohydrates which are recognized as receptors of toxins produced by pathogenic microorganisms and viruses, (3) complex carbohydrates which are concerned, for example, in cell adhesion, recognition of foreign substances and binding of various types of lymphokine in the living body, and complex carbohydrates which contain one or a plurality of sugars such as glucose, galactose, N-acetylglucosamine, N-acetylgalactosamine, glucuronic acid, mannose, N-acetylmannosamine, fucose, sialic acid and the like, in a chemically acceptable binding mode. More specific examples include (1) complex carbohydrates which are contained in the milk of human and animals, and involved in the protection of infants from microbial infection, for example, complex carbohydrates, such as lacto-N-tetraose, lacto-N-neotetraose, and the like, (2) receptor complex carbohydrates which recognize microorganisms, such as *Escherichia coli, Prapionibacterium granulosium, Mycobacterium tuberculosis, Moraxella catarahlis, Candida albicans, Staphylococcus saprophyticus, Streptococcus pneunmoniae, Streptococcus agalactiae,*

Pseudomonas aeruginosa, Actinomyces naeslundii, Neisseria gonorrhoeae, Helicobacter pylori, Haemophilus influenzae, and the like, (3) receptor complex carbohydrates of viruses, such as influenza virus, coronavirus, Sendai virus, newcastle disease virus, reovirus, rotavirus, AIDS (HIV) virus, and the like, (4) receptor complex carbohydrates of protozoa, such as Cryptosporidium, Trypanosoma, and the like, (5) receptor complex carbohydrates having the affinity for toxins, such as cholera toxin, Escherichia coli heat-labile toxin, botulinum toxin, clostridial 6 toxin, clostridial A toxin, Shiga toxin, Vero toxin, Shiga toxin-like toxin, Vibrio parahaemolyticus heat-stable toxin, tetanus toxin, and the like, (6) cancer-related complex carbohydrates such as gangliosides (for example, GD3, GM3, etc.), globoside glycolipids, and the like, (7) complex carbohydrates which are concerned in the adhesion of leukocytes to inflammatory regions and modification of their functions, such as sialyl-Lewis X sugar chain, and the like, (8) complex carbohydrates concerned in autoimmune diseases, such as rheumatoid arthritis, IgA glomerulonephritis, and the like, and (9) complex carbohydrates which are recognized by various lectin-like substances concerned in the recognition of foreign bodies and cancer cells.

Determination of the complex carbohydrate formed in the aqueous medium can be carried out in accordance with known methods (*Proc. Natl. Acad. Sci. USA.*, 85, 3289 (1988), *Anal. Biochem.*, 174, 459 (1988)).

Recovery of the complex carbohydrate formed in the reaction solution can be carried out in the usual way using activated carbon, an ion exchange resin and the like, for example, N-acetyllactosamine can be recovered in accordance with the process described in *J. Org. Chem.*, 47, 5416 (1982).

Examples of the present invention are given below by way of illustration and not by way of limitation.

BEST MODE OF CARRYING OUT THE INVENTION

Example 1

Construction of Recombinant Plasmid Capable of Expressing galU and ppa

Figure 2:
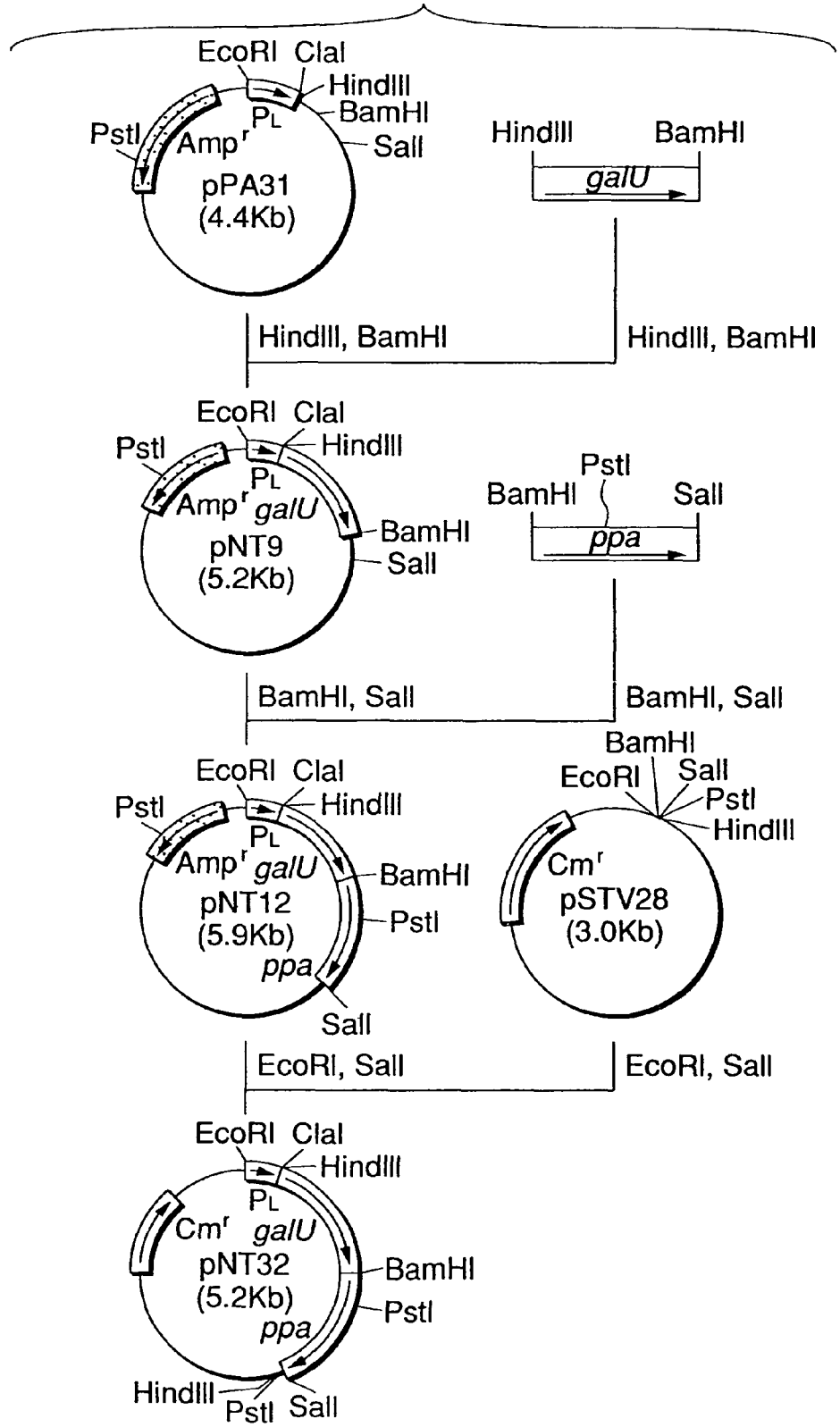
FIG. 2 shows construction steps of galu, ppa gene expression plasmids pNT12 and pNT32.

Construction process of recombinant plasmid pNT12 capable of expressing galU and ppa is described in the following (FIGS. 1 and 2).

1) Construction of Expression Vector Containing $P_L$ Promoter

Construction of pPA31 and pPAC31 as $P_L$ promoter-containing expression vectors were carried out in the following manner (FIG. 1).

*Escherichia coli* JM109/pTrS30 (FERM BP-5407) which has tryptophan promoter-containing plasmid pTrS30 and another *Escherichia coli* which has $P_L$ promoter-containing plasmid pPA1 (Japanese Published Unexamined Patent Application No. 233798/88) and $P_L$ promoter- and cI857 repressor-containing plasmid pPAC1 (FERM BP-6054) were separately inoculated into LB medium (10 g/l Bacto-Tryptone (manufactured by Difco), 5 g/l Yeast Extract (manufactured by Difco) and 5 g/l NaCl, adjusted to pH 7.2) and cultured at 30° C. for 18 hours.

From the cells obtained by the culturing, pTrS30, pPA1 and pPAC1 plasmid DNAs were isolated and purified by the above-mentioned known processes.

A 0.2 µg portion of the thus purified pTrS30 DNA was cleaved with restriction enzymes PstI and ClaI, the resulting DNA fragments were separated by agarose gel electrophoresis and then a fragment of 3.4 kb was recovered using Gene Clean II Kit (manufactured by Bio101). A 0.5 µg portion of the purified pPA1 DNA was cleaved with restriction enzymes PstI and ClaI, the resulting DNA fragments were separated by agarose gel electrophoresis and then a fragment of 1.0 kb was recovered in the same manner.

Using a ligation kit (TAKARA Ligation Kit, manufactured by Takara Shuzo Co., Ltd.), the fragments of 3.4 kb and 1.0 kb were subjected to ligation reaction for 16 hours at 16° C.

Using the ligation reaction solution, *Escherichia coli* NM522 was transformed in accordance with the above-mentioned known process, and the resulting transformant was spread on LB agar medium containing 50 µg/ml ampicillin and then cultured overnight at 37° C.

By extracting a plasmid from the thus grown colonies of the transformant in accordance with the above-mentioned known process, the $P_L$ promoter-effected expression vector pPA31 was obtained. Structure of the plasmid was recognized by restriction enzyme cleavage (FIG. 1).

A 0.2 µg portion of the purified pPA31 DNA was cleaved with restriction enzymes PstI and ClaI, the resulting DNA fragments were separated by agarose gel electrophoresis and then a fragment of 3.4 kb was recovered using Gene Clean II Kit. A 0.5 µg portion of the purified pPAC1 DNA was cleaved with restriction enzymes PstI and ClaI, the resulting DNA fragments were separated by agarose gel electrophoresis and then a fragment of 2.3 kb was recovered in the same manner.

Using a ligation kit, the fragments of 3.4 kb and 2.3 kb were subjected to ligation reaction for 16 hours at 16° C.

Using the ligation reaction solution, *Escherichia coli* NM522 was transformed in accordance with the above-mentioned known process, and the resulting transformant was spread on LB agar medium containing 50 µg/ml ampicillin and then cultured overnight at 37° C.

By extracting a plasmid from the thus grown colonies of the transformant in accordance with the above-mentioned known process, the $P_L$ promoter-effected cI857 repressor-containing expression vector pPAC31 was obtained. Structure of the plasmid was recognized by restriction enzyme cleavage (FIG. 1).

2) Construction of galU Expression Plasmid

Chromosomal DNA of *Escherichia coli* W3100 was isolated and purified by a known process (for example, Current Protocols in Molecular Biology, John Wiley and Sons Inc. (1994)).

The sense strand DNA primer shown in SEQ ID NO:1 and the antisence strand DNA primer shown in SEQ ID NO:2 were synthesized using 380A DNA Synthesizer manufactured by Applied Biosystems.

The PCR process was carried out using the synthesized DNA strands as primers, and the chromosomal DNA of the strain W3110 as the template. The PCR was effected using 40 µl of a reaction solution containing 0.04 µg of the W3110 chromosomal DNA, 0.5 µM of each primer, 1.0 unit of TAKARA Ex Taq (manufactured by Takara Shuzo Co., Ltd.), 4 µl of 10× Ex Taq buffer (manufactured by Takara Shuzo Co., Ltd.) and 200 µM of each deoxyNTP, and repeating 30 cycles of the reaction, each cycle containing 94° C. for 1 minute, 42° C. for 2 minutes and 72° C. for 3 minutes.

A 1/10 volume of the reaction solution was subjected to agarose gel electrophoresis to verify amplification of the fragment of interest, and then the remaining reaction solution was mixed with the same volume of phenol/chloroform (1 vol/1 vol) solution with saturated TE (10 mM Tris-HCl buffer (pH 8.0) and 1 mM EDTA). The mixture solution was centrifuged, and the thus obtained upper layer was mixed with 2 volumes of cold ethanol and allowed to stand for 30 minutes at −80° C. The solution after standing was centrifuged to obtain a precipitate of DNA. The precipitate was washed with 70% cold ethanol and dried in vacuo to recover the precipitate. Hereinafter, the steps starting from the addition of phenol/chloroform solution with saturated TE until the recovery of the ethanol-washed DNA are referred to as an ethanol precipitation process.

The DNA precipitate was dissolved in 20 µl of TE. Using 5 µl portion of the solution, DNA was cleaved with restriction enzymes HindIII and BamHI, the resulting DNA fragments were separated by agarose gel electrophoresis and then a fragment of 0.9 kb was recovered using Gene Clean II Kit. A 0.2 µg portion of pPA31 DNA obtained in Example 1-1) was cleaved with restriction enzymes HindIII and BamHI, the resulting DNA fragments were separated by agarose gel electrophoresis and then a fragment of 4.2 kb was recovered in the same manner.

Using a ligation kit, the fragments of 0.9 kb and 4.2 kb were subjected to ligation reaction for 16 hours at 16° C.

Using the ligation reaction solution, *Escherichia coli* KY8415 was transformed in accordance with the above-mentioned known process, and the resulting transformant was spread on LB agar medium containing 50 µg/ml ampicillin and then cultured overnight at 30° C.

By extracting a plasmid from the thus grown colonies of the transformant in accordance with the above-mentioned known process, galU expression plasmid pNT9 was obtained. Structure of the plasmid was recognized by restriction enzyme cleavage (FIG. 2).

3) Construction of Simultaneous galU, ppa Expression Plasmid

The sense strand DNA primer shown in SEQ ID NO:3 and the antisence strand DNA primer shown in SEQ ID NO:4 were synthesized, and the PCR was carried out using the synthesized DNA strands as primers, and the chromosomal DNA of the strain W3110 as the template, under the same conditions as described in the foregoing.

After completion of the PCR, a precipitate of DNA was obtained by the ethanol precipitation process. The precipitate was dissolved in 20 µl of TE. Using 5 µl portion of the solution, the DNA was cleaved with restriction enzymes BamHI and SalI, the resulting DNA fragments were separated by agarose gel electrophoresis and then a fragment of 1.0 kb was recovered using Gene Clean II Kit. A 0.2 µg portion of pNT9 DNA obtained in Example 1-2) was cleaved with restriction enzymes BamHI and salI, the resulting DNA fragments were separated by agarose gel electrophoresis and then a fragment of 4.9 kb was recovered in the same manner.

Using a ligation kit, the fragments of 1.0 kb and 4.9 kb were subjected to ligation reaction for 16 hours at 16° C.

Using the ligation reaction solution, *Escherichia coli* KY8415 was transformed in accordance with the above-mentioned known process, and the resulting transformant was spread on LB agar medium containing 50 µg/ml ampicillin and then cultured overnight at 30° C.

By extracting a plasmid from the thus grown colonies of the transformant in accordance with the above-mentioned known process, the galU, ppa simultaneous expression plasmid pNT12 was obtained. Structure of the plasmid was recognized by restriction enzyme cleavage (FIG. 2).

A 0.5 µg portion of the pNT12 DNA was cleaved with restriction enzymes EcoRI and SalI, the resulting DNA fragments were separated by agarose gel electrophoresis and then a fragment of 2.2 kb was recovered using Gene Clean II Kit. Separately from this, a 0.2 µg portion of pSTV28 DNA (manufactured by Takara Shuzo Co., Ltd.) was cleaved with restriction enzymes EcoRI and SalI, the resulting DNA fragments were separated by agarose gel electrophoresis and then a fragment of 3.0 kb was recovered in the same manner.

Using a ligation kit, the fragments of 2.2 kb and 3.0 kb were subjected to ligation reaction for 16 hours at 16° C.

Using the ligation reaction solution, *Escherichia coli* NM522 was transformed in the usual way, and the resulting transformant was spread on LB agar medium containing 10 µg/ml chloramphenicol and then cultured overnight at 30° C.

By extracting a plasmid from the thus grown colonies of the transformant in the usual way, the galU, ppa simultaneous expression plasmid pNT32 was obtained. Structure of the plasmid was recognized by restriction enzyme cleavage (FIG. 2).

Example 2

Production of UDP-Glc

*Escherichia coli* KY8415/pNT12 obtained in Example 1 was inoculated into a 1 L baffled conical flask containing 125 ml of LB medium supplemented with 50 µg/ml ampicillin and cultured at 30° C. for 17 hours under shaking at 220 rpm. A 125 ml portion of the culture broth was inoculated into a 5 L culture vessel containing 2.5 L of an aqueous medium (without adjusting pH) which contains 10 g/l glucose, 12 g/l Bacto-Tryptone (manufactured by Difco), 24 g/l Yeast Extract (manufactured by Difco), 2.3 g/l $KH_2PO_4$ (separate sterilization), 12.5 g/l $K_2HPO_4$ (separate sterilization) and 50 µg/ml ampicillin and cultured at 30° C. for 4 hours and then at 40° C. for 3 hours, under conditions of 600 rpm and 2.5 L/min of aeration.

During the culturing, pH of the medium was maintained at 7.0 using 28% aqueous ammonia. In addition, glucose was added during the culturing when required. The culture broth was centrifuged to obtain wet cells. As occasion demands, these wet cells can be preserved at −20° C. and utilized by thawing the cells prior to use.

*Corynebacterium ammoniagenes* ATCC 21170 was inoculated into a 300 ml-baffled conical flask containing 20 ml of an aqueous medium of 50 g/l glucose, 10 g/l Polypeptone (manufactured by Nippon Seiyaku), 10 g/l Yeast Extract (manufactured by Oriental Yeast), 5 g/l urea, 5 g/l $(NH_4)_2SO_4$, 1 g/l $KH_2PO_4$, 3 g/l $KH_2PO_4$, 1 g/l $MgSO_4.7H_2O$, 0.1 g/l $CaCl_2.2H_2O$, 10 mg/l $FeSO_4.7H_2O$, 10 mg/l $ZnSO_4.7H_2O$, 20 mg/l $MnSO_4.4$-$6H_2O$, 20 mg/l L-cysteine, 10 mg/l calcium D-pantothenate, 5 mg/l vitamin $B_1$, 5 mg/l nicotinic acid and 30 µg/l biotin (adjusted to pH 7.2 with 10 N NaOH) and cultured at 28° C. for 24 hours under shaking at 220 rpm.

A 20 ml portion of the culture broth was inoculated into a 2 L baffled conical flask containing 250 ml of the same aqueous medium and cultured at 28° C. for 24 hours under shaking at 220 rpm. The thus obtained culture broth was used as a seed culture broth.

A 250 ml portion of the seed culture broth was inoculated into a 5 L culture vessel containing 2.25 L of an aqueous medium of 150 g/l glucose, 5 g/l meat extract (manufactured by Kyokuto Pharmaceutical Industry), 10 g/l $KH_2PO_4$, 10 g/l $K_2HPO_4$, 10 g/l $MgSO_4.7H_2O$, 0.1 g/l $CaCl_2.2H_2O$, 20 mg/l $FeSO_4.7H_2O$, 10 mg/l $ZnSO_4.7H_2O$, 20 mg/l $MnSO_4.4$-$6H_2O$ (separate sterilization), 15 mg/l β-alanine (separate sterilization), 20 mg/l L-cysteine, 100 µg/l biotin, 2 g/l urea and 5 mg/l vitamin $B_1$ (separate sterilization) (adjusted to pH 7.2 with 10 N NaOH) and cultured at 32° C. for 24 hours under conditions of 600 rpm and 2.5 L/min of aeration. During the culturing, pH of the culture broth was maintained at 6.8 using 28% aqueous ammonia.

The culture broth was centrifuged to obtain wet cells. As occasion demands, these wet cells can be preserved at −20° C. and utilized by thawing the cells prior to use.

A 30 ml portion of a reaction solution having a composition of 40 g/l *Escherichia coli* KY8415/pNT12 wet cells, 150 g/l *Corynebacterium ammoniagenes* ATCC 21170 wet cells, 100 g/l glucose, 20 g/l $KH_2PO_4$, 5 g/l $MgSO_4.7H_2O$, 5 g/l phytic acid, 21.2 g/l orotic acid (potassium salt), 4 g/l Nymeen S-215 and 10 ml/l xylene was put into a 200 ml beaker, and 21 hours of the reaction was carried out at 32° C. under stirring the reaction solution with a magnetic stirrer (900 rpm).

During the reaction, pH of the reaction solution was maintained at 7.2 using 4 N NaOH, and glucose and $KH_2PO_4$ were added when required.

By the reaction, 43.9 g/l UDP-Glc (2Na salt) was formed in the reaction solution.

Example 3

Construction of Recombinant Plasmid Capable of Expressing galT and galK

Figure 3:
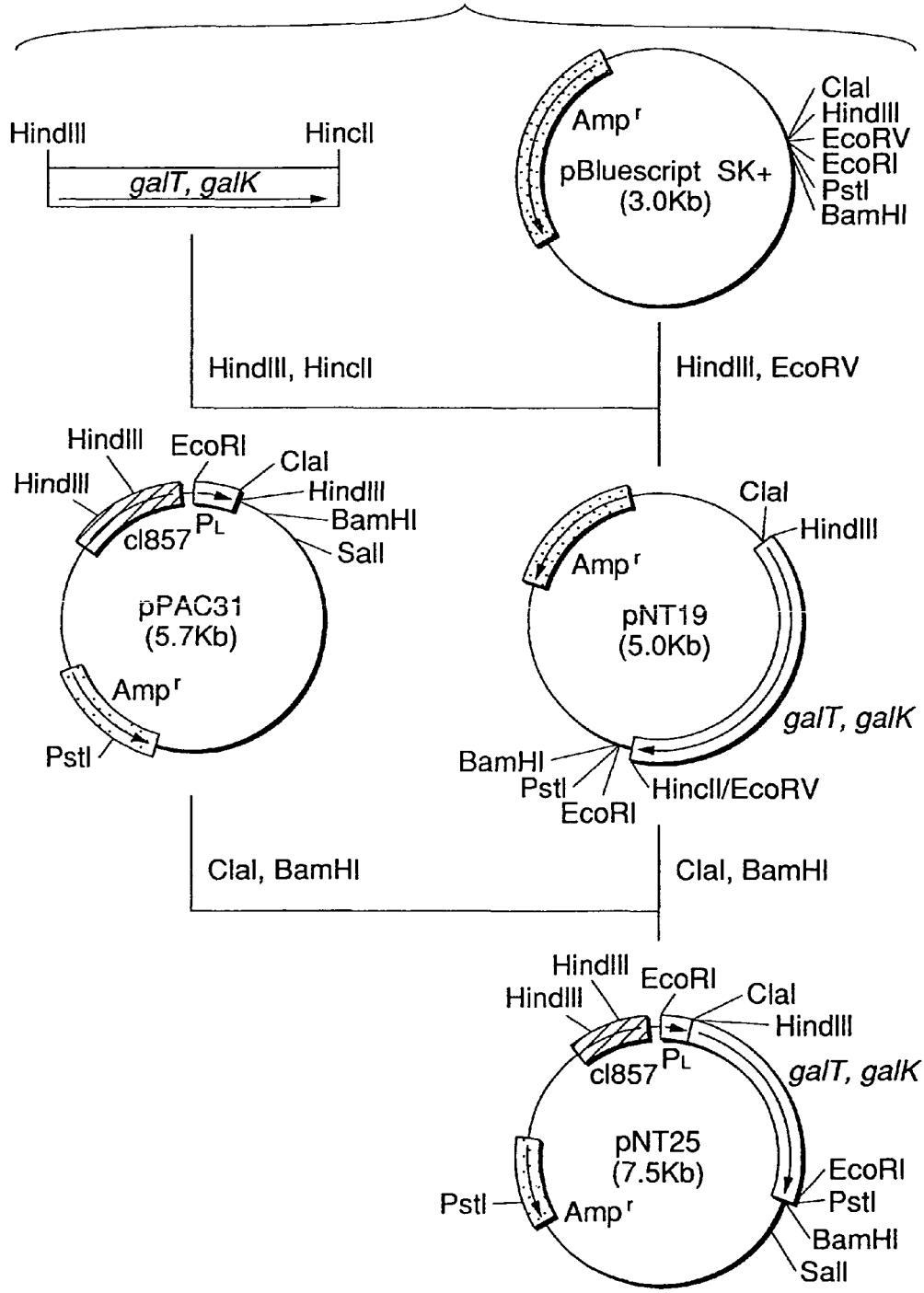
FIG. 3 shows construction steps of galT, galK gene expression plasmid pNT25.

Construction process of recombinant plasmid pNT25 capable of expressing galT and galK is described in the following (FIG. 3).

The sense strand DNA primer shown in SEQ ID NO:5 and the antisence strand DNA primer shown in SEQ ID NO:6 were synthesized. The PCR was carried out using the synthesized DNA strands as primers, and the chromosomal DNA of the strain W3110 as the template, under the same conditions as described in the foregoing.

After completion of the PCR treatment, a precipitate of DNA was obtained by the ethanol precipitation process. The precipitate was dissolved in 20 µl of TE. Using 5 µl portion of the solution, the DNA was cleaved with restriction enzymes HindIII and HincII, the resulting DNA fragments were separated by agarose gel electrophoresis and then a fragment of 2.3 kb was recovered using Gene Clean II Kit. A 0.2 µg portion of pBluescript II SK+ DNA was cleaved with restriction enzymes HindIII and EcoRV, the resulting DNA fragments were separated by agarose gel electrophoresis and then a fragment of 3.0 kb was recovered in the same manner.

Using a ligation kit, the fragments of 2.3 kb and 3.0 kb were subjected to ligation reaction for 16 hours at 16° C.

Using the ligation reaction solution, *Escherichia coli* NH522 was transformed in accordance with the above-mentioned known process, and the resulting transformant was spread on LB agar medium containing 50 µg/ml ampicillin and then cultured overnight at 30° C.

By extracting a plasmid from the thus grown colonies of the transformant in accordance with the above-mentioned known process, plasmid pNT19 containing galT and galK genes was obtained. Structure of the plasmid was recognized by restriction enzyme cleavage (FIG. 3).

A 0.5 µg portion of the pNT19 DNA was cleaved with restriction enzymes ClaI and BamHI, the resulting DNA fragments were separated by agarose gel electrophoresis and then a fragment of 2.3 kb was recovered in the same manner. A 0.2 µg portion of the pPAC31 DNA obtained in Example 1-1) was cleaved with restriction enzymes ClaI and BamHI, the resulting DNA fragments were separated by agarose gel electrophoresis and then a fragment of 5.5 kb was recovered in the same manner.

Using a ligation kit, the fragments of 2.3 kb and 5.5 kb were subjected to ligation reaction for 16 hours at 16° C.

Using the ligation reaction solution, *Escherichia coli* NM52 was transformed in accordance with the above-mentioned known process, and the resulting transformant was spread on LB agar medium containing 50 µg/ml ampicillin and then cultured overnight at 30° C.

By extracting a plasmid from the thus grown colonies of the transformant in accordance with the above-mentioned known process, plasmid pNT25 capable of expressing galT and galK simultaneously was obtained. Structure of the plasmid was recognized by restriction enzyme cleavage (FIG. 3).

Example 4

Production of UDP-Gal

1) Preparation of galT, galK, galU, ppa Expression Strain

Using the pNT32 DNA obtained in Example 1-3), *Escherichia coli* NM522/pNT25 was transformed in accordance with the above-mentioned known process, and the resulting transformant was spread on LB agar medium containing 50 µg/ml ampicillin and 10 µg/ml chloramphenicol and then cultured overnight at 30° C. By selecting the thus grown transformants, *Escherichia coli* NM522/pNT25/pNT32 was obtained as the galT, galK, galU, ppa expression strain.

2) Production of UDP-Gal

*Escherichia coli* NH522/pNT25/pNT32 obtained in Example 4-1) was cultured in the same manner as in Example 2, and the culture broth was centrifuged to obtain wet cells. Also, *Corynebacterium ammoniagenes* ATCC 21170 was cultured in the same manner as in Example 2, and the culture broth was centrifuged to obtain wet cells. As occasion demands, the wet cells can be preserved at −20° C. and utilized by thawing them prior to use.

A 2 L portion of a reaction solution having a composition of 50 g/l *Escherichia coli* NM522/pNT25/pNT32 wet cells, 150 g/l *Corynebacterium ammoniagenes* ATCC 21170 wet cells, 80 g/l glucose, 20 g/l galactose, 15 g/l $KH_2PO_4$, 5 g/l $MgSO_4.7H_2O$, 5 g/l phytic acid, 21.2 g/l orotic acid (potassium salt), 4 g/l Nymeen S-215 and 10 ml/l xylene was put into 5 L culture vessel, and 26 hours of the reaction was carried out at 32° C. under stirring the reaction solution at 600 rpm with an aeration rate of 1 L/min.

During the reaction, pH of the reaction solution was maintained at 7.2 using 4 N NaOH, and glucose, galactose and $KH_2PO_4$ were added when required.

By the reaction, 47.4 g/l UDP-Gal (2Na salt) was formed in the reaction solution.

Example 5

Construction of Recombinant Plasmid Capable of Expressing galT and galK in *Corynebacterium Ammoniagenes*

Figure 4:
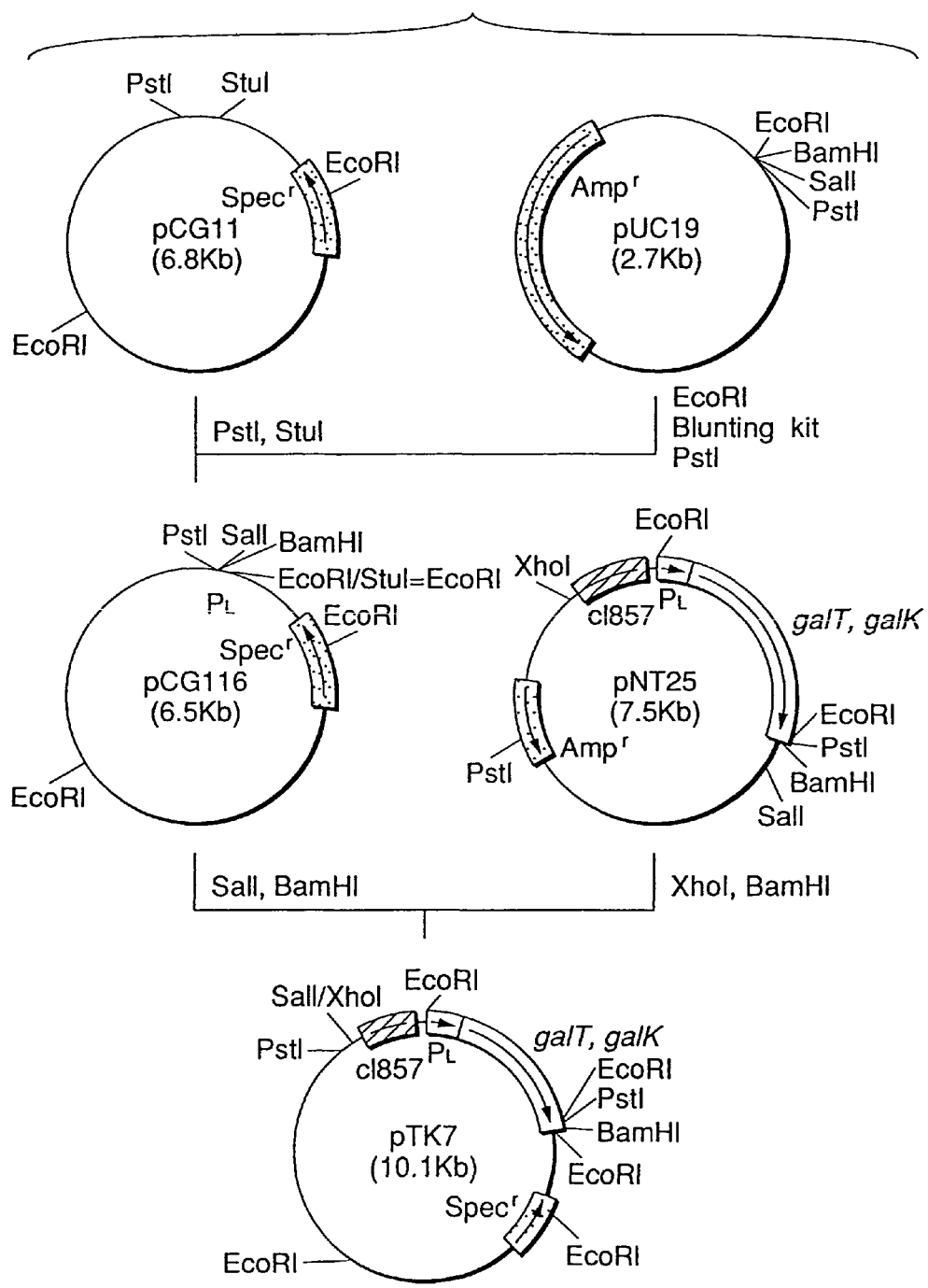
FIG. 4 shows construction steps of plasmid pTK7 which expresses galT and galK genes in *Corynebacterium ammoniagenes*.

Construction process of recombinant plasmid pTK7 capable of expressing *Escherichia coli*-derived galT and galK in *Corynebacterium ammoniagenes* is described in the following (FIG. 4).

1) Construction of pCG116

Plasmid pCG116 capable of replicating in *Corynebacterium ammoniagenes* was constructed in the following manner.

A 0.5 µg portion of plasmid pCG11 (Japanese Published Examined Patent Application No. 91827/94) DNA was cleaved with restriction enzymes PstI and StuI, the resulting DNA fragments were separated by agarose gel electrophoresis and then a fragment of 6.5 kb was recovered using Gene Clean II Kit.

On the other hand, a 1.0 µg portion of plasmid pUC19 DNA was cleaved with a restriction enzyme EcoRI and then blunt-ended using DNA Blunting Kit (manufactured by Takara Shuzo Co., Ltd.). The DNA thus blunt-ended was cleaved with a restriction enzyme PstI, the resulting DNA fragments were separated by agarose gel electrophoresis and then a fragment of 43 bp was recovered using MERmaid Kit (manufactured by Bio101).

Using a ligation kit, the fragments of 6.5 kb and 43 bp were subjected to ligation reaction for 16 hours at 16° C.

Using the ligation reaction solution, *Corynebacterium ammoniagenes* ATCC 21170 was transformed by the electroporation method (*FEMS Microbial. Lett.,* 65, 299 (1989)), and the resulting transformant was spread on LB agar medium containing 100 µg/ml spectinomycin and then cultured at 30° C. for 2 days.

By extracting a plasmid from the thus grown colonies of the transformant in accordance with the known process (*J. Bacteriol.,* 159, 306 (1984)), plasmid pCG116 was obtained. Structure of the plasmid was recognized by restriction enzyme cleavage (FIG. 4).

2) Construction of pTK7 Capable of Expressing galT and galK

A 1.0 µg portion of the galT and galK expression plasmid pNT25 DNA obtained in Example 3 was cleaved with restriction enzymes XhoI and BamHI, the resulting DNA fragments were separated by agarose gel electrophoresis and then a fragment of 3.5 kb was recovered using Gene Clean II Kit.

On the other hand, a 0.5 µg portion of the plasmid pCG116 DNA prepared in Example 5-1) was cleaved with a restriction enzymes SalI and BamHI, the resulting DNA fragments were separated by agarose gel electrophoresis and then a fragment of 6.5 kb was recovered in the same manner.

Using a ligation kit, the fragments of 3.5 kb and 6.5 kb were subjected to ligation reaction for 16 hours at 16° C.

Using the ligation reaction solution, *Corynebacterium ammoniagenes* ATCC 21170 was transformed by the electroporation process, and the resulting transformant was spread on LB agar medium containing 100 µg/ml spectinomycin and then cultured at 30° C. for 2 days.

By extracting a plasmid from the thus grown colonies of the transformant in accordance with the known process, plasmid pTK7 capable of expressing galT and galK simultaneously was obtained. Structure of the plasmid was recognized by restriction enzyme cleavage (FIG. 4).

Example 6

Production of UDP-Gal

*Corynebacterium ammoniagenes* ATCC 21170/pTK7 obtained in Example 5 was cultured by the same process as described in Example 2 at 32° C. for 20 hours and then at 40° C. for 4 hours, and the thus obtained culture broth was centrifuged to obtain wet cells. As occasion demands, the wet cells can be preserved at −20° C. and utilized by thawing them prior to use.

A 30 ml portion of a reaction solution having a composition of 150 g/l *Corynebacterium ammoniagenes* ATCC 21170/pTK7 wet cells, 40 g/l fructose, 20 g/l galactose, 15 g/l $KH_2PO_4$, 5 g/l $MgSO_4.7H_2O$, 5 g/l phytic acid, 10.6 g/l orotic acid (potassium salt), 4 g/l Nymeen S-215 and 10 ml/l xylene was put into a 200 ml beaker, and 22 hours of the reaction was carried out at 32° C. under stirring the reaction solution with a magnetic stirrer (900 rpm).

During the reaction, pH of the reaction solution was maintained at 7.2 using 4 N NaOH, and fructose, galactose and $KH_2PO_4$ were added when required.

By the reaction, 7.2 g/l UDP-Gal (2Na salt) was formed in the reaction solution.

Example 7

Construction of glmU, ppa, pgm, glmM, glk and pfkB Expression Plasmid

1) Construction of glmU and ppa Expression Plasmid

The sense strand DNA primer shown in SEQ ID NO:7 and the antisence strand DNA primer shown in SEQ ID NO:8 were synthesized. The PCR was carried out using the synthesized DNA strands as primers, and the chromosomal DNA of the strain W3110 as the template, under the same conditions as described in the foregoing.

After completion of the PCR treatment, a precipitate of DNA was obtained by the ethanol precipitation process. The DNA precipitate was dissolved in 20 µl of TE. Using 5 µl portion of the solution, the DNA was cleaved with restriction enzymes HindIII and BamHI, the resulting DNA fragments were separated by agarose gel electrophoresis and then a fragment of 1.4 kb was recovered using Gene Clean II Kit. A 0.5 µg portion of pPA31 DNA obtained in Example 1-1) was cleaved with restriction enzymes HindIII and BamHI, the resulting DNA fragments were separated by agarose gel electrophoresis and then a fragment of 4.2 kb was recovered in the same manner.

Using a ligation kit, the fragments of 1.4 kb and 4.2 kb were subjected to ligation reaction for 16 hours at 16° C.

Using the ligation reaction solution, *Escherichia coli* KY8415 was transformed in accordance with the above-mentioned known process, and the resulting transformant was spread on LB agar medium containing 50 µg/ml ampicillin and then cultured overnight at 30° C.

Figure 5:
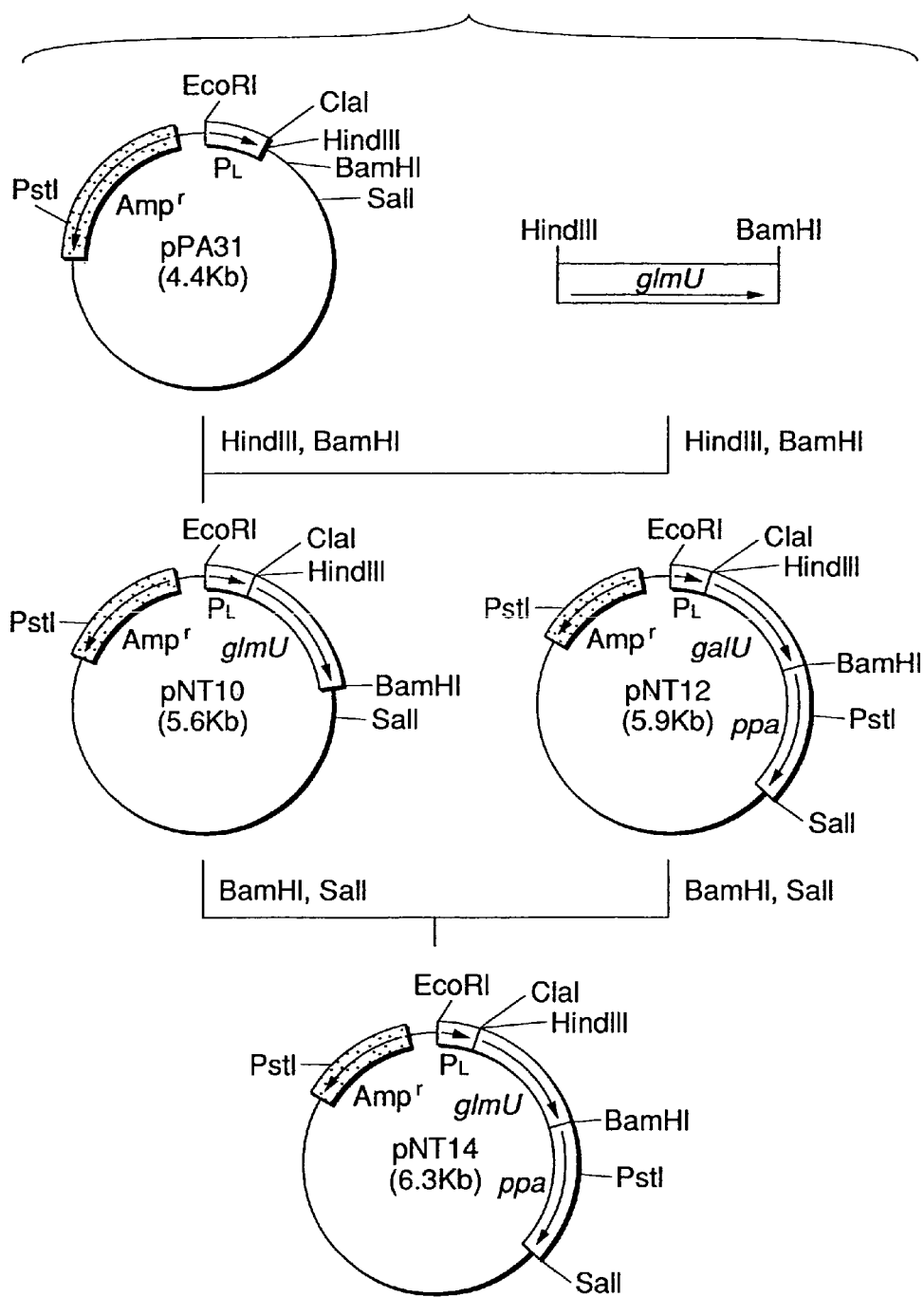
FIG. 5 shows construction steps of glmU, ppa gene expression plasmid pNT14.

By extracting a plasmid from the thus grown colonies of the transformant in accordance with the above-mentioned known process, glmU expression plasmid pNT10 was obtained. Structure of the plasmid was recognized by restriction enzyme cleavage (FIG. 5).

A 0.5 µg portion of the pNT12 DNA obtained in Example 1-3) was cleaved with restriction enzymes BamHI and SalI, the resulting DNA fragments were separated by agarose gel electrophoresis and then a fragment of 1.0 kb was recovered in the same manner. A 0.2 µg portion of the just described pNT10 DNA was cleaved with restriction enzymes BamHI and SalI, the resulting DNA fragments were separated by agarose gel electrophoresis and then a fragment of 5.3 kb was recovered in the same manner.

Using a ligation kit, the fragments of 1.0 kb and 5.3 kb were subjected to ligation reaction for 16 hours at 16° C.

Using the ligation reaction solution, *Escherichia coli* KY8415 was transformed in accordance with the above-mentioned known process, and the resulting transformant was spread on LB agar medium containing 50 µg/ml ampicillin and then cultured overnight at 30° C.

By extracting a plasmid from the thus grown colonies of the transformant in accordance with the above mentioned known process, the glmu, ppa simultaneous expression plasmid pNT14 was obtained. Structure of the plasmid was recognized by restriction enzyme cleavage (FIG. 5).

2) Construction of pgm Expression Plasmid

The sense strand DNA primer shown in SEQ ID NO:9 and the antisence strand DNA primer shown in SEQ ID NO:10 were synthesized. The PCR was carried out using the synthesized DNA strands as primers, and the chromosomal DNA of the strain W3110 as the template, under the same conditions as described in the foregoing.

After completion of the PCR, a precipitate of DNA was obtained by the ethanol precipitation process. The precipitate was dissolved in 20 µl of TE. Using 5 µl portion of the solution, the DNA was cleaved with restriction enzymes ClaI and BamHI, the resulting DNA fragments were separated by agarose gel electrophoresis and then a fragment of 1.8 kb was recovered using Gene Clean II Kit. A 0.2 µg portion of the pPAC31 DNA obtained in Example 1-1) was cleaved with restriction enzymes ClaI and BamHI, the resulting DNA fragments were separated by agarose gel electrophoresis and then a fragment of 5.5 kb was recovered in the same manner.

Using a ligation kit, the fragments of 1.8 kb and 5.5 kb were subjected to ligation reaction for 16 hours at 16° C.

Using the ligation reaction solution, *Escherichia coli* NM522 was transformed in accordance with the above-mentioned known process, and the resulting transformant was spread on LB agar medium containing 50 µg/ml ampicillin and then cultured overnight at 30° C.

Figure 6:
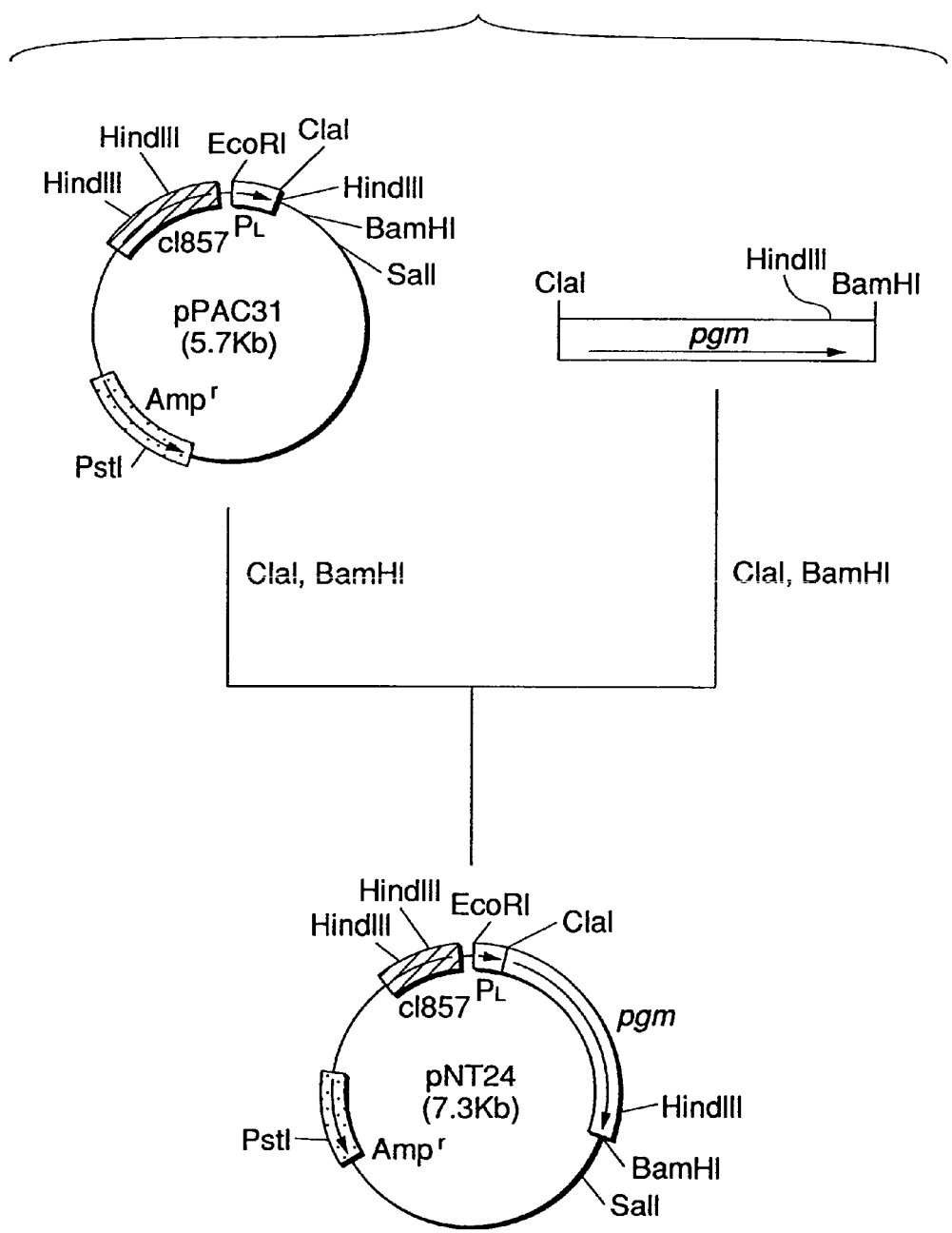
FIG. 6 shows construction steps of pgm gene expression plasmid pNT24.

By extracting a plasmid from the thus grown colonies of the transformant in accordance with the above-mentioned known process, pgm expression plasmid pNT24 was obtained. Structure of the plasmid was recognized by restriction enzyme cleavage (FIG. 6).

3) Construction of glmM Expression Plasmid

The sense strand DNA primer shown in SEQ ID NO:11 and the antisence strand DNA primer shown in SEQ ID NO:12 were synthesized. The PCR was carried out using the synthesized DNA strands as primers, and the chromosomal DNA of *Escherichia coli* W3110 as the template, under the same conditions as described in the foregoing.

After completion of the PCR, a precipitate of DNA was obtained by the ethanol precipitation process. The precipitate was dissolved in 20 µl of TE. Using 5 µl portion of the solution, the DNA was cleaved with restriction enzymes ClaI and BamHI, the resulting DNA fragments were separated by agarose gel electrophoresis and then a fragment of 1.6 kb was recovered using Gene Clean II Kit. A 0.2 µg portion of the pPAC31 DNA obtained in Example 1-1) was cleaved with restriction enzymes ClaI and BamHI, the resulting DNA fragments were separated by agarose gel electrophoresis and then a fragment of 5.5 kb was recovered in the same manner.

Using a ligation kit, the fragments of 1.6 kb and 5.5 kb were subjected to ligation reaction for 16 hours at 16° C.

Using the ligation reaction solution, *Escherichia coli* NM522 was transformed in accordance with the above-mentioned known process, and the resulting transformant was spread on LB agar medium containing 50 µg/ml ampicillin and then cultured overnight at 30° C.

Figure 7:
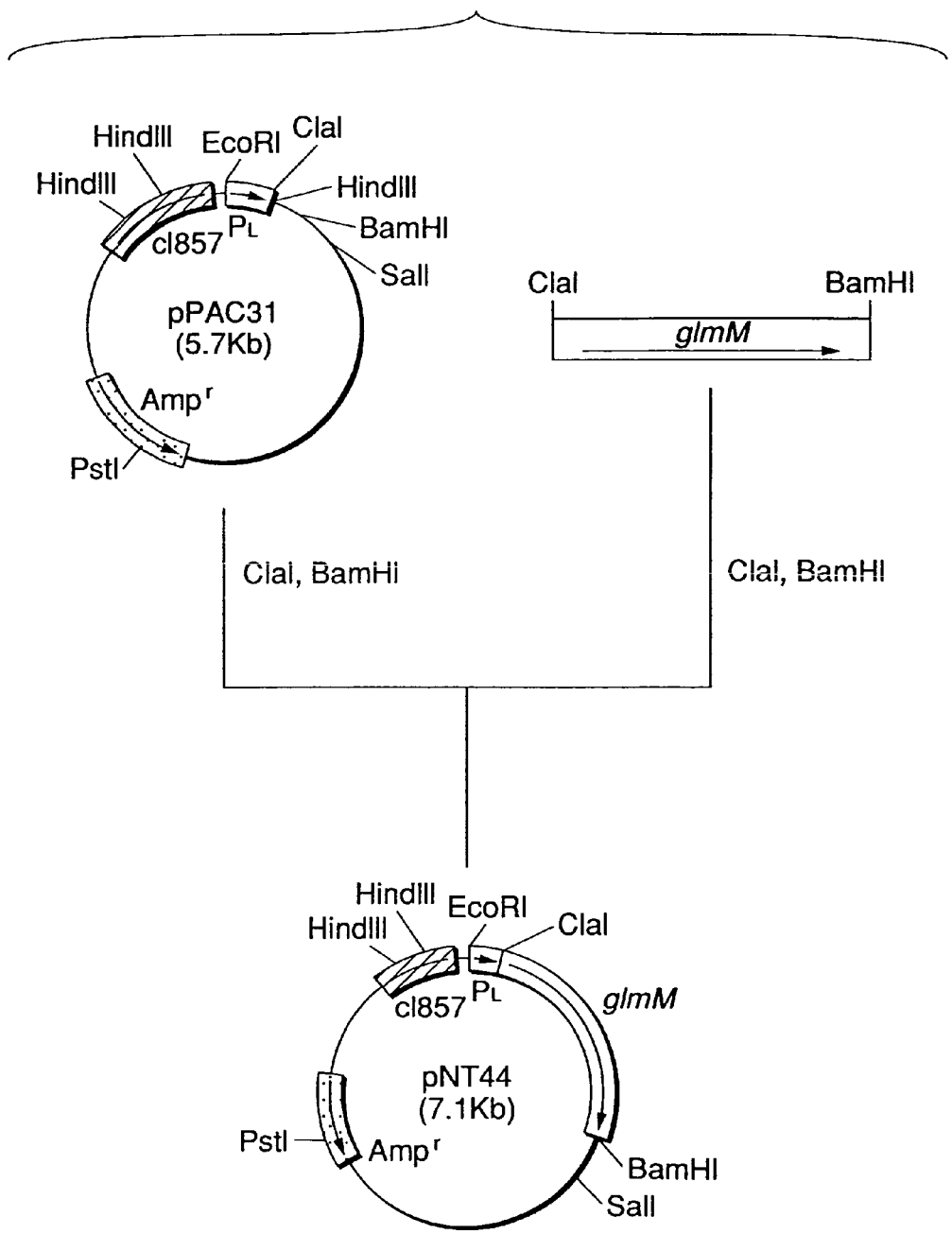
FIG. 7 shows construction steps of glmM gene expression plasmid pNT44.

By extracting a plasmid from the thus grown colonies of the transformant in accordance with the above-mentioned known process, glmM expression plasmid pNT44 was obtained. Structure of the plasmid was recognized by restriction enzyme cleavage (FIG. 7).

4) Construction of glk Expression Plasmid

The sense strand DNA primer shown in SEQ ID NO:13 and the antisence strand DNA primer shown in SEQ ID NO:14 were synthesized. The PCR was carried out using the synthesized DNA strands as primers, and the chromosomal DNA of *Escherichia coli* W3110 as the template, under the same conditions as described in the foregoing.

After completion of the PCR, a precipitate of DNA was obtained by the ethanol precipitation process. The precipitate was dissolved in 20 µl of TE. Using 5 µl portion of the solution, the DNA was cleaved with restriction enzymes HindIII and BamHI, the resulting DNA fragments were separated by agarose gel electrophoresis and then a fragment of 0.5 kb was recovered using Gene Clean II Kit.

A 0.2 µg portion of the pPA31 DNA obtained in Example 1-1) was cleaved with restriction enzymes HindIII and BamHI, the resulting DNA fragments were separated by agarose gel electrophoresis and then a fragment of 4.2 kb was recovered in the same manner.

Using a ligation kit, the fragments of 0.5 kb and 4.2 kb were subjected to ligation reaction for 16 hours at 16° C.

Using the ligation reaction solution, *Escherichia coli* NM522 was transformed in accordance with the usual process, and the resulting transformant was spread on LB agar medium containing 50 µg/ml ampicillin and then cultured overnight at 30° C.

Figure 8:
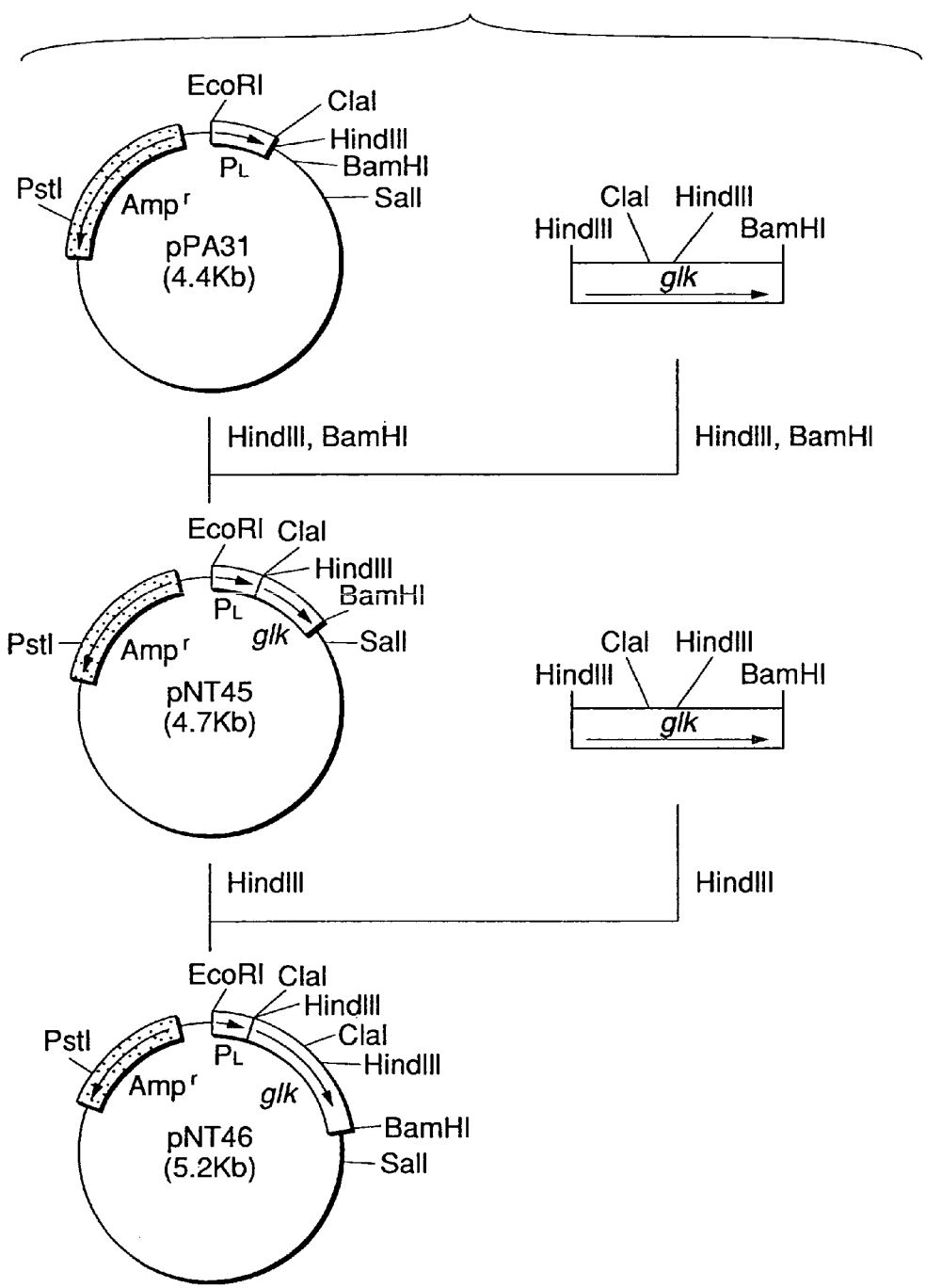
FIG. 8 shows construction steps of glk gene expression plasmid pNT46.

By extracting a plasmid from the thus grown colonies of the transformant in the usual way, plasmid pNT45 containing a part of glk was obtained. Structure of the plasmid was recognized by restriction enzyme cleavage (FIG. 8).

The PCR was carried out under the same conditions described above, the DNA contained in 5 µl portion of the thus obtained DNA solution was cleaved with a restriction enzyme HindIII, the resulting DNA fragments were separated by agarose gel electrophoresis and then a fragment of 0.5 kb was recovered in the same manner. A 0.2 µg portion of the pNT45 DNA obtained by the just described process was cleaved with the restriction enzyme HindIII and subjected to a dephosphorylation treatment with alkaline phosphatase, the resulting DNA fragments were separated by agarose gel electrophoresis and then a fragment of 4.7 kb was recovered in the same manner.

Using a ligation kit, the fragments of 0.5 kb and 4.7 kb were subjected to ligation reaction for 16 hours at 16° C.

Using the ligation reaction solution, *Escherichia coli* NM522 was transformed in accordance with the usual way, and the resulting transformant was spread on LB agar medium containing 50 µg/ml ampicillin and then cultured overnight at 30° C.

By extracting a plasmid from the thus grown colonies of the transformant in accordance with the usual way, glk expression plasmid pNT46 was obtained. Structure of the plasmid was recognized by restriction enzyme cleavage (FIG. 8).

5) Construction of pfkB Expression Plasmid

The sense strand DNA primer shown in SEQ ID NO:15 and the antisence strand DNA primer shown in SEQ ID NO:16 were synthesized. The PCR was carried out using the synthesized DNA strands as primers, and the chromosomal DNA of the strain W3110 as the template, under the same conditions as described in the foregoing.

After completion of the PCR, a precipitate of DNA was obtained by the ethanol precipitation process. The precipitate was dissolved in 20 µl of TE. Using 5 µl portion of the solution, the DNA was cleaved with restriction enzymes HindIII and EcoRV, the resulting DNA fragments were separated by agarose gel electrophoresis and then a fragment of 1.3 kb was recovered using Gene Clean II Kit. A 0.2 µg portion of pBluescript II SR+DNA was cleaved with restriction enzymes HindIII and EcoRV, the resulting DNA fragments were separated by agarose gel electrophoresis and then a fragment of 3.0 kb was recovered in the same manner.

Using a ligation kit, the fragments of 1.3 kb and 3.0 kb were subjected to ligation reaction for 16 hours at 16° C.

Using the ligation reaction solution, *Escherichia coli* NM522 was transformed in accordance with the usual process, and the resulting transformant was spread on LB agar medium containing 50 μg/ml ampicillin and then cultured overnight at 30° C.

Figure 9:
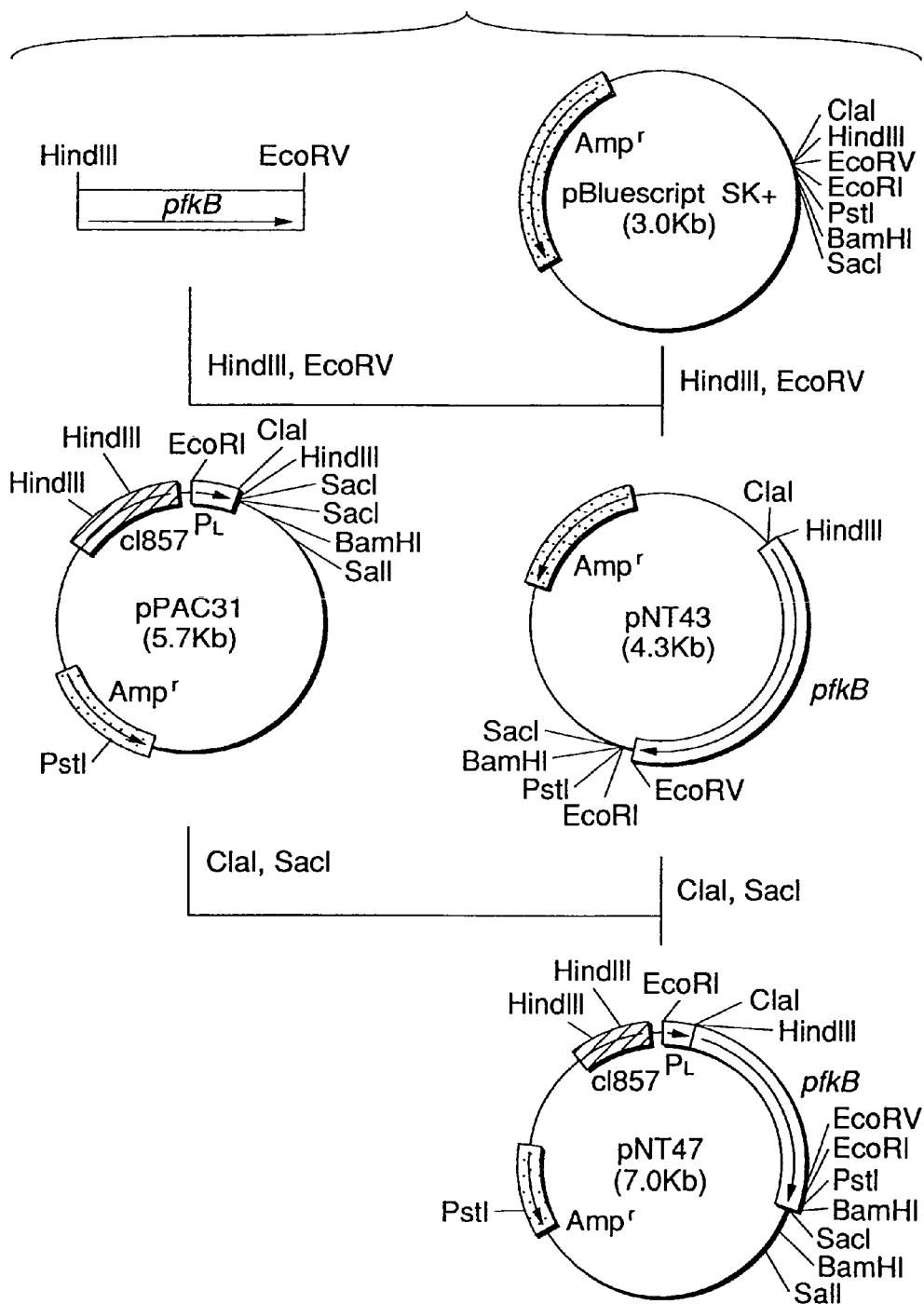
FIG. 9 shows construction steps of pfkB gene expression plasmid pNT47.

By extracting a plasmid from the thus grown colonies of the transformant in accordance with the usual process, plasmid pNT43 containing the pfkB gene was obtained. Structure of the plasmid was recognized by restriction enzyme cleavage (FIG. 9).

A 0.5 μg portion of the pNT43 DNA was cleaved with restriction enzymes ClaI and SacI, the resulting DNA fragments were separated by agarose gel electrophoresis and then a fragment of 1.3 kb was recovered in the same manner.

A 0.2 μg portion of the pPAC31 DNA obtained in Example 1-1) was cleaved with restriction enzymes ClaI and SacI, the resulting DNA fragments were separated by agarose gel electrophoresis and then a fragment of 5.7 kb was recovered in the same manner.

Using a ligation kit, the fragments of 1.3 kb and 5.7 kb were subjected to ligation reaction for 16 hours at 16° C.

Using the ligation reaction solution, *Escherichia coli* NM522 was transformed in accordance with the usual process, and the resulting transformant was spread on LB agar medium containing 50 μg/ml ampicillin and then cultured overnight at 30° C.

By extracting a plasmid from the thus grown colonies of the transformant in accordance with the usual process, pfkB expression plasmid pNT47 was obtained. Structure of the plasmid was recognized by restriction enzyme cleavage (FIG. 9).

Example 8

Production of UDP-GlcNAc

*Escherichia coli* KY8415/pNT14, NM522/pNT24, NM522/pNT44 and NM522/pNT47 obtained in Example 7 were cultured in the same manner as in Example 2, and each of the thus obtained culture broths were centrifuged to obtain wet cells. As occasion demands, these wet cells can be preserved at −20° C. and utilized by thawing the cells prior to use.

A 0.1 ml portion of a reaction solution having a composition of 6 g/l *Escherichia coli* NM522/pNT24 wet cells, 6 g/l NM522/pNT47 wet cells, 100 mM Tris-HCl buffer (pH 8.0), 6 mM $MgCl_2.6H_2O$, 10 mM glucose-6-phosphate, 2.5 mM fructose-6-phosphate, 2.5 mM ATP and 4 g/l Nymeen S-215 was put into a 1.5 ml tube, and 1 hour of the reaction was carried out at 37° C. The reaction solution was treated at 65° C. for 5 minutes and shortage in cells and substances was suspended until 0.3 g/l *Escherichia coli* KY8415/pNT14 wet cells, 6 g/l NM522/pNT44 wet cells, 5 mM glucosamine-6-phosphate, 5 mM acetyl-CoA and 5 mM UTP, and then 30 minutes of the reaction was carried out at 37° C. to find that 2.5 mM (1.6 g/l) UDP-GlcNAc (2Na salt) was formed in the reaction solution. In this connection, when *Escherichia coli* NM522/pNT24 wet cells or NM522/pNT47 wet cells were not added, formed amounts of the UDP-GlcNAc were 0.08 mM and 0.16 mM, respectively.

These results indicate that Glc-1,6-P2 necessary for the expression of glmM activity can be provided by the combination of a pgm expression strain with a pfkB expression strain.

Example 9

Production of UDP-GlcNAc

*Escherichia coli* KY8415/pNT14, NM522/pNT24, NM522/pNT44, NM522/pNT46 and NM522/pNT47 obtained in Example 7 were cultured in the same manner as in Example 2, and each of the thus obtained culture broths was centrifuged to obtain wet cells. Also, *Corynebacterium ammoniagenes* ATCC 21170 was cultured in the same manner as in Example 2, and the thus obtained culture broth was centrifuged to obtain wet cells. As occasion demands, these wet cells can be preserved at −20° C. and utilized by thawing the cells prior to use.

A 30 ml portion of a reaction solution having a composition of 10 g/l wet cells of each of *Escherichia coli* KY8415/pNT14, NM522/pNT24, NM522/pNT44, NM522/pNT47 and NM522/pNT46, 150 g/l *Corynebacterium ammoniagenes* ATCC 21170 wet cells, 50 g/l fructose, 80 g/l glucosamine hydrochloride, 15 g/l $KH_2PO_4$, 5 g/l $MgSO_4.7H_2O$, 5 g/l phytic acid, 10 g/l orotic acid (potassium salt), 4 g/l Nymeen S-215 and 10 ml/l xylene was put into a 200 ml beaker, and 10 hours of the reaction was carried out at 32° C. under stirring the reaction solution with a magnetic stirrer (900 rpm).

During the reaction, pH of the reaction solution was maintained at 7.2 using 4 N NaOH, and fructose and $KH_2PO_4$ were added when required.

By the reaction, 6.2 g/l UDP-GlcNAc (2Na salt) was formed in the reaction solution.

Example 10

Construction of galK Expression Plasmid

A 0.5 μg portion of the pNT25 DNA obtained in Example 3-1) was cleaved with restriction enzymes ClaI and EcoRV, the resulting DNA fragments were separated by agarose gel electrophoresis and then a fragment of 6.7 kb was recovered using Gene Clean II kit. The thus recovered DNA was blunt-ended using DNA Blunting Kit and then subjected to ligation reaction for 16 hours at 16° C. using a ligation kit.

Using the ligation reaction solution, *Escherichia coli* NM522 was transformed in accordance with the usual process, and the resulting transformant was spread on LB agar medium containing 50 μg/ml ampicillin and then cultured overnight at 30° C.

Figure 10:
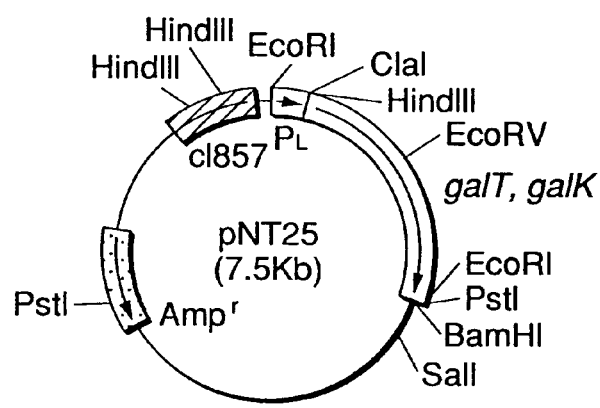
FIG. 10 shows construction steps of galK gene expression plasmid pNT54.
Figure 10:
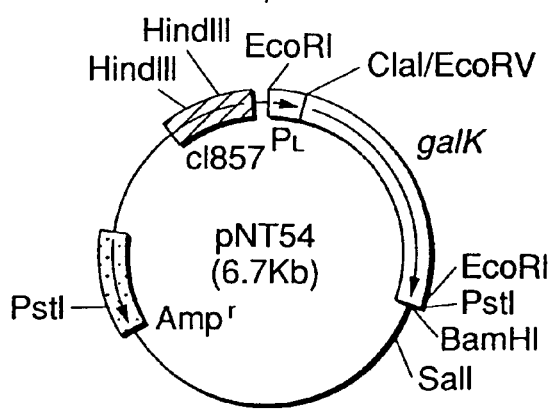

By extracting a plasmid from the thus grown colonies of the transformant in accordance with the usual process, galK expression plasmid pNT54 was obtained. Structure of the plasmid was recognized by restriction enzyme cleavage (FIG. 10).

Example 11

Production of UDP-GlcNAc

*Escherichia coli* NM522/pNT54 obtained in Example 10 was cultured in the same manner as in Example 2, and the culture broth was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 50 g/l *Escherichia coli* NM522/pNT54 wet cells, 150 g/l *Corynebacterium ammoniagenes* ATCC 21170 wet cells, 40 g/l fructose, 67 g/l N-acetylglucosamine, 15 g/l $KH_2PO_4$, 5 g/l $MgSO_4.7H_2O$, 5 g/l phytic acid, 10 g/l orotic acid (potassium salt), 4 g/l Nymeen S-215 and 10 ml/l xylene was put into a 200 ml beaker, and 27 hours of the reaction was carried out at 32° C. under stirring the reaction solution with a magnetic stirrer (900 rpm).

During the reaction, pH of the reaction solution was maintained at 7.2 using 4 N NaOH, and fructose and $KH_2PO_2$ were added when required.

By the reaction, 17.1 g/l UDP-GlcNAc (2Na salt) was formed in the reaction solution.

Example 12

Simultaneous Production of UDP-GlcNAc and UDP-Gal

The strain NM522/pNT25 obtained in Example 3 was cultured in the same manner as in Example 2, and the culture broth was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 25 g/l *Escherichia coli* NM522/pNT25 wet cells, 150 g/l *Corynebacterium ammoniagenes* ATCC 21170 wet cells, 60 g/l fructose, 50 g/l N-acetylglucosamine, 40 g/l galactose, 15 g/l $KH_2PO_4$, 5 g/l $MgSO_4.7H_2O$, 5 g/l phytic acid, 10 g/l orotic acid (potassium salt), 4 g/l Nymeen S-215 and 10 ml/l xylene was put into a 200 ml beaker, and 24 hours of the reaction was carried out at 32° C. under stirring the reaction solution with a magnetic stirrer (900 rpm).

During the reaction, pH of the reaction solution was maintained at 7.2 using 4 N NaOH, and $KH_2PO_4$ was added when required.

By the reaction, 11.4 g/l UDP-GlcNAc (2Na salt) and 18 g/l UDP-Gal (2Na salt) were formed in the reaction solution.

Example 13

Construction of Plasmid Capable of Expressing manB, manC, pgm and pfkB

1) Construction of manB, manC Expression Plasmid

The sense strand DNA primer shown in SEQ ID NO:17 and the antisence strand DNA primer shown in SEQ ID NO:18 were synthesized. The PCR was carried out using the synthesized DNA strands as primers, and the chromosomal DNA of *Escherichia coli* W3110 as the template, under the same conditions as described in the foregoing.

After completion of the PCR treatment, a precipitate of DNA was obtained by the ethanol precipitation process. The precipitate was dissolved in 20 μl of TE. Using 5 μl portion of the solution, the DNA was cleaved with restriction enzymes HindIII and BamHI, the resulting DNA fragments were separated by agarose gel electrophoresis and then a fragment of 3.0 kb was recovered using Gene Clean II Kit. A 0.2 μg portion of pBluescript II SK+ DNA was cleaved with restriction enzymes HindIII and BamHI, the resulting DNA fragments were separated by agarose gel electrophoresis and then a fragment of 3.0 kb was recovered in the same manner.

Using a ligation kit, both of the fragments of 3.0 kb were subjected to ligation reaction for 16 hours at 16° C.

Using the ligation reaction solution, *Escherichia coli* N522 was transformed in accordance with the usual process, and the resulting transformant was spread on LB agar medium containing 50 μg/ml ampicillin and then cultured overnight at 30° C.

Figure 11:
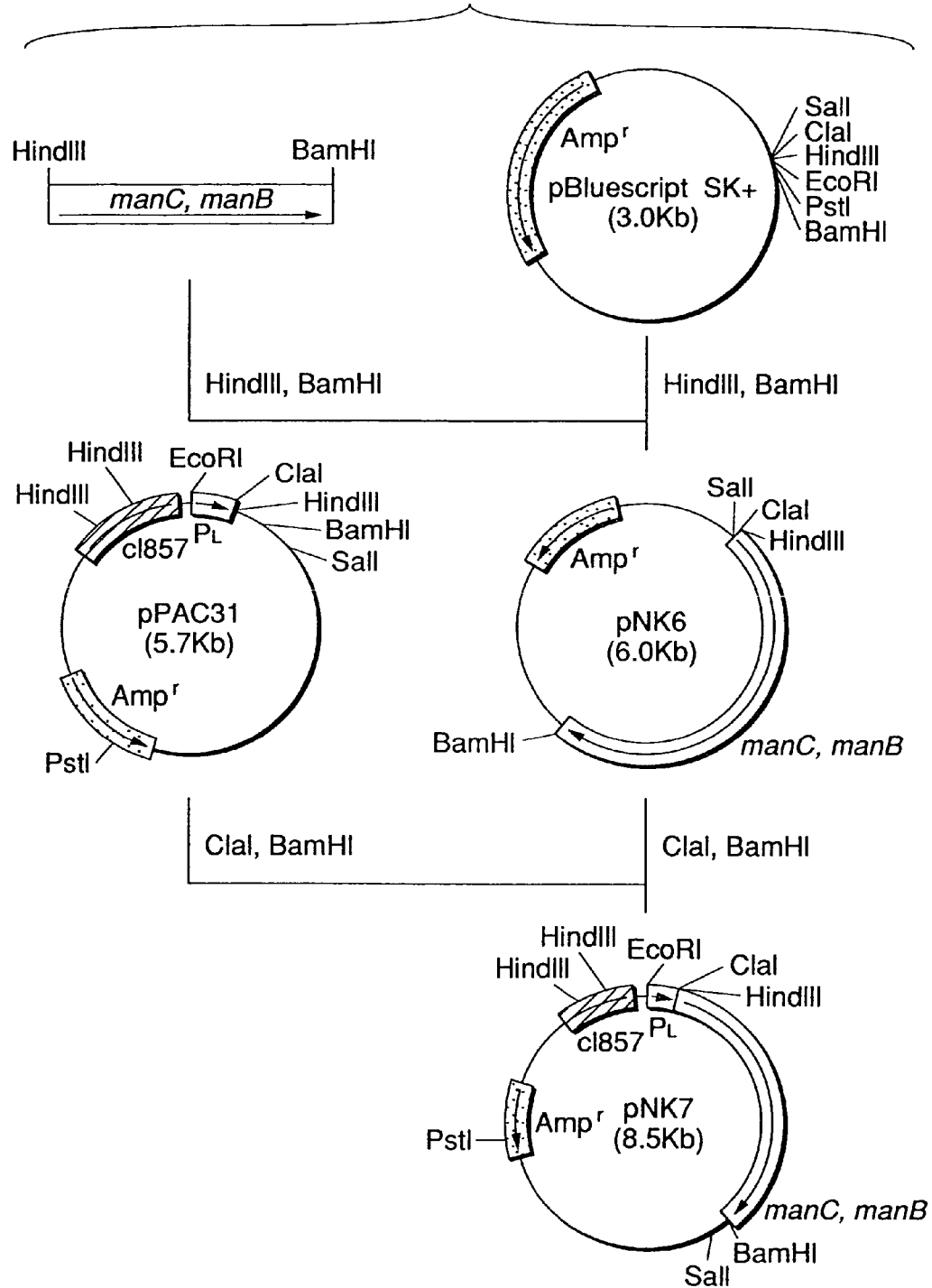
FIG. 11 shows construction steps of manB, manC gene expression plasmid pNK7.

By extracting a plasmid from the thus grown colonies of the transformant in accordance with the above-mentioned known process, plasmid pNK6 containing manC and manB was obtained. Structure of the plasmid was recognized by restriction enzyme cleavage (FIG. 11).

A 0.5 μg portion of the pNK6 DNA was cleaved with restriction enzymes ClaI and BamHI, the resulting DNA fragments were separated by agarose gel electrophoresis and then a fragment of 3.0 kb was recovered. A 0.2 μg portion of pPAC31 DNA obtained in Example 1-1) was cleaved with restriction enzymes ClaI and BamHI, the resulting DNA fragments were separated by agarose gel electrophoresis and then a fragment of 5.5 kb was recovered.

Using a ligation kit, the fragments of 3.0 kb and 5.5 kb were subjected to ligation reaction for 16 hours at 16° C.

Using the ligation reaction solution, *Escherichia coli* NM522 was transformed in accordance with the usual process, and the resulting transformant was spread on LB agar medium containing 50 μg/ml ampicillin and then cultured overnight at 30° C.

By extracting a plasmid from the thus grown colonies of the transformant in accordance with the usual process, manC, manB expression plasmid pNK7 was obtained. Structure of the plasmid was recognized by restriction enzyme cleavage (FIG. 11).

2) Construction of pgm, pfkB Simultaneous Expression Plasmid

A 0.5 μg portion of the pNT24 DNA obtained in Example 7 was cleaved with restriction enzymes XhoI and BamHI, the resulting DNA fragments were separated by agarose gel electrophoresis and then a fragment of 3.0 kb was recovered using Gene Clean II Kit. On the other hand, a 0.2 μg portion of pSTV28 DNA (manufactured by Takara Shuzo Co., Ltd.) was cleaved with restriction enzymes SalI and BamHI, the resulting DNA fragments were separated by agarose gel electrophoresis and then a fragment of 3.0 kb was recovered in the same manner.

Using a ligation kit, both of the fragments of 3.0 kb were subjected to ligation reaction for 16 hours at 16° C.

Using the ligation reaction solution, *Escherichia coli* NM522 was transformed in accordance with the usual process, and the resulting transformant was spread on LB agar medium containing 10 μg/ml chloramphenicol and then cultured overnight at 30° C.

Figure 12:
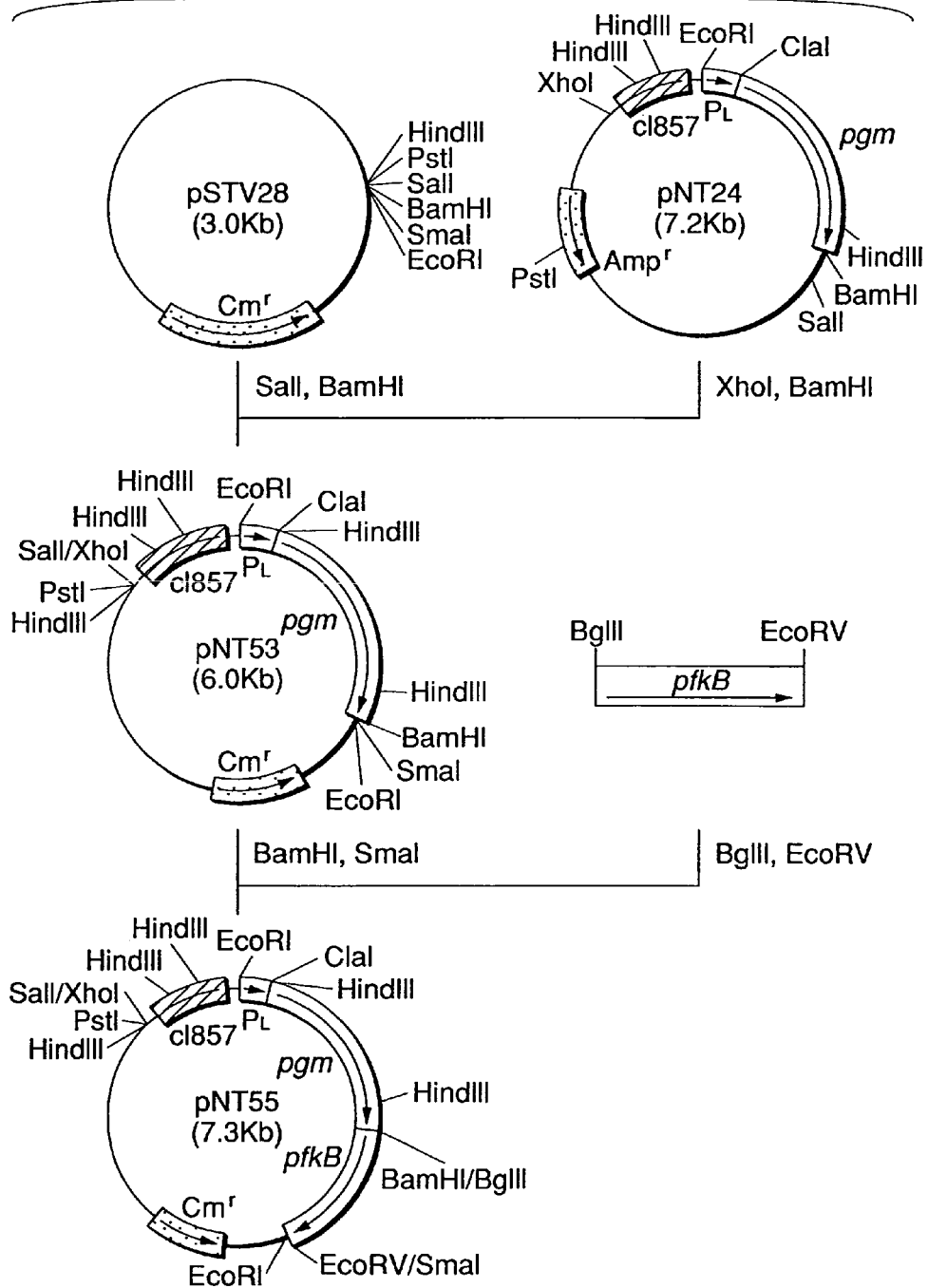
FIG. 12 shows construction steps of pgm, pfkB gene expression plasmid pNT55.

By extracting a plasmid from the thus grown colonies of the transformant in accordance with the usual process, plasmid pNT53 containing the pgm gene was obtained. Structure of the plasmid was recognized by restriction enzyme cleavage (FIG. 12).

The sense strand DNA primer shown in SEQ ID NO:19 was synthesized, and the PCR was carried out using the sense strand DNA primer and the antisence strand DNA primer shown in SEQ ID NO:16, and the pNT47 DNA obtained in Example 7 as the template, under the same conditions as described in the foregoing.

After completion of the PCR, a precipitate of DNA was obtained by the ethanol precipitation process. The precipitate was dissolved in 20 μl of TE. Using 5 μl portion of the solution, the DNA was cleaved with restriction enzymes EcoRV and BglII, the resulting DNA fragments were separated by agarose gel electrophoresis and then a fragment of 1.3 kb was recovered in the same manner. A 0.2 μg portion of pNT53 DNA was cleaved with restriction enzymes SmaI and BamHI, the resulting DNA fragments were separated by agarose gel electrophoresis and then a fragment of 6.0 kb was recovered in the same manner.

Using a ligation kit, the fragments of 1.3 kb and 6.0 kb were subjected to ligation reaction for 16 hours at 16° C.

Using the ligation reaction solution, *Escherichia coli* NM522 was transformed in accordance with the usual process, and the resulting transformant was spread on LB agar medium containing 10 µg/ml chloramphenicol and cultured overnight at 30° C.

By extracting a plasmid from the thus grown colonies of the transformant in accordance with the usual process, plasmid pNT55 capable of expressing pgm and pfkB was obtained. Structure of the plasmid was recognized by restriction enzyme cleavage (FIG. 12).

Example 14

Production of GDP-Man

1) Preparation of manB, manC, pgm, pfkB Expression Strain

Using the pNT55 DNA obtained in Example 13-2), *Escherichia coli* NM522/pNK7 was transformed in accordance with the usual process, and the resulting transformant was spread on LB agar medium containing 50 µg/ml ampicillin and 10 µg/ml chloramphenicol and cultured overnight at 30° C. By selecting the thus grown transformants, *Escherichia coli* NM522/pNK7/pNT55 was obtained as a manB, manC, pgm, pfkB expression strain.

2) Production of GDP-Man

*Escherichia coli* NM522/pNK7/pNT55 obtained in the above step 1) and *Escherichia coli* NM522/pNT46 obtained in Example 7 were cultured separately in the same manner as in Example 2, and each of thus obtained the culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 25 g/l *Escherichia coli* NM522/pNK7/pNT55 wet cells, 25 g/l the NM522/pNT46 wet cells, 150 g/l *Corynebacterium ammoniagenes* ATCC 21170 wet cells, 60 g/l fructose, 50 g/l mannose, 15 g/l $KH_2PO_4$, 5 g/l $MgSO_4.7H_2O$, 5 g/l phytic acid, 60 g/l GMP (2Na, $7H_2O$ salt), 4 g/l Nymeen S-215 and 10 ml/l xylene was put into a 200 ml beaker, and 24 hours of the reaction was carried out under stirring the reaction solution with a magnetic stirrer (900 rpm).

During the reaction, pH of the reaction solution was maintained at 7.2 using 4 N NaOH, and $KH_2PO_4$ was added when required.

By the reaction, 14.6 g/l GDP-Man (2Na, $1H_2O$ salt) was formed in the reaction solution.

Example 15

Construction of gmd, wcaG Expression Plasmid

The sense strand DNA primer shown in SEQ ID NO:20 and the antisence strand DNA primer shown in SEQ ID NO:21 were synthesized. The PCR was carried out using the synthesized DNA strands as primers, and the chromosomal DNA of *Escherichia coli* W3110 as the template, under the same conditions as described in the foregoing.

After completion of the PCR, a precipitate of DNA was obtained by the ethanol precipitation process. The precipitate was dissolved in 20 µl of TE. Using 5 µl portion of the solution, the DNA was cleaved with restriction enzymes HindIII and XhoI, the resulting DNA fragments were separated by agarose gel electrophoresis and then a fragment of 2.3 kb was recovered using Gene Clean II Kit.

A 0.2 µg portion of the pPA31 DNA obtained in Example 1-1) was cleaved with restriction enzymes HindIII and SalI, the resulting DNA fragments were separated by agarose gel electrophoresis and then a fragment of 3.9 kb was recovered in the same manner.

Using a ligation kit, the fragments of 2.3 kb and 3.9 kb were subjected to ligation reaction for 16 hours at 16° C.

Using the ligation reaction solution, *Escherichia coli* NM522 was transformed in accordance with the usual process, and the resulting transformant was spread on LB agar medium containing 50 µg/ml ampicillin and then cultured overnight at 30° C.

Figure 13:
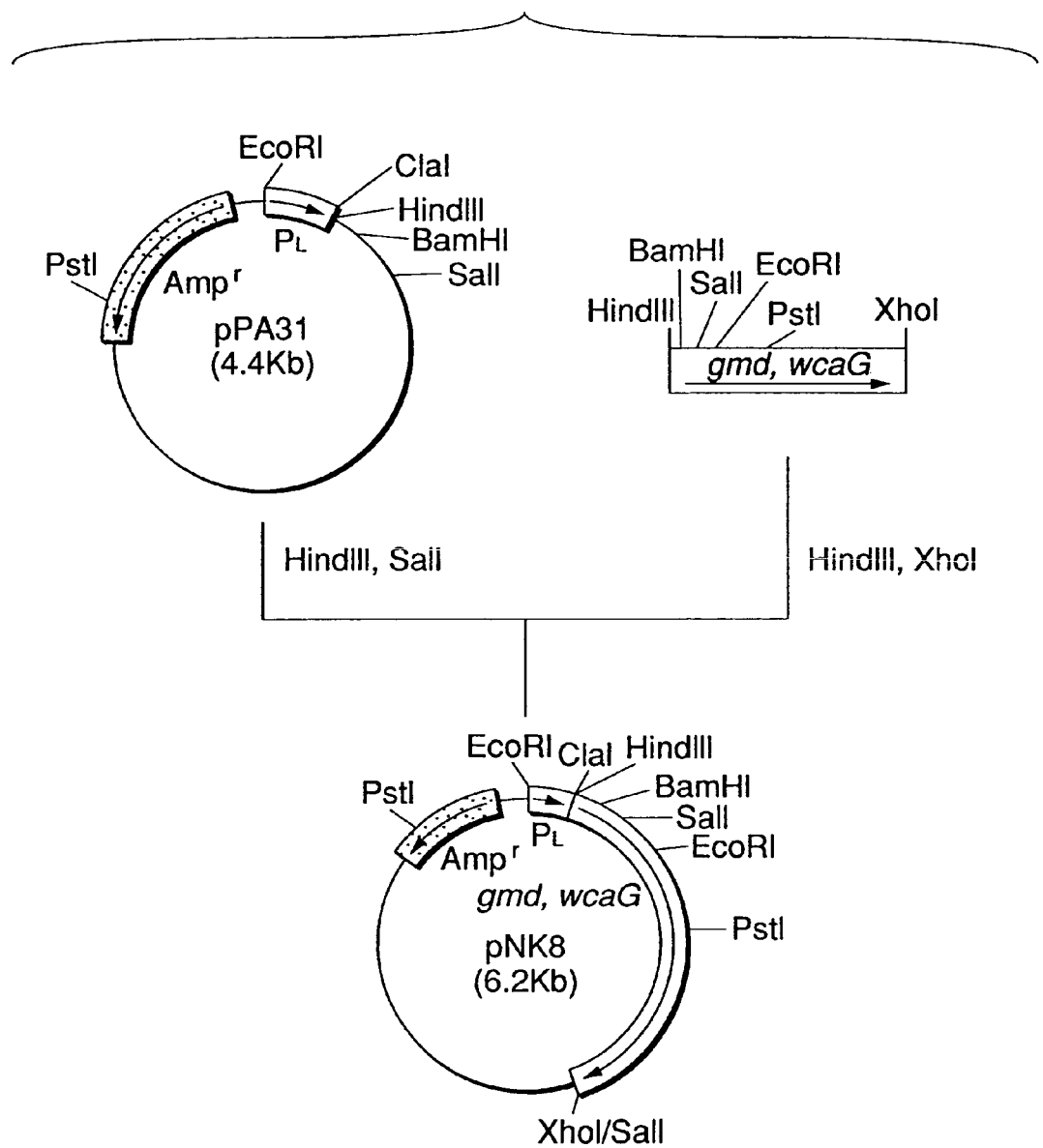
FIG. 13 shows construction steps of gmd, wcaG gene expression plasmid pNK8.

By extracting a plasmid from the thus grown colonies of the transformant in accordance with the usual process, plasmid pNK8 containing gmd and wcaG was obtained. Structure of the plasmid was recognized by restriction enzyme cleavage (FIG. 13).

Example 16

Production of GDP-Fuc

*Escherichia coli* NM522/pNK7/pNT55 obtained in Example 14, NM522/pNK8 obtained in Example 15 and NH522/pNT46 obtained in Example 7 were cultured in the same manner as in Example 2, and each of the thus obtained culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 25 g/l *Escherichia coli* NM522/pNK7/pNT55 wet cells, 25 g/l *Escherichia coli* NM522/pNK8 wet cells, 25 g/l *Escherichia coli* NM522/pNT46 wet cells, 150 g/l *Corynebacterium ammoniagenes* ATCC 21170 wet cells, 40 g/l fructose, 60 g/l mannose, 15 g/l $KH_2PO_4$, 5 g/l $MgSO_4.7H_2O$, 5 g/l phytic acid, 60 g/l GMP (2Na/$7H_2O$ salt), 4 g/l Nymeen S-215 and 10 ml/l xylene was put into a 200 ml beaker, and 24 hours of the reaction was carried out at 32° C. under stirring the reaction solution with a magnetic stirrer (900 rpm).

During the reaction, pH of the reaction solution was maintained at 7.2 using 4 N NaOH, and $KH_2PO_4$ was added when required.

By the reaction, 1.0 g/l GDP-Fuc (2.5Na, $1H_2O$ salt) was formed in the reaction solution.

Example 17

Construction of neuA Expression Plasmid

Chromosomal DNA of *Escherichia coli* K235 (ATCC 13027) was prepared in the same manner as in Example 1.

The sense strand DNA primer shown in SEQ ID NO:22 and the antisence strand DNA primer shown in SEQ ID NO:23 were synthesized. The PCR was carried out using the synthesized DNA strands as primers, and the chromosomal DNA of *Escherichia coli* K235 (ATCC 13027) as the template, under the same conditions as described in the foregoing.

After completion of the PCR treatment, a precipitate of DNA was obtained by the ethanol precipitation process. The precipitate was dissolved in 20 µl of TE. Using 5 µl portion of the solution, the DNA was cleaved with restriction enzymes EcoRI and BamHI, the resulting DNA fragments were separated by agarose gel electrophoresis and then a fragment of 1.3 kb was recovered using Gene Clean II Kit. A 0.2 µg portion of pBluescript II SK+ DNA was cleaved with restriction enzymes EcoRI and BamHI, the resulting DNA fragments were separated by agarose gel electrophoresis and then a fragment of 3.0 kb was recovered in the same manner.

Using a ligation kit, the fragments of 1.3 kb and 3.0 kb were subjected to ligation reaction for 16 hours at 16° C.

Using the ligation reaction solution, *Escherichia coli* NM522 was transformed in accordance with the usual process, and the resulting transformant was spread on LB agar medium containing 50 µg/ml ampicillin and then cultured overnight at 30° C.

Figure 14:
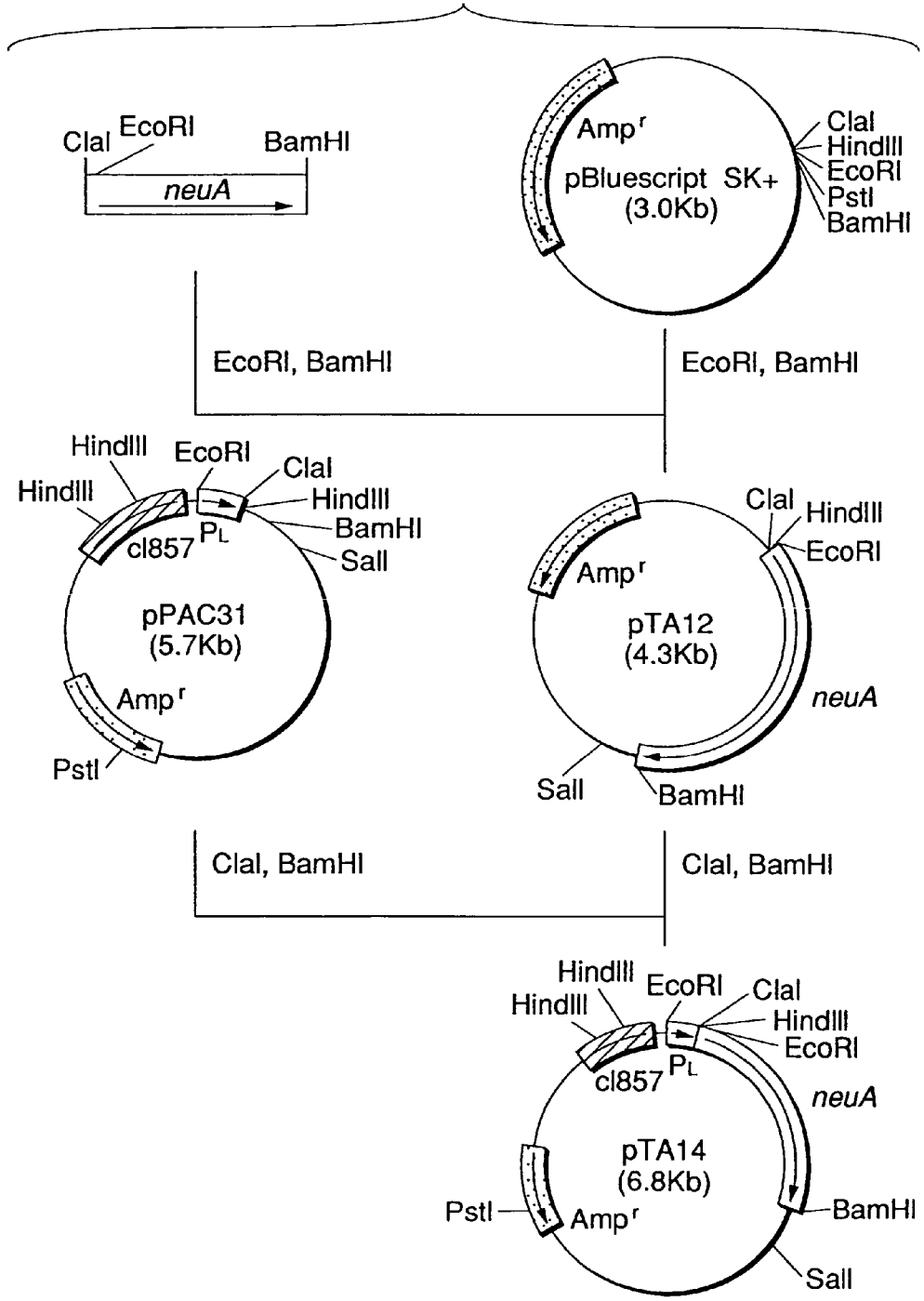
FIG. 14 shows construction steps of neuA gene expression plasmid pTA14.

By extracting a plasmid from the thus grown colonies of the transformant in accordance with the usual process, plasmid pTA12 containing the neuA gene was obtained. Structure of the plasmid was recognized by restriction enzyme cleavage (FIG. 14).

A 0.5 µg portion of the pTA12 DNA was cleaved with restriction enzymes ClaI and BamHI, the resulting DNA fragments were separated by agarose gel electrophoresis and then a fragment of 1.3 kb was recovered in the same manner. A 0.2 µg portion of the pPAC31 DNA obtained in Example 1-1) was cleaved with restriction enzymes ClaI and BamHI, the resulting DNA fragments were separated by agarose gel electrophoresis and then a fragment of 5.5 kb was recovered in the same manner.

Using a ligation kit, the fragments of 1.3 kb and 5.5 kb were subjected to ligation reaction for 16 hours at 16° C.

Using the ligation reaction solution, *Escherichia coli* NM522 was transformed in accordance with the usual process, and the resulting transformant was spread on LB agar medium containing 50 µg/ml ampicillin and then cultured overnight at 30° C.

By extracting a plasmid from the thus grown colonies of the transformant in accordance with the usual process, neuA expression plasmid pTA14 was obtained. Structure of the plasmid was recognized by restriction enzyme cleavage (FIG. 14).

Example 18

Production of CMP-NeuAc

*Escherichia coli* NM522/pTA14 obtained in Example 17, C600/pNAL1 (*Appl. Eviron. Microbiol.*, 51, 562 (1986)) and JF646/pMW5 (*J. Biol. Chem.*, 261, 5568 (1986)) were separately cultured in the same manner as in Example 2, and each of the thus obtained culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 50 g/l *Escherichia coli* NM522/pTA14 wet cells, 15 g/l *Escherichia coli* C600/pNAL1 wet cells, 25 g/l *Escherichia coli* JF646/pMW5 wet cells, 150 g/l *Corynebacterium ammoniagenes* ATCC 21170 wet cells, 10 g/l orotic acid (potassium salt), 20 g/l pyruvic acid (Na salt), 40 g/l fructose, 10 g/l N-acetylmannosamine, 15 g/l $KH_2PO_4$, 5 g/l $MgSO_4 \cdot 7H_2O$, 5 g/l phytic acid, 4 g/l Nymeen S-215 and 10 ml/l xylene was put into a 200 ml beaker, and 24 hours of the reaction was carried out at 32° C. under stirring the reaction solution with a magnetic stirrer (900 rpm).

During the reaction, pH of the reaction solution was maintained at 7.2 using 4 N NaOH, and $KH_2PO_4$ was added when required.

By the reaction, 2.7 g/l CMP-NeuAc (Na salt) was formed in the reaction solution.

Example 19

Production of Lacto-N-tetraose

1) Preparation of β1,3-galactosyltransferase

Namalwa cell line KJM-1 transformed with plasmic pAMoERSAW1 (Japanese Published Unexamined Patent Application No. 181759/94) containing a gene encoding a fusion protein of the IgG binding region of protein A with β1,3-galactosyltransferase was suspended in 30 ml of RPMI1640•ITPSGF medium containing 0.5 mg/ml G418 (manufactured by Gibco), to a density of $5 \times 10^4$ cells/ml, and cultured at 37° C. for 8 days in a $CO_2$ incubator.

Cells were removed from the culture broth by centrifugation, and the supernatant was recovered. As occasion demands, the supernatant can be stored at −80° C. and utilized by thawing the supernatant prior to use.

To the culture supernatant in which the fusion protein of the IgG binding region of protein A with β1,3-galactosyltransferase has been formed were added sodium azide to a final concentration of 0.1% and then 50 µl of IgG Sepharose (manufactured by Pharmacia) which has been pre-treated in accordance with the manufacturer's instructions. The mixture was stirred overnight gently at 4° C.

After the stirring, the β1,3-galactosyltransferase-linked IgG Sepharose was recovered by centifiguration and washed three times with 1 ml of RPMI1640•ITPSGF medium, and then the IgG Sepharose was used as the enzyme source of β1,3-galactosyltransferase.

2) Production of Lacto-N-tetraose

Lacto-N-neotetraose (manufactured by Oxford Glycosystems) was fluorescence-labeled by 2-aminopyridine in accordance with a known process (*Agric. Biol. Chem.*, 54, 2169 (1990)) and mixed with 0.1 U β-galactosidase (manufactured by Seikagaku Kogyo K. K.), and then the mixture was allowed to react for 16 hours at 37° C. to remove the galactose at the non-reducing end.

The reaction solution was heated at 100° C. for 5 minutes to inactivate β-galactosidase.

GlcNAcβ1-3Galβ1-4Glc obtained by the reaction was used as a complex carbohydrate precursor.

A 36 µl portion of a reaction solution containing 0.5 mM of the complex carbohydrate precursor, 0.5 U the β1,3-galactosyltransferase linked IgG Sepharose obtained in the above step 1), 6 µl of a reaction solution containing UDP-Gal (5 mM) obtained in Example 4, 100 mM Tris-HCl (pH 7.9), 10 mM $MnCl_2$ and 2 mM β-mercaptoethanol was allowed to stand for 65 hours at 32° C. to effect the reaction.

After completion of the reaction, amount of the product accumulated in the reaction solution was measured by HPLC under the following conditions:

Column:
  TSK gel ODS-80TM column (4.6 mm×30 cm, manufactured by TOSOH CORPORATION)
Liquid phase:
  0.02 M ammonium acetate buffer (pH 4.0)
Temperature:
  50° C.
Flow rate:
  1 ml/min Detection:

Fluorescence detector (excitation wavelength 320 nm, radiation wavelength 400 nm)

Identification of the product was carried out by comparing elution time of aminopyridine-labeled lacto-N-tetraose with that of the labeled product.

By the reaction, 0.17 mM (0.12 g/l) lacto-N-tetraose was formed.

Example 20

Production of Lacto-N-neotetraose

In the same manner as in Example 19, GlcNAcβ1-3 Galβ1-4Glc was prepared from lacto-N-neotetraose and used as a complex carbohydrate precursor.

A 36 µl 1 portion of a reaction solution containing 0.5 mM of the complex carbohydrate precursor, 0.5 U β1,4-galactosyltransferase (manufactured by Sigma), 6 µl of a reaction solution containing UDP-Gal (5 mM obtained in Example 4, 100 mM Tris-HCl buffer (pH 7.9), 10 mM $MnCl_2$ and 2 mM β-mercaptoethanol was allowed to stand for 65 hours at 32° C. to effect the reaction.

After completion of the reaction, amount of the product accumulated in the reaction solution was measured by HPLC under the same conditions of Example 19-2). Identification of the product was carried out by comparing elution time of the aminopyridine-labeled lacto-N-neotetraose with that of the product.

By the reaction, 0.15 mM (0.11 g/l) lacto-N-neotetraose was formed.

Example 21

Production of Lacto-N-fucopentaose III

IgG Sepharose-linked α1,3-fucosyltransferase was prepared from namalwa cell line KJM-1 transformed with plasmid pAMoA-FT6 (*J. Biol. Chem.*, 269, 14730 (1994)) containing a gene encoding a fusion protein of the IgG binding region of protein A with α1,3-fucosyltransferase, in the same manner as in Example 19-1), and used as the enzyme source of α1,3-fucosyltransferase.

A 50 µl portion of a reaction solution containing 0.25 mM lacto-N-neotetraose (manufactured by Oxford Glycosystems), 1.0 U of the IgG Sepharose-linked α1,3-fucosyltransferase, 6 µl of a reaction solution containing GDP-Fuc (0.25 mM) obtained in Example 16, 100 mM Tris-HCl buffer (pH 7.9) and 10 mM $MnCl_2$ was allowed to stand for 24 hours at 37° C. to effect the reaction.

After completion of the reaction, amount of the product accumulated in the reaction solution was measured using a sugar analyzer (DX-500) manufactured by Dionex. Identification of the product was carried out by comparing elution time of lacto-N-fucopentaose III (manufactured by Oxford Glycosystems) with that of the product.

By the reaction, 0.21 mM (0.18 g/1) lacto-N-fucopentaose III was formed.

Example 22

Construction of α1,4-galactosyltransferase (lgtC) Expression Plasmid

Chromosomal DNA of *Neisseria gonorrhoeae* (ATCC 33084) was prepared in the same manner as in Example 1.

The sense strand DNA primer shown in SEQ ID NO:24 and the antisence strand DNA primer shown in SEQ ID NO:25 were synthesized. The PCR was carried out using the synthesized DNA strands as primers, and the chromosomal DNA of *Neisseria gonorrhoeae* (ATCC 33084) as the template, under the same conditions as described in the foregoing.

After completion of the PCR treatment, a precipitate of DNA was obtained by the ethanol precipitation process. The precipitate was dissolved in 20 µl of TE. Using 5 µl portion of the solution, the DNA was cleaved with restriction enzymes HindIII and BamHI, the resulting DNA fragments were separated by agarose gel electrophoresis and then a fragment of 1.0 kb was recovered using Gene Clean II Kit. A 0.2 µg portion of the pPA31 DNA obtained in Example 1-1) was cleaved with restriction enzymes HindIII and BamHI, the resulting DNA fragments were separated by agarose gel electrophoresis and then a fragment of 4.2 kb was recovered in the same manner.

Using a ligation kit, the fragments of 1.0 kb and 4.2 kb were subjected to ligation reaction for 16 hours at 16° C.

Using the ligation reaction solution, *Escherichia coli* NM522 was transformed in accordance with the usual process, and the resulting transformant was spread on LB agar medium containing 50 µg/ml ampicillin and then cultured overnight at 30° C.

Figure 15:
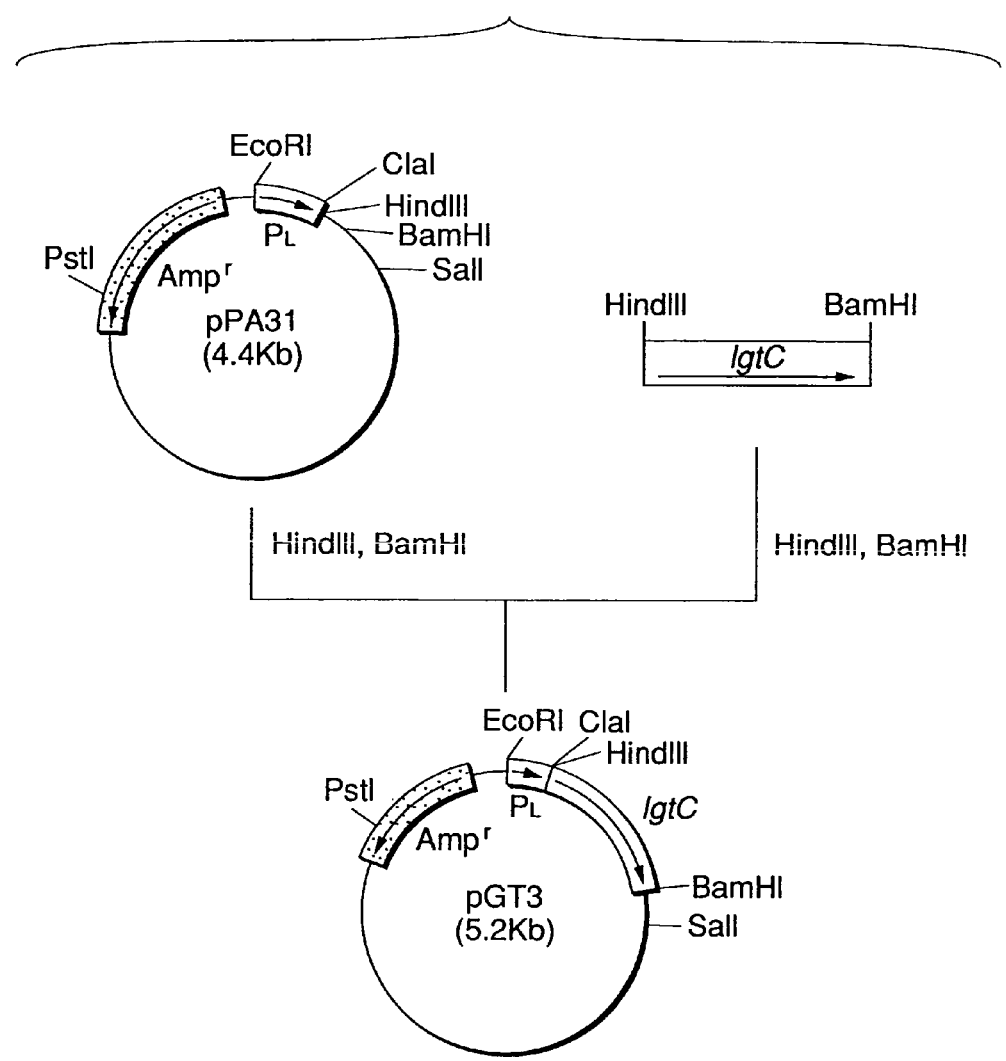
FIG. 15 shows construction steps of lgtC gene expression plasmid pGT3.

By extracting a plasmid from the thus grown colonies of the transformant in accordance with the usual process, a lgtC expression plasmid pGT3 was obtained. Structure of the plasmid was recognized by restriction enzyme cleavage (FIG. 15).

Example 23

Production of Globotriose

*Escherichia coli* NM522/pNT25/pNT32 obtained in Example 4 and *Escherichia coli* NM522/pGT3 obtained in Example 22 were cultured in the same manner as in Example 2, and each of the thus obtained culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 50 g/l *Escherichia coli* NM522/pNT25/pNT32 wet cells, 50 g/l *Escherichia coli* NM522/pGT3 wet cells, 150 g/l *Corynebacterium ammoniagenes* ATCC 21170 wet cells, 100 g/l fructose, 100 g/l galactose, 100 g/l lactose, 15 g/l $KH_2PO_4$, 5 g/l $MgSO_4.7H_2O$, 5 g/l phytic acid, 10 g/l orotic acid (potassium salt), 4 g/l Nymeen S-215 and 10 ml/l xylene was put into a 200 ml beaker, and 36 hours of the reaction was carried out at 32° C. under stirring the reaction solution with a magnetic stirrer (900 rpm).

During the reaction, pH of the reaction solution was maintained at 7.2 using 4 N NaOH, and galactose, lactose, fructose and $KH_2PO_4$ were added when required.

By the reaction, 188 g/l globotriose was formed in the reaction solution.

Cells were removed from the reaction solution by centrifugation, and a 10 ml portion of the thus obtained supernatant was purified by employing a process in which activated carbon was used, thereby obtaining 1.5 g of globotriose as white powder.

Example 24

Production of Galα1-4Galβ1-4GlcNAc

*Escherichia coli* NM522/pNT25/pNT32 obtained in Example 4 and *Escherichia coli* NM522/pGT3 obtained in Example 22 were cultured in the same manner as in Example 2, and each of the thus obtained culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 50 g/l *Escherichia coli* NM522/pNT25/pNT32 wet cells, 50 g/l *Escherichia coli* NM522/pGT3 wet cells, 150 g/l *Corynebacterium ammoniagenes* ATCC 21170 wet cells, 50 g/l fructose, 50 g/l galactose, 96 g/l N-acetyllactosamine, 15 g/l $KH_2PO_4$, 5 g/l $MgSO_4 \cdot 7H_2O$, 5 g/l phytic acid, 10 g/l orotic acid (potassium salt), 4 g/l Nymeen S-215 and 10 ml/l xylene was put into a 200 ml beaker, and 23 hours of the reaction was carried out at 32° C. under stirring the reaction solution with a magnetic stirrer (900 rpm).

During the reaction, pH of the reaction solution was maintained at 7.2 using 4 N NaOH, and galactose, fructose and $KH_2PO_4$ were added when required.

By the reaction, 10 g/l Galα1-4Galβ1-4GlcNAc was formed in the reaction solution.

Cells were removed from the reaction solution by centrifugation, and the formed product was purified from a 30 ml portion of the thus obtained supernatant by employing a process in which activated carbon was used, thereby obtaining 0.2 g of Galα1-4Galβ1-4GlcNAc as white powder.

Example 25

Construction of β1,4-galactosyltransferase (lgtB) Expression Plasmid

The sense strand DNA primer shown in SEQ ID NO:26 and the antisence strand DNA primer shown in SEQ ID NO:27 were synthesized. The PCR was carried out using the synthesized DNA strands as primers, and the chromosomal DNA of *N. gonorrhoeae* (ATCC 33084) as the template, under the same conditions as described in the foregoing.

After completion of the PCR treatment, a precipitate of DNA was obtained by the ethanol precipitation process. The precipitate was dissolved in 20 µl of TE. Using 5 µl portion of the solution, the DNA was cleaved with restriction enzymes HindIII and BamHI, the resulting DNA fragments were separated by agarose gel electrophoresis and then a fragment of 0.8 kb was recovered using Gene Clean II Kit. A 0.2 µg portion of pBluescript II SK+ DNA was cleaved with restriction enzymes HindIII and BamHI, the resulting DNA fragments were separated by agarose gel electrophoresis and then a fragment of 3.0 kb was recovered in the same manner.

Using a ligation kit, the fragments of 0.8 kb and 3.0 kb were subjected to ligation reaction for 16 hours at 16° C.

Using the ligation reaction solution, *Escherichia coli* NM522 was transformed in accordance with the usual process, and the resulting transformant was spread on LB agar medium containing 50 µg/ml ampicillin and then cultured overnight at 30° C.

Figure 16:
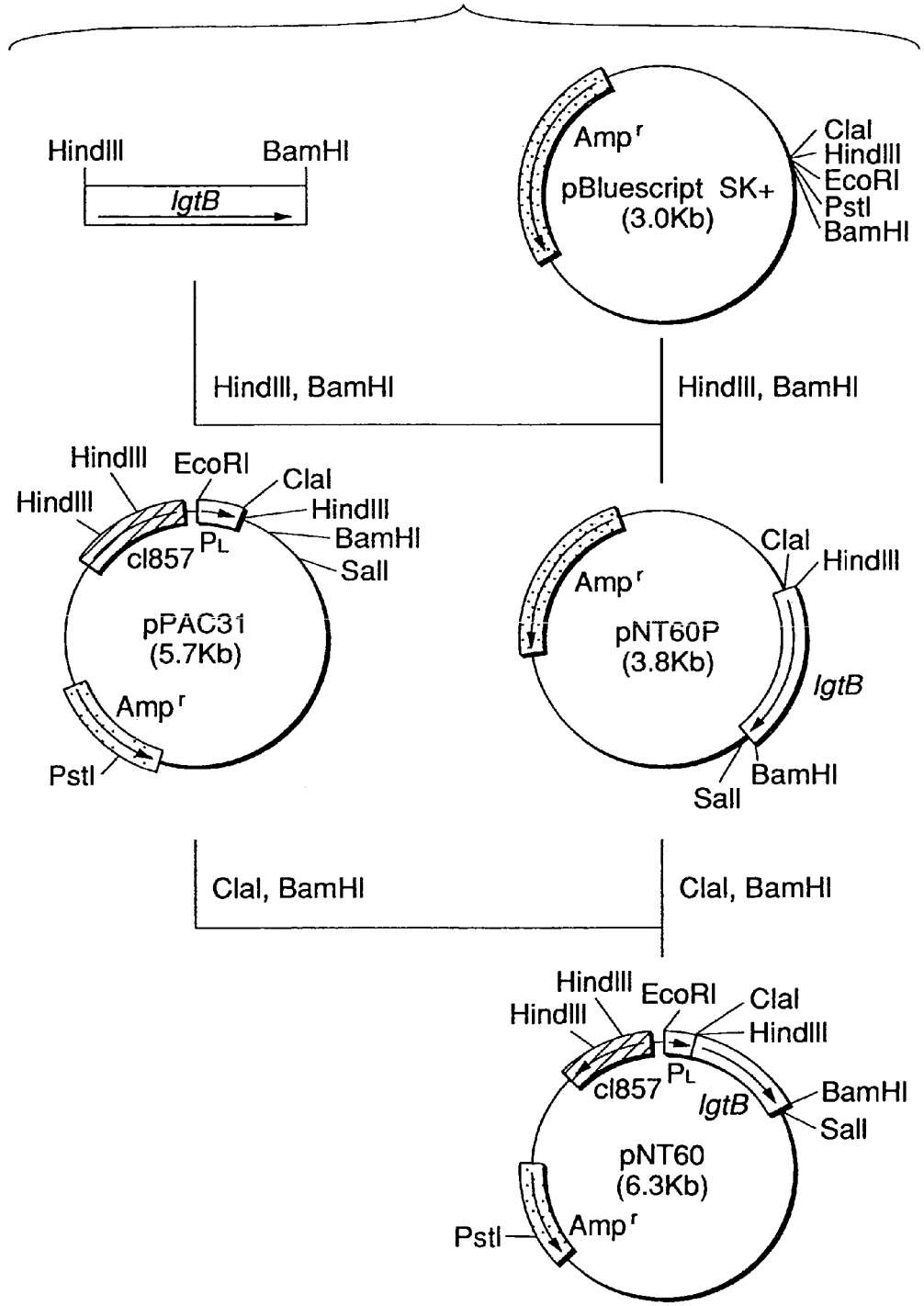
FIG. 16 shows construction steps of lgtB gene expression plasmid pNT60.

By extracting a plasmid from the thus grown colonies of the transformant in accordance with the usual process, plasmid pNT60P containing the lgtB gene was obtained. Structure of the plasmid was recognized by restriction enzyme cleavage (FIG. 16).

A 0.5 µg portion of the pNT60P DNA was cleaved with restriction enzymes ClaI and BamHI, the resulting DNA fragments were separated by agarose gel electrophoresis and then a fragment of 0.8 kb was recovered. A 0.2 µg portion of the pPAC31 DNA obtained in Example 1-1) was cleaved with restriction enzymes ClaI and BamHI, the resulting DNA fragments were separated by agarose gel electrophoresis and then a fragment of 5.5 kb was recovered in the same manner.

Using a ligation kit, the fragments of 0.8 kb and 5.5 kb were subjected to ligation reaction for 16 hours at 16° C.

Using the ligation reaction solution, *Escherichia coli* NM522 was transformed in accordance with the usual process, and the resulting transformant was spread on LB agar medium containing 50 µg/ml ampicillin and then cultured overnight at 30° C.

By extracting a plasmid from the thus grown colonies of the transformant in accordance with the usual process, a lgtB expression plasmid pNT60 was obtained. Structure of the plasmid was recognized by restriction enzyme cleavage (FIG. 16).

Example 26

Production of N-acetyllactosamine

*Escherichia coli* NM522/pNT60 obtained in Example 25 and *Escherichia coli* NM522/pNT25 obtained in Example 3 were cultured in the same manner as in Example 2, and each of the thus obtained culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 50 g/l *Escherichia coli* NM522/pNT25 wet cells, 50 g/l *Escherichia coli* NM522/pNT60 wet cells, 150 g/l *Corynebacterium ammoniagenes* ATCC 21170 wet cells, 10 g/l orotic acid (potassium salt), 100 g/l fructose, 100 g/l N-acetylglucosamine, 100 g/l galactose, 15 g/l $KH_2PO_4$, 5 g/l $MgSO_4 \cdot 7H_2O$, 5 g/l phytic acid, 4 g/l Nymeen S-215 and 10 ml/l xylene was put into a 200 ml beaker, and 34 hours of the reaction was carried out at 32° C. under stirring the reaction solution with a magnetic stirrer (900 rpm).

During the reaction, pH of the reaction solution was maintained at 7.2 using 4 N NaOH, and galactose, fructose and $KH_2PO_4$ were added when required.

By the reaction, 114 g/l N-acetyllactosamine was formed in the reaction solution.

Example 27

Production of Lactose

*Escherichia coli* NM522/pNT60 obtained in Example 25 and *Escherichia coli* NM522/pNT25 obtained in Example 3 were cultured in the same manner as in Example 2, and each of the thus obtained culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 50 g/l *Escherichia coli* NM522/pNT25 wet cells, 50 g/l *Escherichia coli* NM522/pNT60 wet cells, 150 g/l *Corynebacterium ammoniagenes* ATCC 21170 wet cells, 10 g/l orotic acid (potassium salt), 115 g/l glucose, 115 g/l galactose, 15 g/l $KH_2PO_4$, 5 g/l $MgSO_4.7H_2O$, 5 g/l phytic acid, 4 g/l Nymeen S-215 and 10 ml/l xylene was put into a 200 ml beaker, and 15 hours of the reaction was carried out at 32° C. by stirring the reaction solution on a magnetic stirrer (900 rpm).

During the reaction, pH of the reaction solution was maintained at 7.2 using 4 N NaOH, and $KH_2PO_4$ was added when required.

By the reaction, 49 g/l lactose was formed in the reaction solution.

Example 28

Production of Globotriose

*Escherichia coli* NM522/pNT60 obtained in Example 25, *Escherichia coli* NM522/pNT25 obtained in Example 3 and *Escherichia coli* NM522/pGT3 obtained in Example 22 were cultured in the same manner as in Example 2, and each of the thus obtained culture broths was centrifuged to obtain wet cells. Also, *Corynebacterium ammoniagenes* ATCC 21170 was cultured in the same manner as in Example 2, and the culture broth was centrifuged to obtain wet cells. As occasion demands, these wet cells can be preserved at −20° C. and utilized by thawing the cells prior to use.

A 30 ml portion of a reaction solution having a composition of 50 g/l *Escherichia coli* NM522/pNT25 wet cells, 50 g/l *Escherichia coli* NM522/pNT60 wet cells, 50 g/l *Escherichia coli* NM522/pGT3 wet cells, 150 g/l *Corynebacterium ammoniagenes* ATCC 21170 wet cells, 10 g/l orotic acid (potassium salt), 115 g/l glucose, 115 g/l galactose, 15 g/l $KH_2PO_4$, 5 g/l $MgSO_4.7H_2O$, 5 g/l phytic acid, 4 g/l Nymeen S-215 and 10 ml/l xylene was put into a 200 ml beaker, and 13 hours of the reaction was carried out at 32° C. under stirring the reaction solution with a magnetic stirrer (900 rpm).

During the reaction, pH of the reaction solution was maintained at 7.2 using 4 N NaOH, and $KH_2PO_4$ was added when required.

By the reaction, 5 g/l globotriose was formed in the reaction solution.

INDUSTRIAL APPLICABILITY

The present invention renders possible efficient industrial production of a sugar nucleotide from a nucleotide precursor and a sugar as the sole starting materials and of a complex carbohydrate from the sugar nucleotide and a complex carbohydrate precursor.

What is claimed is:

1. A process for producing a complex carbohydrate, which comprises:
    selecting, as enzyme sources, (a) a culture of a microorganism belonging to the genus *Corynebacterium* and capable of producing NTP from a nucleotide precursor, or a treated product of the culture, (b) a culture of at least one microorganism belonging to the genus *Escherichia* or *Corynebacterium*, said culture being capable of producing a sugar nucleotide from a sugar and NTP, or a treated product of the culture and (c) a culture at least one microorganism belonging to the genus *Escherichia* or *Corynebacterium*, said culture being capable of intracellularly producing a complex carbohydrate from a sugar nucleotide and a complex carbohydrate precursor, or a treated product of the culture;
    allowing the enzyme sources, the nucleotide precursor, the sugar and the complex carbohydrate precursor to be present in an aqueous medium to form and accumulate the complex carbohydrate in the aqueous medium; and
    recovering the complex carbohydrate from the aqueous medium,
    wherein the sugar nucleotide is a uridine diphosphate compound, a guanosine diphosphate compound or a cytidine monophosphate compound, and
    wherein the treated product of culture is a concentrated product of the culture, a dried product of the culture, cells obtained by centrifuging the culture, a dried product of the cells, a freeze-dried product of the cells, a surfactant-treated product of the cells, a solvent-treated product of the cells, an enzyme-treated product of the cells, or an immobilized product of the cells.

2. A process for producing a complex carbohydrate, which comprises:
    (I) selecting, as enzyme sources, (a) a culture of a microorganism belonging to the genus *Corynebacterium* and capable of producing NTP from a nucleotide precursor, or a treated product of the culture, and (b) a culture of at least one microorganism belonging to the genus *Escherichia* or *Corynebacterium* capable of producing a sugar nucleotide from a sugar and NTP, or a treated product of the culture;
    allowing the enzyme sources, the nucleotide precursor and the sugar to be present in an aqueous medium to form and accumulate the sugar nucleotide in the aqueous medium; and
    recovering the sugar nucleotide from the aqueous medium, and
    (II) selecting, as an enzyme source, a culture of a microorganism belonging to the genus *Escherichia* or *Coryne-* bacterium capable of intracellularly producing a complex carbohydrate from a sugar nucleotide and a complex carbohydrate precursor, or a treated product of the culture;

allowing the enzyme source, the complex carbohydrate precursor and the sugar nucleotide prepared by (I) to be present in an aqueous medium to form and accumulate the complex carbohydrate in the aqueous medium; and recovering the complex carbohydrate from the aqueous medium, wherein the sugar nucleotide is a uridine diphosphate compound, a guanosine diphosphate compound or a cytidine monophosphate compound, and wherein the treated product of culture is a concentrated product of the culture, a dried product of the culture, cells obtained by centrifuging the culture, a dried product of the cells, a freeze-dried product of the cells, a surfactant-treated product of the cells, a solvent-treated product of the cells, an enzyme-treated product of the cells, or an immobilized product of the cells.

3. The process according to claim 1 or 2, wherein the nucleotide precursor is orotic acid, uracil, orotidine, uridine, cytosine, cytidine, adenine, adenosine, guanine, guanosine, hypoxanthine, inosine, xanthine, xanthosine, inosine-5'-monophosphate, xanthosine-5' monophosphate, guanosine-5'-monophosphate, uridine-5'-monophosphate or cytidine-5'-monophosphate.

4. The process according to claim 1 or 2, wherein the uridine diphosphate compound, guanosine diphosphate compound or cytidine monophosphate compound is selected from the group consisting of uridine diphosphoglucose, uridine diphosphogalactose, uridine diphospho-N-acetylglucosamine, uridine diphospho-acetylgalactosamine, uridine diphosphoglucuronic acid, guanosine diphosphomannose, guanosine diphosphofucose, cytidine monophospho-N-acetylneuraminic acid, and derivatives thereof.

5. The process according to claim 1 or 2, wherein the sugar is selected from the group consisting of glucose, fructose, galactose, glucosamine, N-acetylglucosamine, N-acetylgalactosamine, mannose, fucose, N-acetylmannosamine, acetylneuraminic, and derivatives thereof.

6. The process according to claim 1 or 2, wherein the complex carbohydrate contains at least one sugar selected from the group consisting of glucose, galactose, N-acetylglucosamine, N-acetylgalactosamine, glucuronic acid, mannose, N-acetylmannosamine, fucose, sialic acid, lactose, N-acetyllactosamine, lacto-N-biose, GlcNAcfβ1-3Galβ1-4Glc, GlcNAcβ1-4Galβ1-4Glc, globotriose, Galα1-4Galβ1-4GlcNAc, 2'-fucosyllactose, 3-fucosyllactose, 3'-sialyllactose, 6'-sialyllactose, 3'-sialyl-N-acetyllactosamine, 6'-sialyl-N-acetyllactosamine, sialyllacto-N-biose, Lewis X, Lewis a, lacto-N-tetraose, lacto-N-neotetraose, lactodifucotetraose, 3'-sialyl-3-fucosyllactose, sialyl-Lewis X, sialyl-Lewis a, lacto-N-fucopentaose I, lacto-N-fucopentaose II, lacto-N-fucopentaose III, lacto-N-fucopentaose V, LS-tetrasaccharide a, LS-tetrasaccharide b, LS-tetrasaccharide c, (α2,3)sialyllacto-N-neotetraose, lacto-N-difucohexaose I, lacto-N-difucohexaose II, lacto-N-hexaose, lacto-N-neohexaose, disialyllacto-N-tetraose, and derivatives thereof.

7. The process according to claim 1 or 2, wherein the complex carbohydrate contains a sugar having a bond selected from the group consisting of Galβ1-3Glc, Galβ1-4Glc, Galβ1-3GlcNAc, Galβ1-4GlcNAc, Galβ1-3Gal, Galβ1-4Gal, Galβ1-3GalNAc, Galβ1-4GalNAc, Galα1-3Glc, Galα1-4Glc, Galα1-3GlcNAc, Galα1-4GlcNAc, Galα1-3Gal, Galα1-4Gal, Galα1-3GalNAc, Galα1-4GalNAc, GlcNAcβ1-3Gal, GlcNAcβ1-4Gal, GlcNAcβ1-6Gal, GlcNAcβ1-3Glc, GlcNAcβ1-4Glc, GlcNAcβ1-3GlcNAc, GlcNAcβ1-4GlcNAc, GlcNAcβ1-6GalNAc, GlcNAcβ1-2Man, GlcNAcβ1-4Man, GlcNAcβ1-6Man, GalNAcβ1-3Gal, GalNAcβ1-4Gal, GalNAcβ1-4GlcNAc, GalNAcα1-3GalNAc, Manβ1-4GlcNAc, Manα1-6Man, Manα1-3Man, Manα1-2Man, GlcUAβ1-4GlcN, GlcUAβ1-3Gal, GlcUAβ1-3GlcNAc, GlcUAβ1-3GalNAc, NeuAcα2-3Gal, NeuAcα2-6Gal, NeuAcα2-3GlcNAc, NeuAcα2-6GlcNAc, NeuAcα2-3GalNAc, NeuAcα2-6GalNAc, NeuAcα2-8NeuAc, Fucα1-3Glc, Fucα1-4Glc, Fucα1-3GlcNAc, Fucα1-4GlcNAc, Fucα1-2Gal and Fucα1-6GlcNAc.

8. The process according to claim 6, wherein the number of sugars contained in the complex carbohydrate is 10 or fewer.

9. The process according to claim 6, wherein the number of sugars contained in the complex carbohydrate is 6 or fewer.

10. The process according to claim 1 or 2, wherein the complex carbohydrate precursor is selected from the group consisting of monosaccharides, oligosaccharides, proteins, peptides, lipids, glycoproteins, glycolipids, glycopeptides and steroid compounds.

11. The process according to claim 10, wherein the complex carbohydrate precursor is selected from the group consisting of glucose, galactose, mannose, sialic acid, N-acetylglucosamine, N-acetylgalactosamine, lactose, N-acetyllactosamine, lacto-N-biose, GlcNAcβ1-3Galβ1-4Glc, GlcNAcβ1-4Galβ1-4Glc, globotriose, Galα1-4Galβ1-4GlcNAc, 2'-fucosyllactose, 3-fucosyllactose, 3'-sialyllactose, 6'-sialyllactose, 3'-sialyl-N-acetyllactosamine, 6'-sialyl-acetyllactosamine, sialyllacto-N-biose, Lewis X, Lewis a, lacto-N-tetraose, lacto-N-neotetraose, lactodifucotetraose, 3'-sialyl-3-fucosyllactose, sialyl-Lewis X, sialyl-Lewis a, lacto-N-fucopentaose I, lacto-N-fucopentaose II, lacto-N-fucopentaose III, lacto-N-fucopentaose V, LS-tetrasaccharide a, LS-tetrasaccharide b, LS-tetrasaccharide c, (α2,3)sialyllacto-N-neotetraose, and derivatives thereof, serine, threonine, asparagine and peptides containing these amino acids and derivatives thereof, and ceramide and derivatives thereof.

12. The process according to claim 1, wherein the microorganisms of (b) and (c) comprise *Corynebacterium ammoniagenes*.

13. The process according to claim 1 or 2, wherein at least two microorganisms collectively are capable of producing a sugar nucleotide from a sugar and NTP.

14. The process according to claim 13, wherein at least one of said at least two microorganisms is *Escherichia*.

15. The process according to claim 13, wherein at least one of said at least two microorganisms is *Corynebacterium ammoniagenes*.

16. The process, according to claim 7, wherein the number of sugars contained in the complex carbohydrate is 10 or fewer.

17. The process according to claim 7, wherein the number of sugars contained in the complex carbohydrate is 6 or fewer.

18. The process according to claim 1 or 2, wherein the microorganism capable of producing a complex carbohydrate from a sugar nucleotide and a complex carbohydrate precursor is transformed with glucosyltransferase gene isolated from prokaryote.

19. The process according to claim 3, wherein the microorganisms of (I)-(b) or (II) comprise *Corynebacterium ammoniagenes*.

20. The process according to claim 19, wherein the microorganisms of (I)-(b) and (II) both comprise *Corynebacterium ammoniagenes*.

21. The process according to claim 13, wherein both of said microorganisms belong to the genus Escherichia or both of said microorganisms belong to the genus *Corynebacterium*.

* * * * *

UNITED STATES PATENT AND TRADEMARK OFFICE
CERTIFICATE OF CORRECTION

PATENT NO.      : 8,435,763 B2
APPLICATION NO. : 10/940026
DATED           : May 7, 2013
INVENTOR(S)     : Satoshi Koizumi et al.

It is certified that error appears in the above-identified patent and that said Letters Patent is hereby corrected as shown below:

In the Specification

COLUMN 3:

Line 5, "bloth" should read --broth--; and
Line 29, "galu," should read --galU,--.

COLUMN 9:

Line 5, "(pNKB)" should read --(pNK8)--; and
Line 43, "D techniques" should read --DNA techniques--.

COLUMN 15:

Line 60, "seen S-215," should read --Nymeen S-215--; and
Line 62, "ethylaimonium" should read --ethylammonium--; and "alkyldirmethyl
    benzylamonium" should read --alkyldimethyl benzylammonium--.

COLUMN 16:
Lines 11-12, "The sugar nucleotide can be formed by the process. Examples" should
    read --Examples of the sugar nucleotide that can be formed by the process--; and
Line 45, "for" should read --for use--.

COLUMN 18:

Line 41, "4-glc," should read --4-Glc,--.

Signed and Sealed this
Twenty-fourth Day of December, 2013

Margaret A. Focarino
*Commissioner for Patents of the United States Patent and Trademark Office*

CERTIFICATE OF CORRECTION (continued)
U.S. Pat. No. 8,435,763 B2

In the Specification

COLUMN 19:

Line 2, "LS-tetrasaccharide C," should read --LS-tetrasaccharide c,--;
Line 11, "Galᴣ1-3Glc," should read --Galα1-3Glc,--;
Line 23, "NeuAcα2-8Neuc," should read --NeuAcα2-8NeuAc,--;
Line 50, "mannosaiine," should read --mannosamine,--; and
Line 62, "(α2,3-sialyltransferase" should read --α2,3-sialyltransferase--.

COLUMN 20:

Line 34, "GlcNAᴣ1-3Galᴣ1-4Glc" should read --GlcNAcᴣ1-3Galᴣ1-4Glc--.

COLUMN 21:

Line 4, "precursot" should read --precursor--;
Line 5, "product" should read --produce--; and
Line 25, "sources;" should read --sources,--.

COLUMN 22:

Line 17, "(α1,3/1,4-fucosyltransferase" should read --α1,3/1,4-fucosyltransferase--;
Line 18, "Research," should be italicized; and
Line 64, "*Prapionibacterium*" should read --*Propionibacterium*--.

COLUMN 23:

Line 11, "6 toxin," should read --* toxin,--.

COLUMN 24:

Line 53, "antisence" should read --antisense--.

COLUMN 25:

Line 40, "antisence" should read --antisense--.

COLUMN 27:

Line 34, "antisence" should read --antisense--; and
Line 53, "NH522" should read --NM522--.

In the Specification

COLUMN 28:

Line 7, "NM52" should read --NM522--.

COLUMN 30:

Line 18, "antisence" should read --antisense--; and
   Line 65, "glmu," should read --glmU,--.

COLUMN 31:

Line 3, "antisence" should read --antisense--;
   Line 33, "antisence" should read --antisense--; and
   Line 63, "antisence" should read --antisense--.

COLUMN 32:

Line 50, "antisence" should read --antisense--.

COLUMN 35:

Line 45, "antisence" should read --antisense--.

COLUMN 36:

Line 53, "antisence" should read --antisense--.

COLUMN 37:

Line 40, "the" should be deleted; and
   Line 58, "antisence" should read --antisense--.

COLUMN 38:

Line 58, "antisence" should read --antisense--.

COLUMN 40:

Line 12, "plasmic" should read --plasmid--.

COLUMN 41:

Line 23, "(5mM" should read --(5mM)--.

CERTIFICATE OF CORRECTION (continued)
U.S. Pat. No. 8,435,763 B2

In the Specification

COLUMN 42:

Line 9, "antisence" should read --antisense--.

COLUMN 43:

Line 48, "antisence" should read --antisense--.

COLUMN 55:

Line 53, "culture" (second occurrence) should read --culture of--.

COLUMN 57:

Line 44, "GlcNAcfꓱ1-3Galꓱ1-" should read --GlcNAcꓱ1-3Galꓱ1- --.

In the Claims

COLUMN 58:

Line 54, "claim 3," should read --claim 2,--; and
　　　Line 61, "Escherichia" should be italicized.